US007892778B2

(12) United States Patent
Hoppe et al.

(10) Patent No.: US 7,892,778 B2
(45) Date of Patent: Feb. 22, 2011

(54) METHOD OF SCREENING FOR GAMMA-SECRETASE ACTIVITY

(75) Inventors: Edmund Hoppe, Krailling (DE); Gisela Peraus, München (DE); Jonathan Rothblatt, Somerville, MA (US); Ekkehard Leberer, Germering (DE); Luc Mercken, Saint Maur (FR); Sylvie Dreisler, Verrières (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 22 days.

(21) Appl. No.: 10/849,423

(22) Filed: May 19, 2004

(65) Prior Publication Data

US 2005/0032150 A1 Feb. 10, 2005

Related U.S. Application Data

(60) Provisional application No. 60/520,567, filed on Nov. 17, 2003.

(30) Foreign Application Priority Data

May 26, 2003 (EP) ................................ 03011807

(51) Int. Cl.
*C12Q 1/37* (2006.01)

(52) U.S. Cl. ........................................................ 435/23

(58) Field of Classification Search ....................... None
See application file for complete search history.

(56) References Cited

FOREIGN PATENT DOCUMENTS

WO WO 00/34511 6/2000

OTHER PUBLICATIONS

Lim et al., Cloning trap for signal peptide sequences. Biotechniques. Jan. 2000;28(1):124-6, 128-30.*

Smith et al., Direct selection for sequences encoding proteases of known specificity. Proc Natl Acad Sci U S A. Jun. 15, 1991;88(12):5159-62.*

Baty et al, Secretion into the bacterial periplasmic space of chicken ovalbumin synthesized in *Escherichia coli*. Gene. Dec. 1981;16(1-3):79-87.*

Ohkubo et al, Substrate phage as a tool to identify novel substrate sequences of proteases. Comb Chem High Throughput Screen. Nov. 2001 ;4(7):573-83.n.*

Houdebine et al, The methods to generate transgenic animals and to control transgene expression. Journal of Biotechnology vol. 98, Issues 2-3, Sep. 25, 2002, pp. 145-160.*

Dovey, H. F., et al., Funtional gamma-secretase inhibitors reduce beta-amyloid peptide levels in brain, Journal of Neurochemistry, (2001), vol. 76, pp. 173-181.

Elledge, Stephen J. et al., YES: A multifunctional cDNA expression vector for the Isolation of genes by complementation of yeast and *Escherichia coli* mutations, Proc. Natl. Acad. Sci. USA, (1991), vol. 88, pp. 1731-1735.

Hilbich, Caroline et al., Aggregation and Secondary Structure of Synthetic Amylid BetaA4 Peptides of Alzheimer's Disease, J. Mol. Biol., (1991), pp. 149-163.

Ikeda, Keiko et al., Involvement of Negative Cofactor NC2 in Active Repression by Zinc Finger-Homeodomain Transcription Factor AREB6, Molecular and Cellular Biology, (1998), vol. 18, No. 1, pp. 10-18.

Kretzschmar, Marcus et al., RNA Polymerase II Cofactor PC2 Facilitates Activation of Transcription by GAL4-AH In Vitro, Molecular and Cellular Biology, (1994), vol. 14, pp. 3927-3937.

Kretzschmar, Marcus et al., RNA Polymerase II Cofactor PC2 Facilitates Activation of Transcription by GAL4-AH In Vitro, Molecular and Cellular Biology, (1994), vol. 14, pp. 3927-3937.

Maruyama, Kei et al., Cleavage At the N-Terminal Site of Alzheimer Amyloid Beta/Alpha 4 Protein Is Essential for Its Secretion, Biochemical and Biophysical Research Communications, (1994), vol. 202, No. 3, pp. 1517-1523.

Mattson, Mark P., Ballads of a protein quartet, Nature, (2003), vol. 422, pp. 385-386.

Mumberg, Dominik et al., Regulatable promotors of *Saccharomyces cerevisiae*: comparison of transcriptional activity and their use for heterologous expression, Nucleic Acid Research, (1994), vol. 22, No. 25, pp. 5767-5768.

Mumberg, Dominik et al., Yeast vectors for the controlle expression of heterologous proteins in different genetic backgrounds, Gene, (1995), vol. 156, pp. 119-122.

Rumble, Baden et al., Amyloid A4 Protein and its Precursor in Downs Syndrome and Alzheimer's Disease, The New England Journal of Medicine, (1989), pp. 1446-1452.

Sadowski, et al., Ivan, GAL4-VP16 is an unusually potent transcriptional activator, Nature, (1988), vol. 335, pp. 563-564.

Scheuner, D. et al., Secreted amyloid Beta-protein similar to that in the senile plaques of Alzheimer's disease is increased in vivo by the presenilin 1 and 2 and APP mutations linked to familial Alzheimer's disease, Nature Medicine, (1996), vol. 2, No. 8, pp. 864-870.

Shearman, Mark S. et al., L-685,458, an Aspartyl Protease Transition State Mimic, Is a Potent Inhibitor of Amyloid Beta-Protein Precursor Gamma-Secretase Activity, Biochemistry, (2000), vol. 39, pp. 8698-8704.

Suzuki, Nobuhiro et al., An Increased Percentage of Long Amyloid Beta Protein Secreted by Familial Amyloid Beta Protein Precursor (BetaAPP717) Mutants, Science, (1994), vol. 264, pp. 1336-1340.

Unterbeck, et al., Axel, The precursor of Alzheimer's disease amyloid A4 protein resembles a cell-surface receptor, Nature, (1987), vol. 325. pp. 733-736.

Vidal, Marc at al., Reverse two-hybrid and one-hybrid systems to detect dissociation of protein-protein and DNA-protein interactions, Proc. Natl. Acad. Sci. USA, (1996), vol. 93, pp. 10315-10320.

(Continued)

*Primary Examiner*—Sheridan Swope

(57) ABSTRACT

The present invention relates to an improved process for determining γ-secretase activity and for detecting γ-secretase, a subunit protein of γ-secretase, or a γ-secretase-like proteinase. In particular, the present invention relates to processes for the identification of a γ-secretase or of a cDNA which codes for a γ-secretase, a subunit protein of γ-secretase, or a γ-secretase-like proteinase. Another embodiment of the present invention relates to processes for the identification of substances which can inhibit the activity of γ-secretase, or a γ-secretase-like proteinase.

11 Claims, 4 Drawing Sheets

OTHER PUBLICATIONS

Yankner, Bruce A. et al., Nerve growth factor potentiates the neurotoxicity of Beta amyloid, Proc. Natl. Acad. Sci. USA, (1990), vol. 87, pp. 9020-9023.

von Heijne, Gunnar, A new method for predicting signal sequence cleavage sites, Nucleic Acids Research, (1996), vol. 14, No. 11.

* cited by examiner

METHOD OF SCREENING FOR GAMMA-SECRETASE ACTIVITY

RELATED APPLICATIONS

This application claims the benefit of priority under 35 U.S.C. §119 of EP Application No. 1 481 987 A1 filed May 26, 2003, and of U.S. Provisional Application No. 60/520,567 filed on Nov. 17, 2003, the contents of both of which are incorporated by reference.

BACKGROUND

Alzheimer's disease (AD) is a neurodegenerative disorder of the brain, which is accompanied at the cellular level by a massive loss of neurons in the limbic system and in the cerebral cortex. In the brain areas affected, protein deposits, so-called plaques, can be detected at the molecular level, which are an essential characteristic of Alzheimer's disease. The protein occurring most frequently in these plaques is a peptide of 40 to 42 amino acids, which is designated as Aβ-peptide. This Aβ-peptide is a cleavage product of a significantly larger protein of 695 to 770 amino acids, the so-called amyloid precursor protein (APP).

APP is an integral transmembrane protein, which firstly traverses the lipid bilayer. By far the largest part of the protein is extracellular, while the shorter C-terminal domain is directed into the cytosol (FIG. 1). The Aβ-peptide is shown dark-gray in FIG. 1. About two thirds of the Aβ-peptide originates from the extracellular domain and about one third from the transmembrane domain of APP.

Beside the membrane-based APP, a secreted form of the amyloid precursor protein can be detected which consists of the large ectodomain of the APP and is designated as $APP_{sec}$ ("secreted APP"). $APP_{sec}$ is formed from APP by proteolytic cleavage, which is effected by the α-secretase. The proteolytic cleavage takes place in a site of the amino acid sequence of APP, which is within the amino acid sequence of the Aβ-peptide (after amino acid residue 16 of the Aβ-peptide). Proteolysis of APP by the α-secretase thus excludes the formation of the Aβ-peptide.

The Aβ-peptide can thus only be formed from APP in an alternative processing route. It is postulated that two further proteases are involved in this processing route, one protease, which is designated as β-secretase, cleaving at the N-terminus of the Aβ-peptide in the APP and the second protease, which is designated as γ-secretase, releasing the C-terminus of the Aβ-peptide (Kang, J. et al., Nature, 325, 733) (FIG. 1).

To learn more about the secretases (α-secretase, β-secretase, γ-secretase) is of great interest, in particular in the context of investigations on Alzheimer's disease, e.g., for the identification of the secretases or factors involved in secretase regulation and Aβ-peptide formation (Wolfe, M. S. (2001), J. Med. Chem., 44(13), 2039-2060). The inhibition of β-secretase and in particular of γ-secretase could lead to a reduction in the Aβ-production, on the other hand an activation of the α-secretase could increase the processing of APP in APPsec and would thus simultaneously reduce the formation of the Aβ-peptide. A transgenic *C. elegans*, which is found in the course of such investigations is described in the U.S. Pat. No. 6,673,600, the contents of which are incorporated herein by reference.

There are many indications that the Aβ-peptide (Aβ) is a crucial factor in the occurrence of Alzheimer's disease. Inter alia, neurotoxicity of Aβ-fibrils in cell culture is postulated (Yankner, B. A. et al., (1990) Proc Natl Acad Sci USA, 87, 9020). In patients with Down's syndrome, in which the gene encoding APP occurs in an additional copy, the neuropathology characteristic of Alzheimer's disease also occurs even at an age of 30 years. Here, it is assumed that the overexpression of APP follows an increased conversion into the Aβ-peptide (Rumble, B. et al., (1989), N. Engl. J. Med., 320, 1446). great Probably the strongest indication of the central role of the Aβ-peptide is the familial forms of Alzheimer's disease. Here, mutations are found in the APP gene around the area of the β- and γ-secretase cleavage sites or in two further AD-associated genes (presenilins), which in cell culture lead to a significant increase in Aβ-peptide production (Scheuner, D. et al., (1996), Nature Medicine, 2, 864).

There are a number of indications of the fact that APP is firstly cleaved into the Aβ-peptide by the β-secretase during its processing in order to serve subsequently as a substrate for γ-secretase. The γ-secretase therefore has a crucial role in the formation of the Aβ-peptide (Wolfe, M. S. (2001), loc.cit).

In general, the detection of Aβ-peptide is difficult, since only a small amount of APP is converted (Simons M, et al., Neurosci (1996) 1; 16(3):899-908). Moreover, the Aβ-peptide is a very small fragment of about 4 kDa, which has a great tendency to self-aggregation due to its hydrophobic character. Accordingly, Aβ-peptide easily precipitates under physiological conditions (Hilbich, C. et al., (1991) J. Mol. Biol., 218, 149) and is in its precipitated form not available for detection.

The detection of the Aβ-peptide in eukaryotic cells is carried out by means of immunobiological methods such as, e.g., ELISA, immunoprecipitation and Western blotting (Suzuki, N. et al., Science 1994, 27, 264(5163) 1336; Haass, C. et al., (1992) Nature, 359, 322). Further, an in vitro assay for the determination of γ-secretase activity from purified membrane fractions containing PS1 (presenilin 1) was described by Wolfe et al. (1999). These processes are very time consuming, as they involve incubation steps with appropriate antibodies, steps destroying the cells obtained from suitable cell culture or model organisms (e.g., *C. elegans*). The said methods are not suitable in an automated assay system, e.g., for high throughput screening, to identify compounds, which specifically inhibit or decrease the activity of a γ-secretase. In part, this is because γ-secretase activity is dependent upon an assembly of proteins (Mattson, (2003) Nature 422, 385), which is, to date, only active in a complex membrane lipid environment.

Further, the activity of the γ-secretase can be demonstrated according to the teachings of WO00/34511A2, the contents of which are incorporated herein by reference, which describes a process for the determination of γ-secretase activity and for the detection of γ-secretase by the detection of the Aβ-peptide. The process of WO00/34511A2 utilizes a transgene which encodes a fusion protein comprising: the amino acid sequence GAIIGLMVGGVVIATVIVITLVML (SEQ ID NO. 1) as the enzymatic target site of γ-secretase, a signal peptide (SP) at the 5'-end, a promoter and, if appropriate, further coding and/or non-coding nucleotide sequences, which is incorporated into a cell in order to express the said fusion protein.

When the fusion protein is specifically cleaved by the γ-secretase present in the cell, a first partial protein is formed, containing the amino acid sequence GAIIGLMVGGVV (SEQ ID NO. 2), and a second partial protein is formed, containing the amino acid sequence VIVITLVML (SEQ ID NO. 3). Subsequently, the said first and/or second partial protein is detected, e.g., by use of a suitable reporter, which is, e.g., a reporter gene, which is activated by the release of a transcription activator coupled to the first and/or second partial protein.

Due to the known problems accompanied with the detection of Aβ-peptide, it is the problem of instant invention to improve the process of WO00/34511A2, e.g., by decreasing the background signal and/or increasing the signal specificity, in order to improve the signal/noise ratio in the assay of the invention.

DETAILED DESCRIPTION OF THE INVENTION

Figure 1:
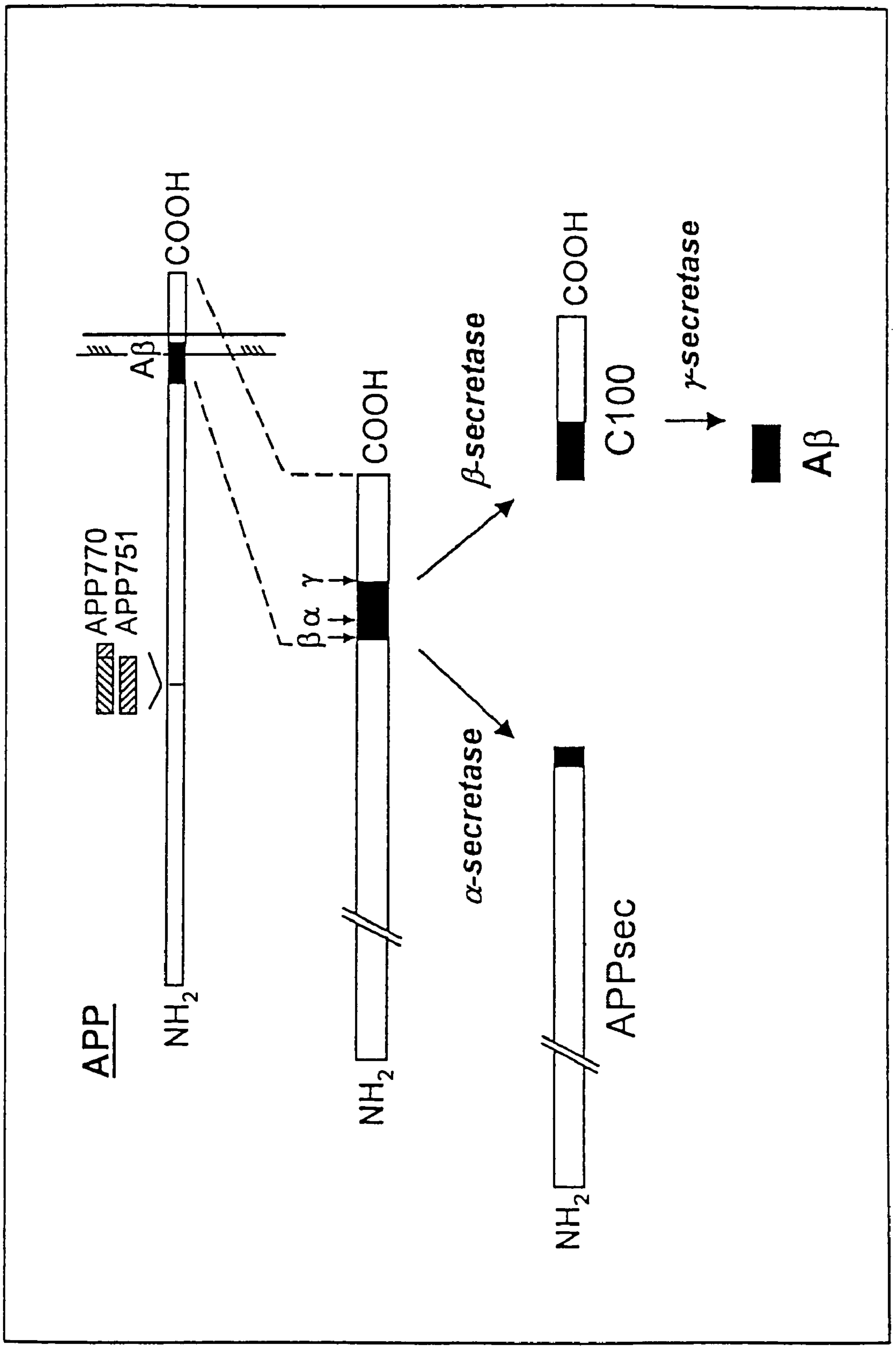
FIG. 1 shows the amyloid precursor protein (Isoform APP695 and Isoforms APP770 or APP751) and secretase cleavage products.

Surprisingly, it is possible to improve the signal/noise ratio in a process according to WO00/34511A2 by decreasing the unspecific release of first and/or second partial proteins due to unspecific protease activity. This is achieved, e.g., in the fusion peptide of WO00/34511A2, by the exclusion/avoidance of any other sequences/motifs of protease cleavage sites and/or internalization sequences—beside the γ-secretase cleavage site. Therefore, the present invention relates to an improved process for the determination of γ-secretase activity and the detection of a protein having γ-secretase activity.

Particular embodiments of the process relate to processes for the identification of a γ-secretase, of a cDNA which codes for a γ-secretase, a subunit protein of γ-secretase, or a γ-secretase-like proteinase, and processes for the identification of a pharmaceutical active compound, which can modulate, e.g., decrease or inhibit the activity of a protein having γ-secretase activity. Such substances are of particular interest, if pharmaceutically acceptable and suitable for the treatment of Alzheimer's disease.

The present invention relates to a process for the detection of γ-secretase, wherein 1. a transgene is used which encodes a fusion protein and contains the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide,
   c) a promoter and,
   d) if appropriate, further coding and/or non-coding nucleotide sequences;
2. this transgene is incorporated into a cell and the fusion protein is expressed;
3. the fusion protein is cleaved within the amino acid sequence SEQ ID NO. 1 by γ-secretase present in the cell, whereby a first partial protein, which contains the amino acid sequence GAIIGLMVGGVV (SEQ ID NO. 2), and a second partial protein, which contains the amino acid sequence VIVITLVML (SEQ ID NO. 3), are formed and
4. the first partial protein and/or the second partial protein are detected, wherein with the proviso/exception of SEQ ID No. 1 said fusion protein does not contain one or more peptides acting as a signal for endo- or exocytosis and/or protease cleavage site.

Preferably, in the said process said fusion protein does not contain one or more (i.e., beside SEQ ID No. 1 any further peptide) peptides acting as a signal for endo- or exocytosis and protease cleavage site with the exception of the SEQ ID No. 1.

The invention also relates to a process for the detection of the activity of γ-secretase, wherein 1. a transgene is prepared/used which encodes a fusion protein and contains the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide,
   c) a promoter and,
   d) if appropriate, further coding and/or non-coding nucleotide sequences;
2. this transgene is incorporated into a cell and the fusion protein is expressed;
3. the fusion protein is cleaved within the amino acid sequence SEQ ID NO. 1 by γ-secretase present in the cell, whereby a first partial protein, which contains the amino acid sequence GAIIGLMVGGVV (SEQ ID NO. 2), and a second partial protein, which contains the amino acid sequence VIVITLVML (SEQ ID NO. 3), are formed;
4. the amount of second partial protein is determined and the activity of the γ-secretase is determined from the amount of second partial protein formed, wherein with the proviso/exception of SEQ ID No. 1 said fusion protein does not contain one or more peptides acting as a signal for endo- or exocytosis and/or protease cleavage site.

The processes according to the invention ("Aβ-peptide screening assay", "γ-secretase assay") are suitable for the in vivo detection of a γ-secretase (protein having γ-secretase activity) or of the activity of a γ-secretase, enabling to employ the processes universally, even, e.g., in high throughput screening ("HTS") assays. The processes do not have the above-mentioned disadvantages of the conventional detection processes, particularly, laborious isolation and detection steps are avoided and the specific signal of the γ-secretase activity is significantly improved. The more specific signal is achieved by a considerably reduced background signal and avoidance, resp., decrease of the release of the first and second partial proteins due to the action of unspecific proteases.

Figure 2:
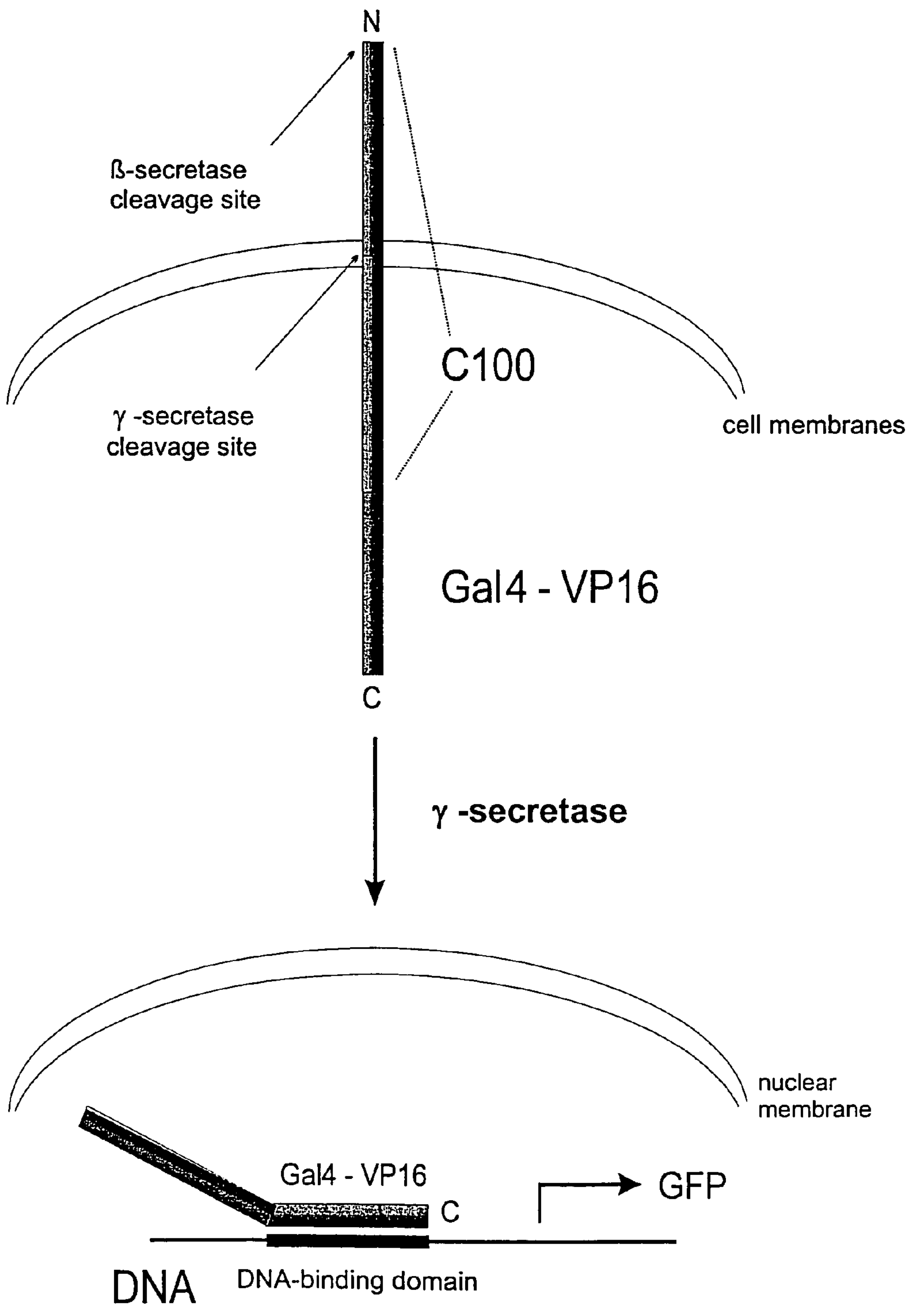
FIG. 2 shows schematically the principle on which the processes are based: β-secretase cleavage site at the N-terminus; γ-secretase cleavage site in the transmembrane domain; C100=C100 fragment of APP; GAL4-VP16=DNA-binding domain, transcription-activating domain (consisting of DNA-binding domain and transcription activator), which binds to the protein-binding domain on the DNA of the reporter plasmid.
Figure 3:
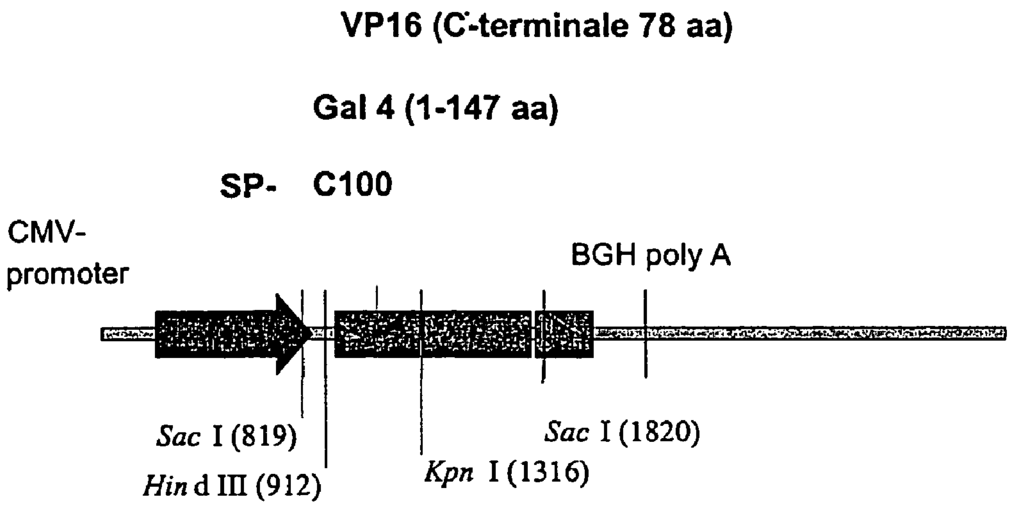
FIG. 3 shows construction of the expression plasmids SP-C100-GAL4-VP16: aa=amino acids; restriction cleavage sites Sac I, Hind III and Kpn I indicating the position of the cleavage site on the plasmid.
Figure 4:
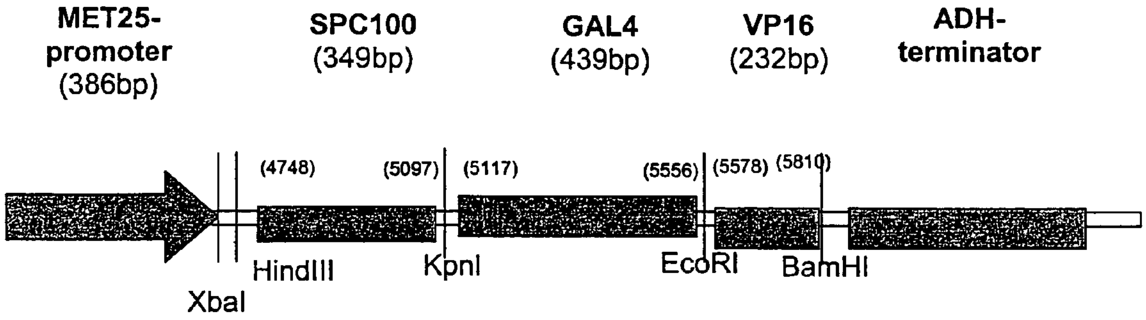
FIG. 4 shows expression plasmid pDBTrp-MET25-SP-C100-GAL4-VP16: Construction of the expression plasmid for the expression of the transgene in yeast.

An essential element of the processes according to the invention is that the C-terminal APP fragment, which is cleaved by the γ-secretase into two fragments—a first partial protein which contains the amino acid sequence GAIIGLMVGGVV (SEQ ID NO. 2) and a second partial protein which contains the amino acid sequence VIVITLVML (SEQ ID NO. 3), the second partial protein, which contains the amino acid sequence VIVITLVML (SEQ ID NO. 3), diffusing into the cytosol of the cell (FIG. 2). This second partial protein, which can be easily detected in the cytosol of a cell, e.g., as a fusion protein with a transcription activation factor (TAF) and the aid of a reporter gene; it serves as a detection tool for the presence of γ-secretase or the quantification of a γ-secretase activity. The γ-secretase cleavage site is located in the transmembrane domain of the APP (Kang, J. et al., (1987) Nature, 325, 733). The APP transmembrane domain has the amino acid sequence GAIIGLMVGGVV$_{40}$ IA$_{42}$ TVIVITLVML (SEQ ID NO. 33). The γ-secretase cleaves after $V_{40}$, $A_{42}$ or $T_{43}$. The Aβ-peptide, which is produced by eukaryotic cells in cell culture, is secreted into the medium supernatant.

With the aid of a suitable reporter system (e.g., TAF and the corresponding reporter gene), the release of the second partial protein can activate the expression of a reporter protein, which can be detected in eukaryotic cells. By means of the detection of the reporter protein, it can be demonstrated that a γ-secretase cleavage has taken place in the APP. As a result, the γ-secretase or the activity of the γ-secretase can be determined qualitatively and/or quantitatively.

The constituents of the process can be characterized in greater detail as follows:

The first nucleotide sequence codes for an amyloid precursor protein (APP) or a part thereof comprising SEQ ID NO. 1, wherein said APP or part thereof does not contain any further peptide motif acting as a signal for endo- or exocytosis and/or protease cleavage site. Preferably, said first nucleotide sequence codes for a protein which contains an amino acid sequence comprising SEQ ID NO. 1, e.g., SEQ ID NO. 6 or SEQ ID NO. 14. In further embodiments, the first nucleotide sequence codes for a truncated APP or a modified APP, e.g., obtainable by site directed mutagenesis, in order to avoid coding of a peptide motif acting as a signal for endo- or exocytosis and/or protease cleavage site beside SEQ ID NO. 1. In yet another embodiment, said APP or part thereof encoded by the said first nucleotide sequence is a protein derived from APP of human, mouse, (e.g., APLP1 or APLP2).

The second nucleotide sequence preferably codes for any suitable signal peptide ("SP"). The signal peptide contains, e.g., the SP's according to SEQ ID NO. 5 (SP of human APP), SEQ ID NO. 12 (SP of yeast SUC2, "SP2"), or SEQ ID NO. 13 (SP of BM40, "SP3") or any other signal peptide known, e.g., according to Heijne et al. (Nucl. Acids Res. (1986), 14(11) 4683-4690).

As a promoter, it is possible to use any suitable regulatable or constitutive promoter. The promoter can be suitable, e.g, for expression in mammalian cells, in *C. elegans*, in yeast, or in *Drosophila*. Suitable promoters for mammalian cells are, e.g., CMV, HSV TK, SV40, LTR (all: Clontech, Heidelberg, Germany), and RSV (e.g. Invitrogen™ life technologies, NV Leek, Netherlands). Promoters, which can be used for *C. elegans* are, e.g., unc-119, unc-54, hsp16-2, goa-1 and sel-12. For expression in yeast, the promoters ADH1 (constitutive) (Vlckova et al. (1994) Gene, 25(5), 472-4), GAL1 (conditionally inducible) (Selleck et al. (1987) Nature 325, 173-7), MET3 (conditional) (Cherest et al. (1987) Mol Gen Genet 210, 307-13) and MET25 (cf. e.g., Kerjan et al. (1986) Nucleic Acids Res. 14(20), 7861-71) are suitable. In *Drosophila*, it is possible to use, e.g., the promoters MT (metallothionine), Ac5 or Ds47 (all: Invitrogen™ life technologies).

Preferably, a eukaryotic cell is employed in the process, e.g., a human cell or a non-human cell, e.g., monkey, hamster, mouse, *Drosophila*, zebrafish or yeast. E.g., a HeLa, HEK293, H4, SH-SY5Y, H9, Cos, CHO, N2A, SL-2 or *Saccharomyces cerevisiae* cell can be employed. In a particular embodiment of the invention a *C. elegans* cell is employed. The cell can be a constituent of a transgenic, non-human animal. In a particular embodiment, the transgenic cell can be a constituent of a transgenic *C. elegans*. In particular, the invention relates to processes in which yeast cells, e.g., from the strain MaV203 (Invitrogen™ life technologies, Rockville, Md., USA) or EGY 48 (OriGene Technologies, Inc. Rockville, Md., USA), are used.

The transgene codes for a fusion protein; this is composed of the partial proteins which are encoded by the first and the second nucleotide sequence and, if appropriate, further nucleotide sequences. The fusion protein thus contains the first partial protein and the second partial protein and, if appropriate, a further partial protein. However, it is important that the fusion protein does not contain any peptide motif acting as a signal for endo- or exocytosis and/or protease cleavage site, except for SEQ ID NO. 1.

Known protease cleavage sites are known to the skilled artisan from protease databases, e.g., MEROPS (Rawlings et al. (2002) MEROPS: the protease database. Nucleic Acids Res. 30, 343-346).

Preferably, the fusion protein according to instant invention does not contain a protease cleavage site, which is a caspase cleavage site, e.g., (IVL)ExD, especially, VEVA, VEVD and in another embodiment, the fusion protein according to instant invention does further not contain a signal peptide for endo- or exocytosis, which is a signal for APP internalization, e.g., NpxY or Di-leucine especially, NPTY.

In one specific embodiment, the fusion protein has the amino acid sequence SEQ ID NO. 14. Beside SEQ. ID No. 1, said fusion protein does not contain any (one or more) further peptide motif acting as a signal for endo- or exocytosis (e.g., APP internalization signal) and/or protease (e.g., caspase) cleavage site.

In particular, a transgene having the nucleotide sequence according to SEQ ID NO. 15 (SPC55GV TAG) can be employed in the process. In particularly preferred embodiments of the process, the transgene is present in a vector. This specific embodiment of the invention is also designated as SP-C55-Gal 4-VP16 (i.e., SPC55GV). In this case, a fusion protein consisting of the signal peptide of APP, the C55 fragment of APP, GAL4 and VP16 is expressed. This protein located in the transmembrane domain is cleaved within the C55 fragment and the second partial protein, i.e. the part of the fusion protein, which contains one part of the C55 fragment, GAL4 and VP16, is detected with the aid of a reporter plasmid.

Beside the transgene construct SPC55GV, other reporter constructs are also conceivable in which, e.g., the transcription-activating domain could be inserted between the transmembrane domain and cytosolic domain of SPC55 or a Tag (e.g., MYC, FLAG) on the N- and C-terminus and between the transmembrane and the cytosolic domain of SPC55.

The further coding nucleotide sequence can code, e.g., for a protein, which can be used for the detection of the second partial protein. Preferably, the further coding nucleotide sequence is therefore located at the 3' end of the first nucleotide sequence. The further coding nucleotide sequence codes, e.g., for a chimeric protein or another protein which is constructed from a number of domains, e.g., a protein which contains a DNA-binding domain and a transcription-activating domain. In a particular embodiment of the invention, the further coding nucleotide sequence codes for a protein which consists of a GAL4-binding domain and of the transcription-activating domain of VP16 (GAL4-VP16, "GV"), and the further partial protein preferably then has the amino acid sequence SEQ ID NO. 7. In yeast cells, the further partial protein can also contain a LexA-binding domain (e.g., Lex A-VP16). This further partial protein is particularly suitable for processes in which cells of the yeast strain EGY48 are used.

In particular, the invention relates to processes in which cells are used which are co-transfected with a reporter plasmid. The reporter plasmid contains a reporter gene under the control of a regulatable promoter. E.g., the reporter gene can code for GFP and its derivatives, e.g., EGFP (Enhanced Green Fluorescent Protein), EBFP, EYFP, d2EGFP, GFPuv or Luciferase (e.g., Promega, Mannheim, Germany), CAT (e.g., Promega), SEAP (e.g., Clontech), βGal (e.g., Clontech), reef coral fluorescence protein (RCFP, Clontech) or apoptosis-inducing factors, e.g., Fas, TNF-R1, death domain and homologues (Tartaglia et al. (1993) Cell 74, 845-53), ced3, ced4, ced9. As a regulatable promoter, the reporter plasmid can contain a minimal promoter, e.g., a GAL4 binding site in combination with the minimal promoter of HIV, of the CD4 promoter or the mec7 promoter. The choice of the suitable regulatable promoter depends on the transcription-activating domain used.

A particular embodiment of the invention relates to the implementation of the process, where the cells used are yeast cells. As an alternative to the yeast expression vector pDBTrp (Invitrogen™ life technologies, The Netherlands, Cat. No. 10835023) into which in a special embodiment of the invention a MET-25 promoter is integrated (SEQ ID NO. 10), a large number of other expression vectors with different promoters (e.g., the inducible GAL1-promoter, the constitutively active ADH1 promoter) and with different selection markers (ADE, LEU, TRP, HIS, LYS, PHE) can be selected.

A particular embodiment of the invention relates to the use of yeast cells, which contain GAL4- or LexA-inducible reporter genes either stable integrated in their genome or extrachromosomal. In these embodiments preferably the yeast strains MaV203 (Invitrogen™ life technologies Inc., Rockville, Md., USA) or EGY48 (OriGene Technologies, Inc., Rockville, Md., USA) are used.

A particular embodiment of the processes relates to the use of a cell which was additionally transfected with a further recombinant vector. Preferably, the cell, which is used for these embodiments normally has no or hardly any endogenous γ-secretase or endogenous γ-secretase activity and is not detectable using the above-mentioned processes. This cell can be employed transformed with a further vector in which a nucleotide sequence—preferably a cDNA—is contained which codes for a γ-secretase, a subunit protein of γ-secretase, or a γ-secretase-like proteinase. E.g., a cDNA library can be employed. This embodiment of the process can then be used, inter alia, to identify a γ-secretase, a subunit protein of γ-secretase, or a γ-secretase-like proteinase or a cDNA, which codes for a γ-secretase, a subunit protein of γ-secretase, or a γ-secretase-like proteinase. cDNA libraries which can be searched for a γ-secretase, a subunit protein of γ-secretase, or a γ-secretase-like proteinase can be prepared from cells or tissues of any organism, e.g., B cells, neurons, glia cells, hippocampus, whole brain, placenta, kidney. Preferably, the cDNA is prepared from vertebrates (e.g., hamster, rat, mouse, dog, monkey, human), especially, from human cells or human tissues.

In the case of cells, which without transfection exhibit no γ-secretase activity, but after transfection with a cDNA library exhibit γ-secretase activity, the cDNA present in the cell codes for a γ-secretase, a subunit protein of γ-secretase, or a γ-secretase-like proteinase. This cDNA can be isolated by known processes from cells, which exhibit this behavior, and further be analyzed by known methods.

The invention also relates to a transgene, which codes for a fusion protein and contains the following constituents:

a) a first nucleotide sequence which codes for a protein which contains the amino acid sequence GAIIGLMVGGVVIATVIVITLVML (SEQ ID NO. 1),
b) at the 5' end of the first nucleotide sequence, a second nucleotide sequence which codes for a signal peptide,
c) a promoter and
d) at least one further nucleotide sequence at the 3' end of the first nucleotide sequence, which codes for a DNA-binding domain and for a transcription-activating domain, wherein beside SEQ ID NO. 1 said fusion protein does not contain one or more peptides acting as a signal for endo- or exocytosis and/or protease cleavage site.

Preferably, the first nucleotide sequence codes for APP or a part thereof, which comprises beside SEQ ID NO. 1 not any further peptide motif acting as a signal for endo- or exocytosis and/or protease cleavage site.

The transgene can, e.g., have the nucleotide sequence SEQ ID NO. 15.

The transgene can be present in a suitable vector, e.g., pcDNA 3.1+ or pDBTrp. Another embodiment of the invention is a process, which relates to the use of the transgene and/or of the vector of instant invention for the production of a transgenic cell, whereby, optionally, said transgenic cell is used to become a constituent of a non-human organism, suitable as an in vivo reporter organism. E.g., said transgene and/or vector can be used for the production of a transgenic *C. elegans*. In another embodiment, said transgene and/or the vector is used for the production of transgenic yeast cells, e.g., *S. cerevisiae.*

The invention also relates to a process for the production of a transgenic non-human organism, e.g., of a transgenic *C. elegans*, wherein said transgene and/or a vector comprising said transgene is microinjected into the gonads of the organism, e.g., of a *C. elegans*. The invention also relates to a cell, which contains a transgene according to the invention and a transgenic *C. elegans*, which contains said transgene. The invention also relates to a cell, particularly a yeast cell, which contains said transgene of the invention, preferably present in a suitable vector. Further, the invention relates in particular to cells, preferably yeast cells, which contain the transgene according to the invention and a cDNA library, resp., are suitable to be subject of a cDNA expression library (cDNA library).

The invention relates to the use of the said transgenic or recombinant cells, preferably cells of yeast or *C. elegans* in a process for the determination or identification of γ-secretase, cDNA encoding γ-secretase, cDNA encoding a subunit protein of γ-secretase, cDNA encoding a γ-secretase-like proteinase, or the activity of γ-secretase, a subunit protein of γ-secretase, or a γ-secretase-like proteinase, the use of the said cells in a process for the identification of inhibitors of the γ-secretase activity (γ-secretase, a subunit protein of γ-secretase, or a γ-secretase-like proteinase), and the process thereof.

In particular, the invention relates to processes for the identification of substances (effectors), which modulate (i.e., inhibit, decrease, increase or alter) the activity of a γ-secretase, a subunit protein of γ-secretase, or a γ-secretase-like proteinase, the process containing the following steps:

1. Production of a transgenic non-human organism, e.g., of a transgenic *C. elegans* or *Saccharomyces cerevisiae* or of a transgenic cell, the transgenic non-human organism or the transgenic cell containing the transgene according to instant invention, the transgenic non-human organism or the transgenic cell moreover containing a reporter plasmid, the reporter plasmid carrying a protein binding site, a minimal promoter and a reporter gene and, if appropriate, a cDNA which encodes the γ-secretase the subunit protein of γ-secretase, or the γ-secretase-like proteinase, wherein the transgenic non-human organism or the transgenic cell expresses the transgene and, if appropriate, the γ-secretase, a subunit protein of γ-secretase, or a γ-secretase-like proteinase encoded by the cDNA;

2. the transgenic non-human organism or the transgenic cell is incubated with a test substance to be investigated; and
3. the amount of the second partial protein is detected.

The invention also relates to a process for the identification of effectors of γ-secretase, a subunit protein of γ-secretase, or a γ-secretase-like proteinase, wherein 1. a transgene according to the invention is prepared/used;
2. the said transgene and a reporter plasmid and, if appropriate, a cDNA, which codes for a γ-secretase, a subunit protein of γ-secretase, or a γ-secretase-like proteinase are integrated into the genome of a cell and the fusion protein encoded by the said transgene and, if appropriate, the γ-secretase, subunit protein of γ-secretase, or γ-secretase-like proteinase encoded by the cDNA are expressed in the presence of a substance to be investigated;
3. the fusion protein is
   a) cleaved within the amino acid sequence SEQ ID NO. 1 by the γ-secretase present in the cell, so that
   b) a first partial protein which contains the amino acid sequence GAIIGLMVGGVV (SEQ ID NO. 2) and a second partial protein which contains the amino acid sequence VIVITLVML (SEQ ID NO. 3) are formed; and
4. said second partial protein is determined qualitatively or quantitatively.

The invention also relates to processes for the identification of substances which inhibit the activity of a γ-secretase, a subunit protein of γ-secretase, or a γ-secretase-like proteinase, where a transgene which codes for a protein which contains a signal peptide and the SEQ ID NO. 1 is expressed in the presence of a substance to be investigated and of a reporter plasmid and the effect of the substance to be investigated on the amount of second partial protein formed is determined, the second partial protein containing the amino acid sequence VIVITLVML (SEQ ID NO. 3).

The invention also relates to inhibitors of a γ-secretase, a subunit protein of γ-secretase, or a γ-secretase-like proteinase, which are identified by the processes of the invention.

Inter alia, the processes can be used, e.g., in conjunction with the C55-Gal 4-VP16 system (i.e. a fusion protein consisting of C55, GAL4 and VP16 or using a nucleic acid which codes for a corresponding fusion protein) for:

1. Identification and determination (qualitative and/or quantitative) of the activity of a γ-secretase, a subunit protein of γ-secretase, or a γ-secretase-like proteinase.
2. Identification of γ-secretases, a subunit protein of γ-secretase, or a γ-secretase-like proteinase in different tissues, cells and organisms or species. Identification and isolation of the cDNAs concerned which code for γ-secretase, a subunit protein of γ-secretase, or a γ-secretase-like proteinase and the further use of the cDNAs.
3. In vivo screening, e.g., in yeast cells (e.g., *Saccharomyces cerevisiae*), in *C. elegans* or in cell culture, enabling to determine the activity of the γ-secretase, a subunit protein of γ-secretase, or a γ-secretase-like proteinase without using immunobiological methods.
4. Use of the process of instant invention for the identification and characterization of substances, e.g., pharmacological active compounds, which modulate the enzymatic or biological activity of the γ-secretase, a subunit protein of γ-secretase, or a γ-secretase-like proteinase, e.g., effectors (inhibitors, activators, modulators) of the γ-secretase, a subunit protein of γ-secretase, or a γ-secretase-like proteinase. In particular, this process can be employed in an HTS (High Throughput Screening). By use of HTS assay systems, substances can be identified which can be employed for the treatment of Alzheimer's disease and/or for preventive treatment.
5. Investigations on or in the context of Alzheimer's disease, e.g., promoting a deeper understanding of mutated APP or fragments thereof, or the function of membrane based proteases.
6. The described fusion proteins/transgenes, e.g., C55 in SP-C55-Gal 4-VP16, can be replaced by other fragments according to the invention and the γ-secretase, a subunit protein of γ-secretase, or a γ-secretase-like proteinase, its activity and regulation can be investigated with the aid of the processes.

Another embodiment of instant invention is a pharmaceutical composition comprising a pharmaceutical active compound, which inhibits the activity of a γ-secretase, a subunit protein of γ-secretase, or a γ-secretase-like proteinase which has been identified by a process according to instant invention.

A further embodiment of instant invention is a process for preparing a pharmaceutical composition comprising a process of the invention and formulating the said identified pharmaceutical active compound.

Yet a further embodiment of instant invention is a process for preparing a pharmaceutical comprising a) a process according to the invention and b) mixing the identified pharmaceutical active compound with a pharmaceutical inert inorganic and/or organic excipients.

And still another embodiment of instant invention is a test kit for detecting the activity of γ-secretase, a subunit protein of γ-secretase, or a γ-secretase-like proteinase, comprising the transgene, vector, or cell according to instant invention.

The following examples illustrate the instant invention and are not regarded as a limitation of the inventive conception.

EXAMPLES

Example 1

Construction of the Expression Plasmid pcDNA3.1+ Comprising SP-C100-GAL4/VP16

The plasmid encodes the APP signal peptide (SP) which is fused to the C-terminal 100 amino acid residues of APP (C100). C100 begins with the N-terminus of the Aβ-peptide and ends with the C-terminus of APP. It must additionally be cleaved by the γ-secretase in order to release the Aβ-peptide.

GAL4/VP16 (Seq ID No. 7) was fused to the C-terminus of SP-C100 (Seq ID No. 6). GAL4/VP16 comprises the first 147 amino acid residues of the yeast transcription activator GAL4 and the 78 C-terminal amino acid residues of VP16, a transcription activator from the herpes simplex virus. As a fusion protein, the GAL4 fragment takes over the function of the DNA binding, while the VP16 fragment activates the transcription (Sadowski et al., 1988).

pcDNA3.1+ (Invitrogen™ life technologies, The Netherlands, Cat. No. V79020) serves as the plasmid vector.

Example 2

Construction of the Reporter Plasmid pGL2-MRG5-EGFP

The mammalian cell reporter plasmid pGL2-MRG5 is pGL2 (Promega) in which a DNA fragment from pMRG5 (Ikeda et al., 1998), comprising five GAL4 DNA-binding sites upstream of the human immunodeficiency virus (HIV) core promoter (Kretzschmar et al., 1994), is inserted upstream of the luciferase reporter gene of pGL2. For easier detection in cell culture, the luciferase reporter gene was replaced by the gene for EGFP (Enhanced Green Fluorescent Protein) obtained from the vector pEGFP-N1 (Clontech Laboratories, Heidelberg).

Example 3

Co-Transfection of Human Neuroblastoma Cells

Human neuroblastoma cells SH-SY5Y (ATCC CRL-2266) were co-transfected with both plasmids of Examples 1 and 2 and then microscopically analyzed under irradiation with light of wavelength 480 nm, by means of which EGFP is excited. It was possible to detect EGFP-expressing cells exhibiting strong green fluorescence.

In order to ensure that the green fluorescence is specifically dependent on the expression of the EGFP by the reporter plasmid, SH-SY5Y cells were transfected only with the reporter plasmid pGL2-MRG5-EGFP. In these cells, no green fluorescence was detectable. The expression was activated by GAL4-VP16, which presupposes a proteolytic release of GAL4/VP16 from the C-terminus of SP-C100-GAL4/VP16.

Example 4

Use of the C100-Gal4/VP16 System for the Detection of a cDNA Coding for a γ-Secretase Activity in cDNA Libraries SP-C100-Gal4/VP16 was cloned in the yeast expression vector pDBTrp (Invitrogen™ life technologies, The Netherlands, Cat. No. 10835023) under control of the MET25 promoter by replacing the portion of pDBTrp containing the ADH promoter and GAL4DB domains (positioned between the CYH2 gene and the multiple cloning site) with a DNA fragment containing the MET25 promoter from p415MET25 (Mumberg et al., 1994) upstream of SP-C100-Gal4-VP16. The yeast strain MaV203 (Invitrogen™ life technologies) was transformed with this construct. MaV203 is genetically modified and contains three GAL4-inducible reporter genes (URA3, HIS3, lacZ), which are stably integrated into the genome (Vidal et al., 1996). In MaV203 the proteolytic release of the GAL4/VP16 domain from SP-C100-Gal4-VP16 protein resulted in the activation of the URA3 and HIS3 read-out allowing growth on plates lacking uracil or histidine.

The expression of the SP-C100-Gal4-VP16 cDNA in MaV203 resulted in only low activity of the reporters, such that this in vivo functional assay system is suitable for screening for and detecting expression of a cDNA for a γ-secretase in a cDNA library.

Example 5

Identification of γ-Secretases by Screening of a Human B Cell cDNA Library

The recombinant MaV203 yeast strain from Example 4 was used for the purpose of screening a human B cell cDNA library (ATCC 87286; American Type Culture Collection, Manassas, Va., U.S.A.; Elledge et al., 1991) for a cDNA encoding a protein with γ-secretase activity. Alternatively, a human hippocampal cDNA library, integrated into the yeast expression vectors p415-MET25 (Mumberg et al., 1994) or p415-ADH1 (Mumberg et al., 1995), can also be employed for screening for a cDNA which codes for a γ-secretase or a protein having γ-secretase-like activity.

Example 6

Cloning of SP2-C100 and SP2-C100-GAL4/VP16

The coding region for the human signal peptide of SP-C100-GAL4/VP16 (as described in Example 1) was replaced with a signal peptide derived from the yeast SUC2 gene (SP2; SEQ ID NO. 12), resulting in a construct encoding SP2-C100-GAL4/VP16 (SEQ ID NO. 19).

SP2-C100 was constructed by amplifying the coding region of the mature form of C100 (without signal sequence, cf. SEQ ID NO. 4) with a 5'-primer, which included the coding sequence for the SUC2-signal peptide (SEQ ID NO. 12) and a 3'-primer corresponding to the natural stop codon (Kang et al., (1987)). In order to facilitate the exchange of the signal peptide, the primers EH47 (SEQ ID NO. 23) and EH49 (SEQ ID NO. 24) were designed so that the resulting PCR product contained an additional NheI site joining the coding regions for the signal peptide and the mature peptide.

```
EH47:
5'-GCTCTAGAATGCTTTTGCAAGCTTTCCTTTTCCTTTTGGCT

GGTTTTGCAGCC AAAATATCTGCAGCGCTAGCTGATGCAGAAT

TCCGACATGAC-3'

EH49:
5'-CGGGATCCCTAGGCGCCGTTCTGCATCTGCTCAAAGAAC-3'
```

The SP2-C100-GAL4/VP16 was obtained by EcoRI cleavage to excise the C100 fragment of SP2-C100 and replace it with C100-GAL4/VP16.

The fragments were cloned into the yeast expression vector pDBTrp (Invitrogen™ life technologies, The Netherlands, Cat. No. 10835023) containing the MET25 promoter, as described in Example 4.

Example 7

Cloning of SP2-C-GAL4/VP16-100

To obtain the construct SP2-C-GAL4/VP16-100 (SEQ ID NO. 17), three independent PCR reactions were performed by use of the following primers:

EH53:
5'-ACTATATCTAGAATGCTTTTGC-3'

EH54:
5'-TTCGATAGAAGACAGTAGCTTGCCAGATCTACCTTTCTTCTTCAGCA

TCACCAA-3'

EH55:
5'-TTGGTGATGCTGAAGAAGAAAGGTAGATCTGGCAAGCTACTGTCTTC

TATCGAA-3'

EH56:
5'-ATGATGAATGGATGTGTACTGGCCACTAGTACCCCCACCGTACTCGT

CAATT-3'

EH57:
5'-AATTGACGAGTACGGTGGGGGTACTAGTGGCCAGTACACATCCATTC

ATCAT-3'

EH59:
5'-CGATAAGCTTGATATCGAATTC-3':

1) Using SP2-C100 as a template, the ectodomain and the transmembrane domain of C100 were amplified by use of primers EH53 (SEQ ID NO. 25) and EH54 (SEQ ID NO. 26) in such a way that the PCR product contained also the 3'-flanking region, which overlaps with the GAL4/VP16 coding region.

2) Using primers EH55 (SEQ ID NO. 27) and EH56 (SEQ ID NO. 28), and GAL4/VP16 as the DNA template, a PCR reaction was performed to amplify the coding region with 5'- and 3'-flanking regions corresponding to each side of SP2-C100.

3) The 3'-segment of SP2-C100 that encodes the cytoplasmic domain of C100 was amplified by use of primers EH57 (SEQ ID NO. 29) and EH 59 (SEQ ID NO. 30), resulting in a 5'-overlap with the GAL4/VP16 coding region. The resulting PCR products (of about 200 bp, 720 bp, and 100 bp) were purified and used for a final PCR in the presence of EH53 and EH59, corresponding to the 5'- and 3'-ends of SP2-C100. The final PCR product of about 1000 bp was cloned into a yeast expression vector derived from pDBTrp (Invitrogen™ life technologies, The Netherlands, Cat. No. 10835023) containing the MET25 promoter, as described in Example 4.

Example 8

Cloning of SP3-C100, SP3-C100-GAL4/VP16, and SP3-C-GAL4/VP16-100

To create the three plasmid vectors for expression of SP3-C100, SP3-C100-GAL4/VP16 (SEQ ID No. 21), and SP3-C-GAL4/VP16-100 (SEQ ID NO. 32) in mammalian cell systems, either C100, C100-GAL4/VP16 or C-GAL4/VP16-100 were sub-cloned from the yeast expression vectors of Example 6 or 7 into the mammalian expression vector pRc/CMV (Invitrogen, Cat. No. V75020), which contains the coding region for the BM40 signal peptide (SP3; SEQ ID NO. 13). The coding regions of the C100, C100-GAL4/VP16 or C-GAL4/VP16-100 were ligated in frame to the SP3 coding region at the unique NheI restriction site described in Example 6.

Example 9

Improving the Expression of C100-GAL4/VP16 in Yeast

Quantification of the expression level of different constructs in crude lysates from transformed yeast revealed that the expression of SP-C100-GAL4/VP16 was very low, compared with lysates from yeast cells transformed with vectors encoding fusions with the yeast SUC2 signal peptide. For example, expression of SP2-C100-GAL4/VP16 resulted in the strong expression of a specific band of the expected size. However, also bands with higher electrophoretic mobility could be detected by immunoblotting, indicating non-specific degradation of the recombinant protein in yeast. The stability of the protein was improved in the case of C-GAL4/VP16-100 (see below) in which the GAL4/VP16 domain was inserted in-frame into C100, close to the γ-secretase cleavage site. Both fusion proteins gave expression levels comparable to the construct encoding C100 without GAL4/VP16, indicating that the two different fusions between C100 and GAL4/VP16 did not interfere with protein expression.

Example 10

Improving the Background in Yeast

The increased expression of C100-GAL4/VP16 due to the exchange of the signal peptides correlated with a strong increase in non-specific activation of the URA3, HIS3, and lacZ reporter systems in the yeast strain MaV203. Since yeast lacks γ-secretase activity, this was most likely due to non-specific processing of C100-GAL4/VP16 by cellular proteases and the release of active GAL4/VP16.

By moving the GAL4/VP16 domain closer to the γ-secretase cleavage site the non-specific proteolytic cleavage detected with C100-GAL4/VP16 at sites between the transmembrane domain of C100 and the amino terminal end of the GAL4/VP16 domain was essentially eliminated.

Cleavage of the various constructs was tested in MaV203 by examining GAL4/VP16-dependent activation of the reporter systems.

Transformation of MaV203 with SP-C100-GAL4/VP16 exhibited a $Ura^+$, $His^-$ phenotype (cf. Example 4). Increasing the expression levels by replacing the SP signal peptide with the SP2 peptide (to give SP2-C100-GAL4/VP16) resulted in a strong activation of all read-outs to a level similar to that detected in the positive control, MaV203 constitutively expressing full-length GAL4 protein (encoded by plasmid pCL1; Clontech Laboratories).

In contrast, MaV203 cells expressing SP2-C-GAL4/VP16-100, which is expressed at levels comparable to SP2-C100-GAL4/VP16, exhibited a $Ura^-$-, $His^-$-phenotype, as was exhibited also by MaV203 transformed with an empty vector control.

Therefore, SP2-C-GAL4/VP16-100 can be highly expressed in yeast, but still display very low non-specific activation of the GAL4-dependent reporters. High-level expression of the SP2-C-GAL4/VP16-100 protein, combined with a low background of non-specific cleavage/reporter activation, is a prerequisite for a read-out system with a surprisingly optimized signal-to-noise ratio.

Example 11

Processing of SP3-C-GAL4/VP16-100 by γ-Secretase in Mammalian Cells

To demonstrate that SP3-C-GAL4/VP16-100 protein expressed in mammalian cells is processed correctly by γ-secretase activity, SP3-C-GAL4/VP16-100 was transfected into mammalian cells that have been shown to express γ-secretase activity endogenously (Haass et al., 1992). For expression in mammalian cells, the signal peptide in SP2-C-GAL4/VP16-100 was replaced, as described in Example 8, with a mammalian signal peptide derived from the basal membrane protein BM40, which is known for high level expression (SP3; SEQ ID NO. 13). Processing of γ-secretase was monitored by quantifying the secretion of Aβ into the culture medium. The secreted Aβ was detected by a sandwich ELISA using monoclonal antibodies 6E10 and biotinylated 4G8 (Senetek PLC, Napa, Calif., USA; cf. Kim et al., 1990) as capture and detection antibodies, respectively.

After transfection with SP3-C100 an eight-fold increase in Aβ secretion was observed in comparison to the empty vector control. Cells transfected with SP3-C100-GAL4/VP16 or SP3-C-GAL4/VP16-100 secreted similar amounts of Aβ, indicating that neither the C-terminal nor the juxtamembrane fusion of GAL4/VP16 interferes with proteolytic processing by γ-secretase.

Example 12

Transcriptional Activation of GAL4/VP16-Dependent Reporter Gene by C-Gal4/VP16-100 Expressed in Mammalian Cells Processing of C100-GAL4/VP16 and C-GAL4/VP16-100 by γ-secretase results in the release of a polypeptide containing GAL4/VP16 and additional amino acids from flanking portions of C100. SP3-C100-GAL4/VP16 and SP3-C-GAL4/VP16-100 were co-transfected with the mammalian reporter-plasmid pGL2-MRG5-EGFP (Ikeda et al., 1998) described in Example 2, which contains five GAL4 DNA-binding sites upstream of the human immunodeficiency virus (HIV) core promoter and the cDNA encoding EGFP. The co-transfection of pGL2-MRG5-EGFP with the GAL4/VP16-containing fusions resulted in the appearance of GFP-positive cells in both cases.

Example 13

Construction of the Mammalian Expression Plasmid SP3-C55-GAL4/VP16

Constructs containing the C100 sequence of APP and GAL4/VP16 contain both the cleavage site of γ-secretase and a cleavage site of caspase-like proteases. To avoid that an unspecific caspase-like activity could cleave SP3-C100-GAL4/VP16 between the authentic γ-secretase site and the GAL4/VP16 domain to release GAL4/VP16 and activate the reporter system in mammalian cells, the 45 amino acid C-terminal segment of C100 contained in SP3-C100-GAL4/VP16, encoding the cytoplasmic domain of APP, was deleted. Removal of the C-terminal 45 amino acids of C100 also eliminates an "internalization signal" peptide at the C-terminus of APP that directs the endocytosis of APP after being inserted in the plasma membrane.

Thus, the mammalian expression plasmid SP3-C55-GAL4/VP16 comprises the BM40 signal peptide (Seq ID No. 13), the N-terminal 55 amino acid residues (C55; Seq ID No. 6) of APP-C100, and GAL4/VP16. C55 begins with the N-terminus of the Aβ-peptide and ends with the transmembrane domain of APP. In SP3-C55-GAL4/VP16 protein, only the cleavage site for γ-secretase is present. C55 comprises the γ-secretase cleavage site and must be cleaved by γ-secretase in order to release the Aβ-peptide and GAL4/VP16. Moreover, because the endocytic internalization signal peptide is not present in SP3-C55-GAL4/VP16, only γ-secretase catalyzing cleavage of plasma membrane-associated C55-GAL4/VP16 will release Aβ-peptide and activate GAL4/VP16-dependent transcription of the reporter system.

The expression plasmid was derived from the vector SP3-C-GAL4/VP16-100 by the introduction of a stop codon (TAG) after the GAL4/VP16 sequence.

This was performed by replacing the HpaI-ClaI fragment of SP3-C-GAL4/VP16-100 with a DNA fragment generated by PCR using SP3-C-GAL4/VP16-100 as the DNA template, a 5'-primer upstream of the unique the HpaI site in GAL4/VP16, and a 3'-primer (5'-CCATCGATTTTCTAACCCCCACCGTA-3'; Seq ID No. 31) that introduces a TAG stop codon (underlined) and a ClaI restriction site at the C-terminus of the GAL4/VP16 opening reading frame.

Example 14

Stable Transfected HEK293 Cells

HEK293 cells (Human Embryonic Kidney cell line, (ATCC)) were co-transfected with the plasmid SP3-C55-GAL4/VP16 and the luciferase reporter plasmid PGL2-MRG5(described in Example 2).

Subsequently, stable cell lines were selected by incubation with 400 μg/ml Geneticin (GibcoBRL) to select for Neomycin resistant clones and thereafter characterized for stable expression of SP3-C55-GAL4/VP16 and luciferase.

Example 15

Transient Transfection of HEK 293 Cells

HEK293 cells were co-transfected with the SP3-C55-GAL4/VP16 vector (0.03 μg) and the pGL2-MRG5 luciferase reporter vector (1 μg) in Multi-Well 12 plates.

The compounds DPAT (from Elan Pharmaceuticals; Dovey et al., 2001) and L-685,458 (from Merck Pharmaceuticals; Shearman et al., 2000), both known γ-secretase inhibitors, inhibited dose-dependently luciferase activity and Aβ-production, and exhibited an $IC_{50}$ of 14 nM (DAPT) and 19 nM (L-685,458), respectively.

Luciferase activity was quantified by the Bright-Glo Luciferase Assay kit (Promega). Aβ in the cell medium was quantified by ELISA, using the antibodies 4G8 and 6E10 (from Senetek), as described in Example 11. These antibodies are specific for amino acids 17-24 (4G8) and 1-17 (6E10) of the Aβ-peptide.

In transient transfection experiments, Aβ was also identified by immunoprecipitation and by immunoblotting. Both methods identified a 4 kDa band corresponding to Aβ-peptide.

Example 16

Pharmacological Characterization of the Stable Transfected HEK293 Cells

A clone of HEK293 cells that stably express both the SP3-C55-GAL4/VP16 and the MRG5-luciferase constructs was identified according to Example 14. This cell clone was used to examine the response of the stably γ-transfected mammalian cell assay system to DAPT (from Elan Pharm.; Dovey et al., 2001), and L-685,458 (from Merck Pharm.; Shearman et al., 2000)., Both compounds exhibited dose-dependent inhibition of luciferase activity (24 h treatment) with an $IC_{50}$ of 230 nM (DAPT) and 130 nM (L-685,458), respectively.

Example 17

Identification of Inhibitors of γ-Secretase

For the identification of γ-secretase inhibitors, stably double-transfected HEK293 cells (see Example 14) are incubated, in Multi-Well 96 plates, in the presence of the compound(s) under investigation (e.g., compound library screening) at a concentration 10 μM or less in the assay, and luciferase activity is determined 24 hours later. Luciferase activity can be quantified with the Luciferase Assay System kit (Promega), the Bright-Glo Luciferase Assay kit (Promega), or any other method for luciferase quantification. A decrease in luciferase activity reflects a decrease in γ-secretase activity.

REFERENCES

Dovey et al. (2001) J. Neurochem. 76, 173.
Elledge et al. (1991) Proc. Natl. Acad. Sci. USA 88, 1731.
Estus et al. (1992) Science 255, 726.
Haass et al. (1992) Nature 359, 322.
Heijne et al. (1986) Nucl. Acids Res. 14(11), 4683-4690.
Hilbich et al. (1991) J. Mol. Biol. 218, 149.
Ikeda et al. (1998) Mol. Cell. Biol. 18, 10.
Kang et al. (1987) Nature 325, 733.
Kim et al. (1990) Neurosci. Res. Comm. 7, 113.
Kretzschmar et al. (1994) Mol. Cell. Biol. 14, 3927.
Maruyama et al. (1994) Biochem. Biophys. Res. Commun. 202, 1517.
Mattson (2003) Nature 422, 385.
Mumberg et al. (1994) Nucl. Acids Res. 22, 5767.
Mumberg et al. (1995) Gene 156, 119.
Rumble et al. (1989), N. Engl. J. Med. 320, 1446.
Sadowski et al. (1988) Nature 335, 563.
Scheuner et al. (1996), Nature Medicine 2, 864.
Shearman et al. (2000) Biochemistry 39, 8698.
Simons et al. (1996) J. Neurosci. 16(3), 899-908.
Suzuki et al. (1994) Science 264(5163), 1336-1340.
Vidal et al. (1996) Proc. Natl. Acad. Sci. USA 93, 10315.
Yankner et al. (1990) Proc. Natl. Acad. Sci. USA 87, 9020.

For General Recombinant DNA Work:
Sambrook, J., Fritsch, E. F., and Maniatis, T. (1989) Molecular Cloning: A Laboratory Manual, 2nd Ed., Cold Spring Harbor Laboratory, Cold Spring Harbor, N.Y.

For Yeast Work (DNA Transformation):
Ausubel, F. M., Brent, R., Kingston, R. E., Moore, D. D., Seidman, J. G., Smith, J. A., and Struhl, K. (1994) Current Protocols in Molecular Biology, pp. 13.7.1-13.7.2, Greene Publishing Associates/Wiley-Interscience, New York For *C. elegans* Work (Transgenics):
Mello, C. and Fire, A. (1995) DNA transformation. In: Epstein, H. F. and Shakes, D. C., ed. *Caenorhabditis elegans*: Modern Biological Analysis of an Organism. Methods in Cell Biology, Vol. 48. Academic Press, San Diego, Calif., pp. 451-482.

```
SEQ ID No. 1 (APP fragment)
GAIIGLMVGGVVIATVIVITLVML

SEQ ID No. 2 (APP fragment (First partial protein))
GAIIGLMVGGVV

SEQ ID No. 3 (APP fragment (Second partial protein))
VIVITLVML

SEQ ID No. 4 (C100 fragment)
LDAEFRHDSG YEVHHQKLVF FAEDVGSNKG AIIGLMVGGV VIATVIVTTL

VMLKKKQYTS IHHGVVEVDA AVTPEERHLS KMQQNGYENP TYKFFEQMQN

SEQ ID No. 5 (Signal peptide of human APP (SP))
MLPGLALFLL AAWTARA

SEQ ID No. 6 (C55 fragment)
LDA EFRHDSGYEV HHQKLVFFAE DVGSNKGAII

GLMVGGVVIA TVIVITLVML KK

SEQ ID No. 7 (GAL4-VP1G)
MKLLSSIEQA CDICRLKKLK CSKEKPKCAK CLKNNWECRY SPKTKRSPLT

RAHLTEVESR LERLEQLFLL IFPREDLDMI LKMDSLQDIK ALLTGLFVQD

NVNKDAVTDR LASVETDMPL TLRQHRISAT SSSEESSNKG QRQLTVSPEF

PGIWAPPTDV SLGDELHLDG EDVAMAHADA LDDFDLDMLG DGDSPGPGFT

SEQ ID No. 8 (SP-C100-GAL4-VP16)
GGCAAGGCTTGACCGACAATTGCATGAAGAATCTGCTTAGGGTTAGGCGTTTTGCGCTGCTTCG

CGATGTAC

GGGCCAGATATACGCGTTGACATTGATTATTGACTAGTTATTAATAGTAATCAATTACGGGGTC
```

-continued

ATTAGTTC

ATAGCCCATATATGGAGTTCCGCGTTACATAACTTACGGTAAATGGCCCGCCTGGCTGACCGCC

CAACGACC

CCCGCCCATTGACGTCAATAATGACGTATGTTCCCATAGTAACGCCAATAGGGACTTTCCATTG

ACGTCAAT

GGGTGGACTATTTACGGTAAACTGCCCACTTGGCAGTACATCAAGTGTATCATATGCCAAGTAC

GCCCCCTA

TTGACGTCAATGACGGTAAATGGCCCGCCTGGCATTATGCCCAGTACATGACCTTATGGGACTT

TCCTACTT

GGCAGTACATCTACGTATTAGTCATCGCTATTACCATGGTGATGCGGTTTTGGCAGTACATCAA

TGGGCGTG

GATAGCGGTTTGACTCACGGGGATTTCCAAGTCTCCACCCCATTGACGTCAATGGGAGTTTGTT

TTGGCACC

GCGTGTACGGTGGGAGGTCTATATAAGCAGAGCTCTCTGGCTAACTAGAGAACCCACTGCTTAC

TGGCTTATCGAAATTAATACGACTCACTATAGGGAGACCCAAGCTGGCTAGCGTTTAAACTTAA

GCTTCACAGCTAGCGCA

CTCGGTGCCCCGCGCAGGGTCGCGATGCTGCCCGGTTTGGCACTGTTCCTGCTGGCCGCCTGGA

CGGCTCGGGCGCTGGATGCAGAATTCCGACATGACTCAGGATATGAAGTTCATCATCAAAAATT

GGTGTTCTTTGCAGAAGATGTGGGTTCAAACAAAGGTGCAATCATTGGACTCATGGTGGGCGGT

GTTGTCATAGCGACAGTGATCGTCATCACCTTGGTGATGCTGAAGAAGAAACAGTACACATCCA

TTCATCATGGTGTGGTGGAGGTTGACGCCGCTGTCACCCCAGAGGAGCGCCACCTGTCCAAGAT

GCAGCAGAACGGCTACGAAAATCCAACCTACAAGTTCTTTGAGCAGATGCAGAACGCGCGGGGT

ACCCCGGCG ATGAAGC TACTGTCTTC TATCGAACAA GCATGCGATA TTTGCCGACT

TAAAAAGCTC AAGTGCTCCA AAGAAAAACC GAAGTGCGCC AAGTGTCTGA

AGAACAACTG GGAGTGTCGC TACTCTCCCA AAACCAAAAG GTCTCCGCTG

ACTAGGGCAC ATCTGACAGA AGTGGAATCA AGGCTAGAAA GACTGGAACA

GCTATTTCTA CTGATTTTTC CTCGAGAAGA CCTTGACATG ATTTTGAAAA

TGGATTCTTT ACAGGATATA AAAGCATTGT TAACAGGATT ATTTGTACAA

GATAATGTGA ATAAAGATGC CGTCACAGAT AGATTGGCTT CAGTGGAGAC

TGATATGCCT CTAACATTGA GACAGCATAG AATAAGTGCG ACATCATCAT

CGGAAGAGAG TAGTAACAAA GGTCAAAGAC AGTTGACTGT ATCG

CCGGAATTCCCGGGGATCTGGGC CCCCCCGAC CGATGTCAGC CTGGGGGACG

AGCTCCACTT AGACGGCGAG GACGTGGCGA TGGCGCATGC CGACGCGCTA

GACGATTTCG ATCTGGACAT GTTGGGGGAC GGGGATTCCC CGGGGCCGGG

ATTTACCCCC CACGACTCCG CCCCCTACGG CGCTCTGGAT ATGGCCGACT

TCGAGTTTGA GCAGATGTTT ACCGATGCCC TTGGAATTGA CGAGTACGGT GGGTAG

SEQ ID No. 9 (Human APP)
AGTTTCCTCG GCAGCGGTAG GCGAGAGCAC GCGGAGGAGC GTGCGCGGGG GCCCCGGGAG

ACGGCGGCGG TGGCGGCGCG GGCAGAGCAA GGACGCGGCG GATCCCACTC GCACAGCAGC

GCACTCGGTG CCCCGCGCAG GGTCGCGATG CTGCCCGGTT TGGCACTGCT CCTGCTGGCC

GCCTGGACGG CTCGGGCGCT GGAGGTACCC ACTGATGGTA ATGCTGGCCT

-continued

GCTGGCTGAA

CCCCAGATTG CCATGTTCTG TGGCAGACTG AACATGCACA TGAATGTCCA GAATGGGAAG

TGGGATTCAG ATCCATCAGG GACCAAAACC TGCATTGATA CCAAGGAAGG CATCCTGCAG

TATTGCCAAG AAGTCTACCC TGAACTGCAG ATCACCAATG TGGTAGAAGC CAACCAACCA

GTGACCATCC AGAACTGGTG CAAGCGGGGC CGCAAGCAGT GCAAGACCCA TCCCCACTTT

GTGATTCCCT ACCGCTGCTT AGTTGGTGAG TTTGTAAGTG ATGCCCTTCT CGTTCCTGAC

AAGTGCAAAT TCTTACACCA GGAGAGGATG GATGTTTGCG AAACTCATCT TCACTGGCAC

ACCGTCGCCA AAGAGACATG CAGTGAGAAG AGTACCAACT TGCATGACTA CGGCATGTTG

CTGCCCTGCG GAATTGACAA GTTCCGAGGG GTAGAGTTTG TGTGTTGCCC ACTGGCTGAA

GAAAGTGACA ATGTGGATTC TGCTGATGCG GAGGAGGATG ACTCGGATGT CTGGTGGGGC

GGAGCAGACA CAGACTATGC AGATGGGAGT GAAGACAAAG TAGTAGAAGT AGCAGAGGAG

GAAGAAGTGG CTGAGGTGGA AGAAGAAGAA GCCGATGATG ACGAGGACGA TGAGGATGGT

GATGAGGTAG AGGAAGAGGC TGAGGAACCC TACGAAGAAG CCACAGAGAG AACCACCAGC

ATTGCCACCA CCACCACCAC CACCACAGAG TCTGTGGAAG AGGTGGTTCG AGTTCCTACA

ACAGCAGCCA GTACCCCTGA TGCCGTTGAC AAGTATCTCG AGACACCTGG GGATGAGAAT

GAACATGCCC ATTTCCAGAA AGCCAAAGAG AGGCTTGAGG CCAAGCACCG AGAGAGAATG

TCCCAGGTCA TGAGAGAATG GGAAGAGGCA GAACGTCAAG CAAAGAACTT GCCTAAAGCT

GATAAGAAGG CAGTTATCCA GCATTTCCAG GAGAAAGTGG AATCTTTGGA ACAGGAAGCA

GCCAACGAGA GACAGCAGCT GGTGGAGACA CACATGGCCA GAGTGGAAGC CATGCTCAAT

GACCGCCGCC GCCTGGCCCT GGAGAACTAC ATCACCGCTC TGCAGGCTGT TCCTCCTCGG

CCTCGTCACG TGTTCAATAT GCTAAAGAAG TATGTCCGCG CAGAACAGAA GGACAGACAG

CACACCCTAA AGCATTTCGA GCATGTGCGC ATGGTGGATC CCAAGAAAGC CGCTCAGATC

CGGTCCCAGG TTATGACACA CCTCCGTGTG ATTTATGAGC GCATGAATCA GTCTCTCTCC

CTGCTCTACA ACGTGCCTGC AGTGGCCGAG GAGATTCAGG ATGAAGTTGA TGAGCTGCTT

CAGAAAGAGC AAAACTATTC AGATGACGTC TTGGCCAACA TGATTAGTGA ACCAAGGATC

AGTTACGGAA ACGATGCTCT CATGCCATCT TTGACCGAAA CGAAAACCAC CGTGGAGCTC

CTTCCCGTGA ATGGAGAGTT CAGCCTGGAC GATCTCCAGC CGTGGCATTC TTTTGGGGCT

GACTCTGTGC CAGCCAACAC AGAAAACGAA GTTGAGCCTG TTGATGCCCG CCCTGCTGCC

GACCGAGGAC TGACCACTCG ACCAGGTTCT GGGTTGACAA ATATCAAGAC GGAGGAGATC

TCTGAAGTGA AGATGGATGC AGAATTCCGA CATGACTCAG GATATGAAGT TCATCATCAA

AAATTGGTGT TCTTTGCAGA AGATGTGGGT TCAAACAAAG GTGCAATCAT TGGACTCATG

GTGGGCGGTG TTGTCATAGC GACAGTGATC GTCATCACCT TGGTGATGCT GAAGAAGAAA

CAGTACACAT CCATTCATCA TGGTGTGGTG GAGGTTGACG CCGCTGTCAC CCCAGAGGAG

CGCCACCTGT CCAAGATGCA GCAGAACGGC TACGAAAATC CAACCTACAA GTTCTTTGAG

CAGATGCAGA ACTAGACCCC CGCCACAGCA GCCTCTGAAG TTGGACAGCA AAACCATTGC

TTCACTACCC ATCGGTGTCC ATTTATAGAA TAATGTGGGA AGAAACAAAC CCGTTTTATG

ATTTACTCAT TATCGCCTTT TGACAGCTGT GCTGTAACAC AAGTAGATGC CTGAACTTGA

ATTAATCCAC ACATCAGTAA TGTATTCTAT CTCTCTTTAC ATTTTGGTCT CTATACTACA

TTATTAATGG GTTTTGTGTA CTGTAAAGAA TTTAGCTGTA TCAAACTAGT GCATGAATAG

ATTCTCTCCT GATTATTTAT CACATAGCCC CTTAGCCAGT TGTATATTAT TCTTGTGGTT

-continued

TGTGACCCAA TTAAGTCCTA CTTTACATAT GCTTTAAGAA TCGATGGGGG ATGCTTCATG

TGAACGTGGG AGTTCAGCTG CTTCTCTTGC CTAAGTATTC CTTTCCTGAT CACTATGCAT

TTTAAAGTTA AACATTTTTA AGTATTTCAG ATGCTTTAGA GAGATTTTTT TTCCATGACT

GCATTTTACT GTACAGATTG CTGCTTCTGC TATATTTGTG ATATAGGAAT TAAGAGGATA

CACACGTTTG TTTCTTCGTG CCTGTTTTAT GTGCACACAT TAGGCATTGA GACTTCAAGC

TTTTCTTTTT TTGTCCACGT ATCTTTGGGT CTTTGATAAA GAAAAGAATC CCTGTTCATT

GTAAGCACTT TTACGGGGCG GGTGGGGAGG GGTGCTCTGC TGGTCTTCAA TTACCAAGAA

TTCTCCAAAA CAATTTTCTG CAGGATGATT GTACAGAATC ATTGCTTATG ACATGATCGC

TTTCTACACT GTATTACATA AATAAATTAA ATAAAATAAC CCCGGGCAAG ACTTTTCTTT

GAAGGATGAC TACAGACATT AAATAATCGA AGTAATTTTG GGTGGGGAGA AGAGGCAGAT

TCAATTTTCT TTAACCAGTC TGAAGTTTCA TTTATGATAC AAAAGAAGAT GAAAATGGAA

GTGGCAATAT AAGGGGATGA GGAAGGCATG CCTGGACAAA CCCTTCTTTT AAGATGTGTC

TTCAATTTGT ATAAAATGGT GTTTTCATGT AAATAAATAC ATTCTTGGAG GAGC

SEQ ID No. 10 (Recombinant plasmid pDBTrp-MET25-SP-C100-GAL4-VP16)
ACGAAAGGGCCTCGTGATACGCCTATTTTTATAGGTTAATGTCATGATAATAATGGTTTCTTAG

GACGGATCGCTTGCCTGTAACTTACACGCGCCTCGTATCTTTTAATGATGGAATAATTTGGGAA

TTTACTCTGTGTTTATTTATTTTTATGTTTTGTATTTGGATTTTAGAAAGTAAATAAAGAAGGT

AGAAGAGTTACGGAATGAAGAAAAAAAAATAAACAAAGGTTTAAAAAATTTCAACAAAAAGCGT

ACTTTACATATATATTTATTAGACAAGAAAAGCAGATTAAATAGATATACATTCGATTAACGAT

AAGTAAAATGTAAAATCACAGGATTTTCGTGTGTGGTCTTCTACACAGACAAGATGAAACAATT

CGGCATTAATACCTGAGAGCAGGAAGAGCAAGATAAAAGGTAGTATTTGTTGGCGATCCCCCTA

GAGTCTTTTACATCTTCGGAAAACAAAAACTATTTTTTCTTTAATTTCTTTTTTTACTTTCTAT

TTTTAATTTATATATTTATATTAAAAAATTTAAATTATAATTATTTTTATAGCACGTGATGAAA

AGGACCCAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATCTGCAGCT

CTGGCCCGTGTCTCAAAATCTCTGATGTTACATTGCACAAGATAAAAATATATCATCATGAACA

ATAAAACTGTCTGCTTACATAAACAGTAATACAAGGGGTGTTATGAGCCATATTCAACGGGAAA

CGTCTTGCTGGAGGCCGCGATTAAATTCCAACATGGATGCTGATTTATATGGGTATAAATGGGC

TCGCGATAATGTCGGGCAATCAGGTGCGACAATCTTTCGATTGTATGGGAAGCCCGATGCGCCA

GAGTTGTTTCTGAAACATGGCAAAGGTAGCGTTGCCAATGATGTTACAGATGAGATGGTCAGAC

TAAACTGGCTGACGGAATTTATGCCTCTTCCGACCATCAAGCATTTTATCCGTACTCCTGATGA

TGCATGGTTACTCACCACTGCGATCCGCGGGAAAACAGCATTCCAGGTATTAGAAGAATATCCT

GATTCAGGTGAAAATATTGTTGATGCGCTGGCAGTGTTCCTGCGCCGGTTGCATTCGATTCCTG

TTTGTAATTGTCCTTTTAACAGCGATCGCGTATTTCGTCTCGCTCAGGCGCAATCACGAATGAA

TAACGGTTTGGTTGATGCGAGTGATTTTGATGACGAGCGTAATGGCTGGCCTGTTGAACAAGTC

TGGAAAGAAATGCATACGCTTTTGCCATTCTCACCGGATTCAGTCGTCACTCATGGTGATTTCT

CACTTGATAACCTTATTTTTGACGAGGGGAAATTAATAGGTTGTATTGATGTTGGACGAGTCGG

AATCGCAGACCGATACCAGGATCTTGCCATCCTATGGAACTGCCTCGGTGAGTTTTCTCCTTCA

TTACAGAAACGGCTTTTTCAAAAATATGGTATTGATAATCCTGATATGAATAAATTGCAGTTTC

ATTTGATGCTCGATGAGTTTTTCTAATCAGAATTGGTTAATTGGTTGTAACACTGGCAGAGCAT

-continued

TACGCTGACTTGACGGGACGGCGCATGACCAAAATCCCTTAACGTGAGTTTTCGTTCCACTGAG

CGTCAGACCCCGTAGAAAAGATCAAAGGATCTTCTTGAGATCCTTTTTTTCTGCGCGTAATCTG

CTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTCCTTCTAGTGT

AGCCGTAGTTAGGCCACCACTTCAAGAACTCTGTAGCACCGCCTACATACCTCGCTCTGCTAAT

CCTGTTACCAGTGGCTGCTGCCAGTGGCGATAAGTCGTGTCTTACCGGGTTGGACTCAAGACGA

TAGTTACCGGATAAGGCGCAGCGGTCGGGCTGAACGGGGGGTTCGTGCACACAGCCCAGCTTGG

AGCGAACGACCTACACCGAACTGAGATACCTACAGCGTGAGCATTGAGAAAGCGCCACGCTTCC

CGAAGGGAGAAAGGCGGACAGGTATCCGGTAAGCGGCAGGGTCGGAACAGGAGAGCGCACGAGG

GAGCTTCCAGGGGGGAACGCCTGGTATCTTTATAGTCCTGTCGGGTTTCGCCACCTCTGACTTG

AGCGTCGATTTTTGTGATGCTCGTCAGGGGGGCCGAGCCTATGGAAAAACGCCAGCAACGCGGC

CTTTTTACGGTTCCTGGCCTTTTGCTGGCCTTTTGCTCACATGTTCTTTCCTGCGTTATCCCCT

GATTCTGTGGATAACCGTATTACCGCCTTTGAGTGAGCTGATACCGCTCGCCGCAGCCGAACGA

CCGAGCGCAGCGAGTCAGTGAGCGAGGAAGCGGAAGAGCGCCCAATACGCAAACCGCCTCTCCC

CGCGCGTTGGCCGATTCATTAATGCAGCTGGCACGACAGGTTTCCCGACTGGAAAGCGGGCAGT

GAGCGCAACGCAATTAATGTGAGTTACCTCACTCATTAGGCACCCCAGGCTTTACACTTTATGC

TTCCGGCTCCTATGTTGTGTGGAATTGTGAGCGGATAACAATTTCACACAGGAAACAGCTATGA

CCATGATTACGCCAAGCTCGGAATTAACCCTCACTAAAGGGAACAAAAGCTGGTACCGATCCCG

AGCTTTGCAAATTAAAGCCTTCGAGCGTCCCAAAACCTTCTCAAGCAAGGTTTTCAGTATAATG

TTACATGCGTACACGCGTCTGTACAGAAAAAAAAGAAAAATTTGAAATATAAATAACGTTCTTA

ATACTAACATAACTATAAAAAAATAAATAGGGACCTAGACTTCAGGTTGTCTAACTCCTTCCTT

TTCGGTTAGAGCGGATGTGGGGGGAGGGCGTGAATGTAAGCGTGACATAACTAATTACATGATA

TCGACAAAGGAAAAGGGGCCTGTTTACTCACAGGCTTTTTTCAAGTAGGTAATTAAGTCGTTTC

TGTCTTTTTCCTTCTTCAACCCACCAAAGGCCATCTTGGTACTTTTTTTTTTTTTTTTTT

TTTTTTTTTTTTTTTTTTTTTTTTTTTTTTTTTTTTTTTTTTTTTTTTTTTTTTTTTTTT

TTTTTTTTCATAGAAATAATACAGAAGTAGATGTTGAATTAGATTAAACTGAAGATATATAATT

TATTGGAAAATACATAGAGCTTTTTGTTGATGCGCTTAAGCGATCAATTCAACAACACCACCAG

CAGCTCTGATTTTTTCTTCAGCCAACTTGGAGACGAATCTAGCTTTGACGATAACTGGAACATT

TGGAATTCTACCCTTACCCAAGATCTTACCGTAACCGGCTGCCAAAGTGTCAATAACTGGAGCA

GTTTCCTTAGAAGCAGATTTCAAGTATTGGTCTCTCTTGTCTTCTGGGATCAATGTCCACAATT

TGTCCAAGTTCAAGACTGGCTTCCAGAAATGAGCTTGTTGCTTGTGGAAGTATCTCATACCAAC

CTTACCGAAATAACCTGGATGGTATTTATCCATGTTAATTCTGTGGTGATGTTGACCACCGGCC

ATACCTCTACCACCGGGGTGCTTTCTGTGCTTACCGATACGACCTTTACCGGCTGAGACGTGAC

CTCTGTGCTTTCTAGTCTTAGTGAATCTGGAAGGCATTCTTGATTAGTTGGATGATTGTTCTGG

GATTTAATGCAAAAATCACTTAAGAAGGAAAATCAACGGAGAAAGCAAACGCCATCTTAAATAT

ACGGGATACAGATGAAAGGGTTTGAACCTATCTGGAAAATAGCATTAAACAAGCGAAAAACTGC

GAGGAAAATTGTTTGCGTCTCTGCGGGCTATTCACGCGCCAGAGGAAAATAGGAAAAATAACAG

GGCATTAGAAAAATAATTTTGATTTTGGTAATGTGTGGGTCCTGGTGTACAGATGTTACATTGG

TTACAGTACTCTTGTTTTTGCTGTGTTTTTCGATGAATCTCCAAAATGGTTGTTAGCACATGGA

AGAGTCACCGATGCTAAGTTATCTCTATGTAAGCTACGTGGCGTGACTTTTGATGAAGCCGCAC

-continued

AAGAGATACAGGATTGGCAACTGCAAATAGAATCTGGGGATCCCCCCTCGACGGATGCAAGGGT

TCGAATCCCTTAGCTCTCATTATTTTTTGCTTTTTCTCTTGAG.GTSGTCACATGATCGCAAAA

TGGCAAATGGCACGTGAAGCTGTCGATATTGGGGAACTGTGGTGGTTGGCAAATGACTAATTAA

GTTAGTCAAGGCGCCATCCTCATGAAAACTGTGTAACATAATAACCGAAGTGTCGAAAAGGTGG

CACCTTGTCCAATTGAACACGCTCGATGAAAAAAATAAGATATATATAAGGTTAAGTAAAGCGT

CTGTTAGAAAGGAAGTTTTTCCTTTTTCTTGCTCTCTTGTCTTTTCATCTACTATTTCCTTCGT

GTAATACAGGGTCGTCAGATACATAGATACAATTCTATTACCCCCATCCATACATCTAGAACTA

GTGGATCCCCCGGGCTGCAGGAATTCGATATCAAGCTTCACAGCTAGCGCACTCGGTGCCCCGC

GCAGGGTCGCGATGCTGCCCGGTTTGGCACTGTTCCTGCTGGCCGCCTGGACGGCTCGGGCGCT

GGATGCAGAATTCCGACATGACTCAGGATATGAAGTTCATCATCAAAAATTGGTGTTCTTTGCA

GAAGATGTGGGTTCAAACAAAGGTGCAATCATTGGACTCATGGTGGGCGGTGTTGTCATAGCGA

CAGTGATCGTCATCACCTTGGTGATGCTGAAGAAGAAACAGTACACATCCATTCATCATGGTGT

GGTGGAGGTTGACGCCGCTGTCACCCCAGAGGAGCGCCACCTGTCCAAGATGCAGCAGAACGGC

TACGAAAATCCAACCTACAAGTTCTTTGAGCAGATGCAGAACGCGCGGGGTACCCCGGCGATGA

AGCTACTGTCTTCTATCGAACAAGCATGCGATATTTGCCGACTTAAAAAGCTCAAGTGCTCCAA

AGAAAAACCGAAGTGCGCCAAGTGTCTGAAGAACAACTGGGAGTGTCGCTACTCTCCCAAAACC

AAAAGGTCTCCGCTGACTAGGGCACATCTGACAGAAGTGGAATCAAGGCTAGAAAGACTGGAAC

AGCTATTTCTACTGATTTTTCCTCGAGAAGACCTTGACATGATTTTGAAAATGGATTCTTTACA

GGATATAAAAGCATTGTTAACAGGATTATTTGTACAAGATAATGTGAATAAAGATGCCGTCACA

GATAGATTGGCTTCAGTGGAGACTGATATGCCTCTAACATTGAGACAGCATAGAATAAGTGCGA

CATCATCATCGGAAGAGAGTAGTAACAAAGGTCAAAGACAGTTGACTGTATCGCCGGAATTCCC

GGGGATCTGGGCCCCCCCGACCGATGTCAGCCTGGGGGACGAGCTCCACTTAGACGGCGAGGAC

GTGGCGATGGCGCATGCCGACGCGCTAGACGATTTCGATCTGGACATGTTGGGGGACGGGGATT

CCCCGGGGCCGGGATTTACCCCCCACGACTCCGCCCCCTACGGCGCTCTGGATATGGCCGACTT

CGAGTTTGAGCAGATGTTTACCGATGCCCTTGGAATTGACGAGTACGGTGGGTAGGGATCCACT

AGTCCAGTGTGGTGGAATTCTGCAGATATCCAGCACAGTGGCGGCCGCTCGACCCCGGGTGCTA

GCAAGGCCTTGTGGCCAGCCATGGCAACTAGTGCGGCCGCTAAGTAAGTAAGACGTCGAGCTCT

AAGTAAGTAACGGCCGCCACCGCGGTGGAGCTTTGGACTTCTTCGCCAGAGGTTTGGTCAAGTC

TCCAATCAAGGTTGTCGGCTTGTCTACCTTGCCAGAAATTTACGAAAAGATGGAAAAGGGTCAA

ATCGTTGGTAGATACGTTGTTGACACTTCTAAATAAGCGAATTTCTTATGATTTATGATTTTTA

TTATTAAATAAGTTATAAAAAAAATAAGTGTATACAAATTTTAAAGTGACTCTTAGGTTTTAAA

ACGAAAATTCTTGTTCTTGAGTAACTCTTTCCTGTAGGTCAGGTTGCTTTCTCAGGTATAGCAT

GAGGTCGCTCTTATTGACCACACCTCTACCGGCATGCCGAGCAAATGCCTGCAAATCGCTCCCC

ATTTCACCCAATTGTAGATATGCTAACTCCAGCAATGAGTTGATGAATCTCGGTGTGTATTTTA

TGTCCTCAGAGGACAATACCTGTTGTAATCGTTCTTCCACACGGATCCCAATTCGCCCTATAGT

GAGTCGTATTACAATTCACTGGCCGTCGTTTTACAACGTCGTGACTGGGAAAACCCTGGCGTTA

CCCAACTTAATCGCCTTGCAGCACATCCCCCTTTCGCCAGCTGGCGTAATAGCGAAGAGGCCCG

CACCGATCGCCCTTCCCAACAGTTGCGCAGCCTGAATGGCGAATGGACGCGCCCTGTAGCGGCG

CATTAAGCGCGGCGGGTGTGGTGGTTACGCGCAGCGTGACCGCTACACTTGCCAGCGCCCTAGC

GCCCGCTCCTTTCGCTTTCTTCCCTTCCTTTCTCGCCACGTTCGCCGGCTTTCCCCGTCAAGCT

-continued

CTAAATCGGGGGCTCCCTTTAGGGTTCCGATTTAGTGCTTTACGGCACCTCGACCCCAAAAAAC

TTGATTAGGGTGATGGTTCACGTAGTGGGCCATCGCCCTGATAGACGGTTTTTCGCCCTTTGAC

GTTGGAGTCCACGTTCTTTAATAGTGGACTCTTGTTCCAAACTGGAACAACACTCAACCCTATC

TCGGTCTATTCTTTTGATTTATAAGGGATTTTGCCGATTTCGGCCTATTGGTTAAAAAATGAGC

TGATTTAACAAAAATTTAACGCGAATTTTAACAAAATATTAACGTTTACAATTTCCTGATGCGG

TATTTTCTCCTTACGCATCTGTGCGGTATTTCACACCGCAGGCAAGTGCACAAACAATACTTAA

ATAAATACTACTCAGTAATAACCTATTTCTTAGCATTTTTGACGAAATTTGCTATTTTGTTAGA

GTCTTTTACACCATTTGTCTCCACACCTCCGCTTACATCAACACCAATAACGCCATTTAATCTA

AGCGCATCACCAACATTTTCTGGCGTCAGTCCACCAGCTAACATAAAATGTAAGCTTTCGGGGC

TCTCTTGCCTTCCAACCCAGTCAGAAATCGAGTTCCAATCCAAAAGTTCACCTGTCCCACCTGC

TTCTGAATCAAACAAGGGAATAAACGAATGAGGTTTCTGTGAAGCTGCACTGAGTAGTATGTTG

CAGTCTTTTGGAAATACGAGTCTTTTAATAACTGGCAAACCGAGGAACTCTTGGTATTCTTGCC

ACGACTCATCTCCATGCAGTTGGACGATATCAATGCCGTAATCATTGACCAGAGCCAAAACATC

CTCCTTAGGTTGATTACGAAACACGCCAACCAAGTATTTCGGAGTGCCTGAACTATTTTTATAT

GCTTTTACAAGACTTGAAATTTTCCTTGCAATAACCGGGTCAATTGTTCTCTTTCTATTGGGCA

CACATATAATACCCAGCAAGTCAGCATCGGAATCTAGAGCACATTCTGCGGCCTCTGTGCTCTG

CAAGCCGCAAACTTTCACCAATGGACCAGAACTACCTGTGAAATTAATAACAGACATACTCCAA

GCTGCCTTTGTGTGCTTAATCACGTATACTCACGTGCTCAATAGTCACCAATGCCCTCCCTCTT

GGCCCTCTCCTTTTCTTTTTTCGACCGAATTAATTCTTAATCGGCAAAAAAAGAAAAGCTCCGG

ATCAAGATTGTACGTAAGGTGACAAGCTATTTTTCAATAAAGAATATCTTCCACTACTGCCATC

TGGCGTCATAACTGCAAAGTACACATATATTACGATGCTGTCTATTAAATGCTTCCTATATTAT

ATATATAGTAATGTCGTTTATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGCATCC

GCTTACAGACAAGCTGTGACCGTCTCCGGGAGCTGCATGTGTCAGAGGTTTTCACCGTCATCAC

CGAAACGCGCGA

SEQ ID No. 11 (SP-C100-GAL4-VP16 fusion protein)
MLPGLALFLL AAWTARALDA EFRHDSGYEV HHQKLVFFAE DVGSNKGAII

GLMVGGVVIA TVIVITLVML KKKQYTSIHH GVVEVDAAVT PEERHLSKMQ

QNGYENPTYK FFEQMQNARG TPANKLLSSI EQACDICRLK KLKCSKEKPK

CAKCLKNNWE CRYSPKTKRS PLTRAHLTEV ESRLERLEQL FLLIFPREDL

DMILKMDSLQ DIKALLTGLF VQDNVNKDAV TDRLASVETD MPLTLRQHRI

SATSSSEESS NKGQRQLTVS PEFPGIWAPP TDVSLGDELH LDGEDVAMAH

ADALDDFDLD MLGDGDSPGP GFTPHDSAPY GALDMADFEF EQMFTDALGT

DEY GG

SEQ ID No. 12 (Signal peptide of yeast SUC2 gene (SP2))
MLLRAFLFLLAGFAAKISAALA

SEQ ID No. 13
(Signal peptide of mammalian basal membrane protein BM40 (SP3))
MRAWIFFLLCLAGRALA SEQ ID No. 14 (SP-C55-GAL4-VP16)
MLPGLALFLL AAWTARALDA EFRHDSGYEV HHQKLVFFAE DVGSNKGAII

GLMVGGVVIA TVIVITLVML KKKGRSGKLL SSIEQACDIC RLKKLKCSKE

KPKCAKCLKN NWECRYSPKT KRSPLTRAHL TEVESRLERL EQLFLLIFPR

-continued

EDLDMILKMD SLQDIKALLT GLFVQDNVNK DAVTDRLASV ETDMPLTLRQ

HRISATSSSE ESSNKGQRQL TVSPEFPGIW APPTDVSLGD ELHLDGEDVA

MAHADALDDF DLDMLGDGDS PGPGFTPHDS APYGALEMAD FEFEQMFTDA

LGIDEYGG

SEQ ID No. 15 (SP-C55-GAL4/VP16-TAG)

```
   1 gacggatcgg gagatctccc gatcccctat ggtcgactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggac tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc ctacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aaatgtcgta acaactccgc cccattgacg caaatgggcg
 781 gtaggcgtgt acggtgggag gtctatataa gcagagctct ctggctaact agagaaccca
 841 ctgcttaact ggcttatcga aattaatacg actcactata gggagaccca agcttctgcc
 901 tgccgcctgc ctgcctgcca ctgagggttc ccagcaccat gagggcctgg atcttctttc
 961 tcctttgcct ggccgggagg gctctggcag ccccgctagc tgatgcagaa ttccgacatg
1021 actcaggata tgaagttcat catcaaaaat tggtgttctt tgcagaagat gtgggttcaa
1081 acaaaggtgc aatcattgga ctcatggtgg gcggtgttgt catagcgaca gtgatcgtca
1141 tcaccttggt gatgctgaag aagaaaggta gatctggcaa gctactgtct tctatcgaac
1201 aagcatgcga tatttgccga cttaaaaagc tcaagtgctc caaagaaaaa ccgaagtgcg
1261 ccaagtgtct gaagaacaac tgggagtgtc gctactctcc caaaaccaaa aggtctccgc
1321 tgactagggc acatctgaca gaagtggaat caaggctaga aagactggaa cagctatttc
1381 tactgatttt tcctcgagaa gaccttgaca tgattttgaa aatggattct ttacaggata
1441 taaaagcatt gttaacagga ttatttgtac aagataatgt gaataaagat gccgtcacag
1501 atagattggc ttcagtggag actgatatgc ctctaacatt gagacagcat agaataagtg
1561 cgacatcatc atcggaagag agtagtaaca aaggtcaaag acagttgact gtatcgccgg
1621 aattcccggg gatctgggcc cccccgaccg atgtcagcct gggggacgag ctccacttag
1681 acggcgagga cgtggcgatg gcgcatgccg acgcgctaga cgatttcgat ctggacatgt
1741 tgggggacgg ggattccccg ggtccgggat ttacccccca cgactccgcc ccctacggcg
1801 ctctggatat ggccgacttc gagtttgagc agatgtttac cgatgccctt ggaattgacg
1861 agtacggtgg gggttagaaa atcgataccg tcgaggccgc tcgagcatgc atctagaggg
1921 ccctattcta tagtgtcacc taaatgctag agctcgctga tcagcctcga ctgtgccttc
1981 tagttgccag ccatctgttg tttgcccctc ccccgtgcct tccttgaccc tggaaggtgc
2041 cactcccact gtcctttcct aataaaatga ggaaattgca tcgcattgtc tgagtaggtg
```

-continued 2101 tcattctatt ctggggggtg gggtggggca ggacagcaag ggggaggatt gggaagacaa 2161 tagcaggcat gctggggatg cggtgggctc tatggaacca gctggggctc gagggggat 2221 ccccacgcgc cctgtagcgg cgcattaagc gcggcgggtg tggtggttac gcgcagcgtg 2281 accgctacac ttgccagcgc cctagcgccc gctcctttcg ctttcttccc ttcctttctc 2341 gccacgttcg ccggctttcc ccgtcaagct ctaaatcggg gcatcccttt agggttccga 2401 tttagtgctt tacggcacct cgaccccaaa aaacttgatt agggtgatgg ttcacgtagt 2461 gggccatcgc cctgatagac ggtttttcgc cctttgacgt tggagtccac gttctttaat 2521 agtggactct tgttccaaac tggaacaaca ctcaacccta tctcggtcta ttcttttgat 2581 ttataaggga ttttggggat ttcggcctat tggttaaaaa atgagctgat ttaacaaaaa 2641 tttaacgcga attttaacaa aatattaacg tttacaattt aaatatttgc ttatacaatc 2701 ttcctgtttt tggggctttt ctgattatca accggggtgg gtaccgagct cgaattctgt 2761 ggaatgtgtg tcagttaggg tgtggaaagt ccccaggctc cccaggcagg cagaagtatg 2821 caaagcatgc atctcaatta gtcagcaacc aggtgtggaa agtccccagg ctccccagca 2881 ggcagaagta tgcaaagcat gcatctcaat tagtcagcaa ccatagtccc gcccctaact 2941 ccgcccatcc cgcccctaac tccgcccagt tccgcccatt ctccgcccca tggctgacta 3001 atttttttta tttatgcaga ggccgaggcc gcctcggcct ctgagctatt ccagaagtag 3061 tgaggaggct tttttggagg cctaggcttt tgcaaaaagc tcccgggagc ttggatatcc 3121 attttcggat ctgatcaaga gacaggatga ggatcgtttc gcatgattga acaagatgga 3181 ttgcacgcag gttctccggc cgcttgggtg gagaggctat tcggctatga ctgggcacaa 3241 cagacaatcg gctgctctga tgccgccgtg ttccggctgt cagcgcaggg gcgcccggtt 3301 ctttttgtca agaccgacct gtccggtgcc ctgaatgaac tgcaggacga ggcagcgcgg 3361 ctatcgtggc tggccacgac gggcgttcct tgcgcagctg tgctcgacgt tgtcactgaa 3421 gcgggaaggg actggctgct attgggcgaa gtgccggggc aggatctcct gtcatctcac 3481 cttgctcctg ccgagaaagt atccatcatg gctgatgcaa tgcggcggct gcatacgctt 3541 gatccggcta cctgcccatt cgaccaccaa gcgaaacatc gcatcgagcg agcacgtact 3601 cggatggaag ccggtcttgt cgatcaggat gatctggacg aagagcatca ggggctcgcg 3661 ccagccgaac tgttcgccag gctcaaggcg cgcatgcccg acggcgagga tctcgtcgtg 3721 acccatggcg atgcctgctt gccgaatatc atggtggaaa atggccgctt ttctggattc 3781 atcgactgtg gccggctggg tgtggcggac cgctatcagg acatagcgtt ggctacccgt 3841 gatattgctg aagagcttgg cggcgaatgg gctgaccgct tcctcgtgct ttacggtatc 3901 gccgctcccg attcgcagcg catcgccttc tatcgccttc ttgacgagtt cttctgagcg 3961 ggactctggg gttcgaaatg accgaccaag cgacgcccaa cctgccatca cgagatttcg 4021 attccaccgc cgccttctat gaaaggttgg gcttcggaat cgttttccgg gacgccggct 4081 ggatgatcct ccagcgcggg gatctcatgc tggagttctt cgcccacccc aacttgttta 4141 ttgcagctta taatggttac aaataaagca atagcatcac aaatttcaca aataaagcat 4201 ttttttcact gcattctagt tgtggtttgt ccaaactcat caatgtatct tatcatgtct 4261 ggatcccgtc gacctcgaga gcttggcgta atcatggtca tagctgtttc ctgtgtgaaa 4321 ttgttatccg ctcacaattc cacacaacat acgagccgga agcataaagt gtaaagcctg 4381 gggtgcctaa tgagtgagct aactcacatt aattgcgttg cgctcactgc ccgctttcca 4441 gtcgggaaac ctgtcgtgcc agctgcatta atgaatcggc caacgcgcgg ggagaggcgg -continued 4501 tttgcgtatt gggcgctctt ccgcttcctc gctcactgac tcgctgcgct cggtcgttcg 4561 gctgcggcga gcggtatcag ctcactcaaa ggcggtaata cggttatcca cagaatcagg 4621 ggataacgca ggaaagaaca tgtgagcaaa aggccagcaa aaggccagga accgtaaaaa 4681 ggccgcgttg ctggcgtttt tccataggct ccgcccccct gacgagcatc acaaaaatcg 4741 acgctcaagt cagaggtggc gaaacccgac aggactataa agataccagg cgtttccccc 4801 tggaagctcc ctcgtgcgct ctcotgttcc gaccctgccg cttaccggat acctgtccgc 4861 ctttctccct tcgggaagcg tggcgctttc tcaatgctca cgctgtaggt atctcagttc 4921 ggtgtaggtc gttcgctcca agctgggctg tgtgcacgaa ccccccgttc agcccgaccg 4981 ctgcgcctta tccggtaact atcgtcttga gtccaacccg gtaagacacg acttatcgcc 5041 actggcagca gccactggta acaggattag cagagcgagg tatgtaggcg gtgctacaga 5101 gttcttgaag tggtggccta actacggcta cactagaagg acagtatttg gtatctgcgc 5161 tctgctgaag ccagttacct tcggaaaaag agttggtagc tcttgatccg gcaaacaaac 5221 caccgctggt agcggtggtt tttttgtttg caagcagcag attacgcgca gaaaaaaagg 5281 atctcaagaa gatcctttga tcttttctac ggggtctgac gctcagtgga acgaaaactc 5341 acgttaaggg attttggtca tgagattatc aaaaaggatc ttcacctaga tccttttaaa 5401 ttaaaaatga agttttaaat caatctaaag tatatatgag taaacttggt ctgacagtta 5461 ccaatgctta atcagtgagg cacctatctc agcgatctgt ctatttcgtt catccatagt 5521 tgcctgactc cccgtcgtgt agataactac gatacgggag ggcttaccat ctggccccag 5581 tgctgcaatg ataccgcgag acccacgctc accggctcca gatttatcag caataaacca 5641 gccagccgga agggccgagc gcagaagtgg tcctgcaact ttatccgcct ccatccagtc 5701 tattaattgt tgccgggaag ctagagtaag tagttcgcca gttaatagtt tgcgcaacgt 5761 tgttgccatt gctacaggca tcgtggtgtc acgctcgtcg tttggtatgg cttcattcag 5821 ctccggttcc caacgatcaa ggcgagttac atgatccccc atgttgtgca aaaaagcggt 5881 tagctccttc ggtcctccga tcgttgtcag aagtaagttg gccgcagtgt tatcactcat 5941 ggttatggca gcactgcata attctcttac tgtcatgcca tccgtaagat gcttttctgt 6001 gactggtgag tactcaacca agtcattctg agaatagtgt atgcggcgac cgagttgctc 6061 ttgcccggcg tcaatacggg ataataccgc gccacatagc agaactttaa aagtgctcat 6121 cattggaaaa cgttcttcgg ggcgaaaact ctcaaggatc ttaccgctgt tgagatccag 6181 ttcgatgtaa cccactcgtg cacccaactg atcttcagca tcttttactt tcaccagcgt 6241 ttctgggtga gcaaaaacag gaaggcaaaa tgccgcaaaa aagggaataa gggcgacacg 6301 gaaatgttga atactcatac tcttcctttt tcaatattat tgaagcattt atcagggtta 6361 ttgtctcatg agcggataca tatttgaatg tatttagaaa aataaacaaa taggggttcc 6421 gcgcacattt ccccgaaaag tgccacctga cgtc SEQ ID No. 16 (Recombinant Plasmid pDBTrp-MET25-SP-C-Gal4/VP16-100)

1 gacgaaaggg cctcgtgata cgcctatttt tataggttaa tgtcatgata ataatggttt 61 cttaggacgg atcgcttgcc tgtaacttac acgcgcctcg tatcttttaa tgatggaata 121 atttgggaat ttactctgtg tttatttatt tttatgtttt gtatttggat tttagaaagt 181 aaataaagaa ggtagaagag ttacggaatg aagaaaaaaa aataaacaaa ggtttaaaaa 241 atttcaacaa aaagcgtact ttacatatat atttattaga caagaaaagc agattaaata 301 gatatacatt cgattaacga taagtaaaat gtaaaatcac aggattttcg tgtgtggtct 361 tctacacaga caagatgaaa caattcggca ttaatacctg agagcaggaa gagcaagata -continued 421 aaaggtagta tttgttggcg atccccctag agtcttttac atcttcggaa aacaaaaact
481 attttttctt taatttcttt ttttactttc tatttttaat ttatatattt atattaaaaa
541 atttaaatta taattatttt tatagcacgt gatgaaaagg acccaggtgg cacttttcgg
601 ggaaatgtgc gcggaacccc tatttgttta tttttctaaa tacattcaaa tatgtatccg
661 ctcatgagac aataaccctg ataaatgctt caataatctg cagctctggc ccgtgtctca
721 aaatctctga tgttacattg cacaagataa aaatatatca tcatgaacaa taaaactgtc
781 tgcttacata aacagtaata caaggggtgt tatgagccat attcaacggg aaacgtcttg
841 ctggaggccg cgattaaatt ccaacatgga tgctgattta tatgggtata aatgggctcg
901 cgataatgtc gggcaatcag gtgcgacaat ctttcgattg tatgggaagc ccgatgcgcc
961 agagttgttt ctgaaacatg gcaaaggtag cgttgccaat gatgttacag atgagatggt
1021 cagactaaac tggctgacgg aatttatgcc tcttccgacc atcaagcatt ttatccgtac
1081 tcctgatgat gcatggttac tcaccactgc gatccgcggg aaaacagcat tccaggtatt
1141 agaagaatat cctgattcag gtgaaaatat tgttgatgcg ctggcagtgt tcctgcgccg
1201 gttgcattcg attcctgttt gtaattgtcc ttttaacagc gatcgcgtat ttcgtctcgc
1261 tcaggcgcaa tcacgaatga ataacggttt ggttgatgcg agtgattttg atgacgagcg
1321 taatggctgg cctgttgaac aagtctggaa agaaatgcat acgcttttgc cattctcacc
1381 ggattcagtc gtcactcatg gtgatttctc acttgataac cttatttttg acgaggggaa
1441 attaataggt tgtattgatg ttggacgagt cggaatcgca gaccgatacc aggatcttgc
1501 catcctatgg aactgcctcg gtgagttttc tccttcatta cagaaacggc tttttcaaaa
1561 atatggtatt gataatcctg atatgaataa attgcagttt catttgatgc tcgatgagtt
1621 tttctaatca gaattggtta attggttgta acactggcag agcattacgc tgacttgacg
1681 ggacggcgca tgaccaaaat cccttaacgt gagttttcgt tccactgagc gtcagacccc
1741 gtagaaaaga tcaaaggatc ttcttgagat cctttttttc tgcgcgtaat ctgctgcttg
1801 caaacaaaaa aaccaccgct accagcggtg gtttgtttgc cggatcaaga gctaccaact
1861 ctttttccga aggtaactgg cttcagcaga gcgcagatac caaatactgt ccttctagtg
1921 tagccgtagt taggccacca cttcaagaac tctgtagcac cgcctacata cctcgctctg
1981 ctaatcctgt taccagtggc tgctgccagt ggcgataagt cgtgtcttac cgggttggac
2041 tcaagacgat agttaccgga taaggcgcag cggtcgggct gaacgggggg ttcgtgcaca
2101 cagcccagct tggagcgaac gacctacacc gaactgagat acctacagcg tgagcattga
2161 gaaagcgcca cgcttcccga agggagaaag gcggacaggt atccggtaag cggcagggtc
2221 ggaacaggag agcgcacgag ggagcttcca gggggaaacg cctggtatct ttatagtcct
2281 gtcgggtttc gccacctctg acttgagcgt cgatttttgt gatgctcgtc aggggggccg
2341 agcctatgga aaaacgccag caacgcggcc tttttacggt tcctggcctt ttgctggcct
2401 tttgctcaca tgttctttcc tgcgttatcc cctgattctg tggataaccg tattaccgcc
2461 tttgagtgag ctgataccgc tcgccgcagc cgaacgaccg agcgcagcga gtcagtgagc
2521 gaggaagcgg aagagcgccc aatacgcaaa ccgcctctcc ccgcgcgttg gccgattcat
2581 taatgcagct ggcacgacag gtttcccgac tggaaagcgg gcagtgagcg caacgcaatt
2641 aatgtgagtt acctcactca ttaggcaccc caggctttac actttatgct tccggctcct
2701 atgttgtgtg gaattgtgag cggataacaa tttcacacag gaaacagcta tgaccatgat
2761 tacgccaagc tcggaattaa ccctcactaa agggaacaaa agctggtacc gatcccgagc -continued 2821 tttgcaaatt aaagccttcg agcgtcccaa aaccttctca agcaaggttt tcagtataat
2881 gttacatgcg tacacgcgtc tgtacagaaa aaaaagaaaa atttgaaata taaataacgt
2941 tcttaatact aacataacta taaaaaaata aatagggacc tagacttcag gttgtctaac
3001 tccttccttt tcggttagag cggatgtggg gggagggcgt gaatgtaagc gtgacataac
3061 taattacatg atatcgacaa aggaaaaggg gcctgtttac tcacaggctt ttttcaagta
3121 ggtaattaag tcgtttctgt ctttttcctt cttcaaccca ccaaaggcca tcttggtact
3181 tttttttttt tttttttttt tttttttttt tttttttttt tttttttttt tttttttttt
3241 tttttttttt tttttttttt tttttttttt tttcatagaa ataatacaga agtagatgtt
3301 gaattagatt aaactgaaga tatataattt attggaaaat acatagagct ttttgttgat
3361 gcgcttaagc gatcaattca acaacaccac cagcagctct gatttttttct tcagccaact
3421 tggagacgaa tctagctttg acgataactg gaacatttgg aattctaccc ttacccaaga
3481 tcttaccgta accggctgcc aaagtgtcaa taactggagc agtttcctta gaagcagatt
3541 tcaagtattg gtctctcttg tcttctggga tcaatgtcca caatttgtcc aagttcaaga
3601 ctggcttcca gaaatgagct tgttgcttgt ggaagtatct cataccaacc ttaccgaaat
3661 aacctggatg gtatttatcc atgttaattc tgtggtgatg ttgaccaccg gccatacctc
3721 taccaccggg gtgctttctg tgcttaccga tacgaccttt accggctgag acgtgacctc
3781 tgtgctttct agtcttagtg aatctggaag gcattcttga ttagttggat gattgttctg
3841 ggatttaatg caaaaatcac ttaagaagga aaatcaacgg agaaagcaaa cgccatctta
3901 aatatacggg atacagatga aagggtttga acctatctgg aaaatagcat taaacaagcg
3961 aaaaactgcg aggaaaattg tttgcgtctc tgcgggctat tcacgcgcca gaggaaaata
4021 ggaaaaataa cagggcatta gaaaaataat tttgattttg gtaatgtgtg ggtcctggtg
4081 tacagatgtt acattggtta cagtactctt gtttttgctg tgtttttcga tgaatctcca
4141 aaatggttgt tagcacatgg aagagtcacc gatgctaagt tatctctatg taagctacgt
4201 ggcgtgactt ttgatgaagc cgcacaagag atacaggatt ggcaactgca aatagaatct
4261 ggggatcccc cctcgacgga tgcaagggtt cgaatccctt agctctcatt atttttttgct
4321 ttttctcttg aggtcacatg atcgcaaaat ggcaaatggc acgtgaagct gtcgatattg
4381 gggaactgtg gtggttggca aatgactaat taagttagtc aaggcgccat cctcatgaaa
4441 actgtgtaac ataataaccg aagtgtcgaa aaggtggcac cttgtccaat tgaacacgct
4501 cgatgaaaaa aataagatat atataaggtt aagtaaagcg tctgttagaa aggaagtttt
4561 tcctttttct tgctctcttg tcttttcatc tactatttcc ttcgtgtaat acagggtcgt
4621 cagatacata gatacaattc tattaccccc atccatactc tagaatgctt ttgcgagctt
4681 tccttttcct cttggctggt tttgcagcca aaatatctgc agcgctagct gatgcagaat
4741 tccgacatga ctcaggatat gaagttcatc atcaaaaatt ggtgttcttt gcagaagatg
4801 tgggttcaaa caaaggtgca atcattggac tcatggtggg cggtgttgtc atagcgacag
4861 tgatcgtcat caccttggtg atgctgaaga agaaaggtag atctggcaag ctactgtctt
4921 ctatcgaaca agcatgcgat atttgccgac ttaaaaagct caagtgctcc aaagaaaaac
4981 cgaagtgcgc caagtgtctg aagaacaact gggagtgtcg ctactctccc aaaaccaaaa
5041 ggtctccgct gactagggca catctgacag aagtggaatc aaggctagaa agactggaac
5101 agctatttct actgattttt cctcgagaag accttgacat gattttgaaa atggattctt
5161 tacaggatat aaaagcattg ttaacaggat tatttgtaca agataatgtg aataaagatg -continued 5221 ccgtcacaga tagattggct tcagtggaga ctgatatgcc tctaacattg agacagcata 5281 gaataagtgc gacatcatca tcggaagaga gtagtaacaa aggtcaaaga cagttgactg 5341 tatcgccgga attcccgggg atctgggccc ccccgaccga tgtcagcctg ggggacgagc 5401 tccacttaga cggcgaggac gtggcgatgg cgcatgccga cgcgctagac gatttcgatc 5461 tggacatgtt gggggacggg gattccccgg gtccgggatt tacccccac gactccgccc 5521 cctacggcgc tctggatatg gccgacttcg agtttgagca gatgtttacc gatgcccttg 5581 gaattgacga gtacggtggg ggtactagtg gccagtacac atccattcat catggtgtgg 5641 tggaggttga cgccgctgtc accccagagg agcgccacct gtccaagatg cagcagaacg 5701 gctacgaaaa tccaacctac aagttctttg agcagatgca gaacggcgcc tagggatccc 5761 ccgggctgca ggaattcgat atcaagctta tcgataccgt cgaccccggg tgctagcaag 5821 gccttgtggc cagccatggc aactagtgcg gccgctaagt aagtaagacg tcgagctcta 5881 agtaagtaac ggccgccacc gcggtggagc tttggacttc ttcgccagag gtttggtcaa 5941 gtctccaatc aaggttgtcg gcttgtctac cttgccagaa atttacgaaa agatggaaaa 6001 gggtcaaatc gttggtagat acgttgttga cacttctaaa taagcgaatt tcttatgatt 6061 tatgattttt attattaaat aagttataaa aaaaataagt gtatacaaat tttaaagtga 6121 ctcttaggtt ttaaaacgaa aattcttgtt cttgagtaac tctttcctgt aggtcaggtt 6181 gctttctcag gtatagcatg aggtcgctct tattgaccac acctctaccg gcatgccgag 6241 caaatgcctg caaatcgctc cccatttcac ccaattgtag atatgctaac tccagcaatg 6301 agttgatgaa tctcggtgtg tattttatgt cctcagagga caatacctgt tgtaatcgtt 6361 cttccacacg gatcccaatt cgccctatag tgagtcgtat tacaattcac tggccgtcgt 6421 tttacaacgt cgtgactggg aaaaccctgg cgttacccaa cttaatcgcc ttgcagcaca 6481 tccccctttc gccagctggc gtaatagcga agaggcccgc accgatcgcc cttcccaaca 6541 gttgcgcagc ctgaatggcg aatggacgcg ccctgtagcg gcgcattaag cgcggcgggt 6601 gtggtggtta cgcgcagcgt gaccgctaca cttgccagcg ccctagcgcc cgctcctttc 6661 gctttcttcc cttcctttct cgccacgttc gccggctttc cccgtcaagc tctaaatcgg 6721 gggctccctt tagggttccg atttagtgct ttacggcacc tcgaccccaa aaaacttgat 6781 tagggtgatg gttcacgtag tgggccatcg ccctgataga cggtttttcg ccctttgacg 6841 ttggagtcca cgttctttaa tagtggactc ttgttccaaa ctggaacaac actcaaccct 6901 atctcggtct attcttttga tttataaggg attttgccga tttcggccta ttggttaaaa 6961 aatgagctga tttaacaaaa atttaacgcg aattttaaca aaatattaac gtttacaatt 7021 tcctgatgcg gtattttctc cttacgcatc tgtgcggtat ttcacaccgc aggcaagtgc 7081 acaaacaata cttaaataaa tactactcag taataaccta tttcttagca tttttgacga 7141 aatttgctat tttgttagag tcttttacac catttgtctc cacacctccg cttacatcaa 7201 caccaataac gccatttaat ctaagcgcat caccaacatt ttctggcgtc agtccaccag 7261 ctaacataaa atgtaagctt tcggggctct cttgccttcc aacccagtca gaaatcgagt 7321 tccaatccaa aagttcacct gtcccacctg cttctgaatc aaacaaggga ataaacgaat 7381 gaggtttctg tgaagctgca ctgagtagta tgttgcagtc ttttggaaat acgagtcttt 7441 taataactgg caaaccgagg aactcttggt attcttgcca cgactcatct ccatgcagtt 7501 ggacgatatc aatgccgtaa tcattgacca gagccaaaac atcctcctta ggttgattac 7561 gaaacacgcc aaccaagtat ttcggagtgc ctgaactatt tttatatgct tttacaagac -continued 7621 ttgaaatttt ccttgcaata accgggtcaa ttgttctctt tctattgggc acacatataa 7681 tacccagcaa gtcagcatcg gaatctagag cacattctgc ggcctctgtg ctctgcaagc 7741 cgcaaacttt caccaatgga ccagaactac ctgtgaaatt aataacagac atactccaag 7801 ctgcctttgt gtgcttaatc acgtatactc acgtgctcaa tagtcaccaa tgccctccct 7861 cttggccctc tccttttctt ttttcgaccg aattaattct taatcggcaa aaaaagaaaa 7921 gctccggatc aagattgtac gtaaggtgac aagctatttt tcaataaaga atatcttcca 7981 ctactgccat ctggcgtcat aactgcaaag tacacatata ttacgatgct gtctattaaa 8041 tgcttcctat attatatata tagtaatgtc gtttatggtg cactctcagt acaatctgct 8101 ctgatgccgc atagttaagc cagccccgac acccgccaac acccgctgac gcgccctgac 8161 gggcttgtct gctcccggca tccgcttaca gacaagctgt gaccgtctcc gggagctgca 8221 tgtgtcagag gttttcaccg tcatcaccga aacgcgcga SEQ ID No. 17 (SP2-C-GAL4/VP16-100)
atgcttttgcgagctttccttttcctcttggctggttttgcagccaaaatatctgcagcgctag ctgatgcagaattccgacatgactcaggatatgaagttcatcatcaaaaattggtgttctttgc agaagatgtgggttcaaacaaaggtgcaatcattggactcatggtgggcggtgttgtcatagcg acagtgatcgtcatcaccttggtgatgctgaagaagaaaggtagatctggcaagctactgtctt ctatcgaacaagcatgcgatatttgccgacttaaaaagctcaagtgctccaaagaaaaaccgaa gtgcgccaagtgtctgaagaacaactgggagtgtcgctactctcccaaaaccaaaaggtctccg ctgactagggcacatctgacagaagtggaatcaaggctagaaagactggaacagctatttctac tgatttttcctcgagaagaccttgacatgattttgaaaatggattctttacaggatataaaagc attgttaacaggattatttgtacaagataatgtgaataaagatgccgtcacagatagattggct tcagtggagactgatatgcctctaacattgagacagcatagaataagtgcgacatcatcatcgg aagagagtagtaacaaaggtcaaagacagttgactgtatcgccggaattcccggggatctgggc ccccccgaccgatgtcagcctgggggacgagctccacttagacggcgaggacgtggcgatggcg catgccgacgcgctagacgatttcgatctggacatgttgggggacggggattccccggggccgg gatttacccccccacgactccgccccctacggcgctctggatatggccgacttcgagtttgagca gatgtttaccgatgcccttggaattgacgagtacggtgggggtactagtggccagtacacatcc attcatcatggtgtggtggaggttgacgccgctgtcaccccagaggagcgccacctgtccaaga tgcagcagaacggctacgaaaatccaacctacaagttctttgagcagatgcagaacggcgccta g SEQ ID No. 18 (SP2-C-GAL4/VP16-100)
mllraflfllagfaakisaaladaefrhdsgyevhhqklvffaedvgsnkgaiiglmvggvvia tvivitlvmlkkkgrsgkllssieqacdicrlkklkcskekpkcakclknnwecryspktkrsp ltrahltevesrlerleqlfllifpredldmilkmdslqdikalltglfvqdnvnkdavtdrla svetdmpltlrqhrisatssseessnkgqrqltvspefpgiwapptdvslgdelhldgedvama hadalddfdldmlgdgdspgpgftphdsapygaldmadfefeqmftdalgideygggtsgqyts ihhgvvevdaavtpeerhlskmqqngyenptykffeqmqnga*

SEQ ID No. 19 (SP2-C100-GAL4/VP1E)
atgcttttgcgagctttccttttcctcttggctggttttgcagccaaaatatctgcagcgctag ctgatgcagaattccgacatgactcaggatatgaagttcatcatcaaaaattggtgttctttgc agaagatgtgggttcaaacaaaggtgcaatcattggactcatggtgggcggtgttgtcatagcg -continued acagtgatcgtcatcaccttggtgatgctgaagaagaaacagtacacatccattcatcatggtg tggtggaggttgacgccgctgtcaccccagaggagcgccacctgtccaagatgcagcagaacgg ctacgaaaatccaacctacaagttctttgagcagatgcagaacgcgcggggtaccccggcgatg aagctactgtcttctatcgaacaagcatgcgatatttgccgacttaaaaagctcaagtgctcca aagaaaaaccgaagtgcgccaagtgtctgaagaacaactgggagtgtcgctactctcccaaaac caaaaggtctccgctgactagggcacatctgacagaagtggaatcaaggctagaaagactggaa cagctatttctactgatttttcctcgagaagaccttgacatgattttgaaaatggattctttac aggatataaaagcattgttaacaggattatttgtacaagataatgtgaataaagatgccgtcac agatagattggcttcagtggagactgatatgcctctaacattgagacagcatagaataagtgcg acatcatcatcggaagagagtagtaacaaaggtcaaagacagttgactgtatcgccggaattcc cggggatctgggcccccccgaccgatgtcagcctgggggacgagctccacttagacggcgagga cgtggcgatggcgcatgccgacgcgctagacgatttcgatctggacatgttgggggacggggat tccccgggtccgggatttaccccccacgactccgcccccctacggcgctctggatatggccgact tcgagtttgagcagatgtttaccgatgcccttggaattgacgagtacggtgggtag SEQ ID No. 20 (SP2-C100-GAL4/VP16)
mllraflfllagfaakisaaladaefrhdsgyevhhqklvffaedvgsnkgaiiglmvggvvia tvivitlvmlkkkqytsihhgvvevdaavtpeerhlskmqqngyenptykffeqmgnargtpam kllssieqacdicrlkklkcskekpkcakclknnwecryspktkrspltrahltevesrlerle qlfllifpredldmilkmdslqdikalltglfvqdnvnkdavtdrlasvetdmpltlrqhrisa tssseessnkgqrqltvspefpgiwapptdvslgdelhldgedvamahadalddfdldmlgdgd spgpgftphdsapygaldmadfefeqrnftdalgideygg SEQ ID No. 21 (SP3-C100-GAL4/VP16)
atgagggcctggatcttctttctcctttgcctggccgggagggctctggcagccccgctagctg atgcagaattccgacatgactcaggatatgaagttcatcatcaaaaattggtgttctttgcaga agatgtgggttcaaacaaaggtgcaatcattggactcatggtgggcggtgttgtcatagcgaca gtgatcgtcatcaccttggtgatgctgaagaagaaacagtacacatccattcatcatggtgtgg tggaggttgacgccgctgtcaccccagaggagcgccacctgtccaagatgcagcagaacggcta cgaaaatccaacctacaagttctttgagcagatgcagaacgcgcggggtaccccggcgatgaag ctactgtcttctatcgaacaagcatgcgatatttgccgacttaaaaagctcaagtgctccaaag aaaaaccgaagtgcgccaagtgtctgaagaacaactgggagtgtcgctactctcccaaaaccaa aaggtctccgctgactagggcacatctgacagaagtggaatcaaggctagaaagactggaacag ctatttctactgatttttcctcgagaagaccttgacatgattttgaaaatggattctttacagg atataaaagcattgttaacaggattatttgtacaagataatgtgaataaagatgccgtcacaga tagattggcttcagtggagactgatatgcctctaacattgagacagcatagaataagtgcgaca tcatcatcggaagagagtagtaacaaaggtcaaagacagttgactgtatcgccggaattcccgg ggatctgggcccccccgaccgatgtcagcctgggggacgagctccacttagacggcgaggacgt ggcgatggcgcatgccgacgcgctagacgatttcgatctggacatgttgggggacggggattcc ccgggtccgggatttaccccccacgactccgcccccctacggcgctctggatatggccgacttcg agtttgagcagatgtttaccgatgcccttggaattgacgagtacggtggg SEQ ID No. 22 (SP3-C100-GAL4/VP1G)
mrawiffllclagralaapladaefrhdsgyevhhqklvffaedvgsnkgaiiglmvggvviat vivitlvmlkkkqytsihhgvvevdaavtpeerhlskmqqngyenptykffeqmqnargtpamk -continued llssieqacdicrlkklkcskekpkcakclknnwecryspktkrspltrahltevesrlerleq lfllifpredldmilkmdslqdikalltglfvqdnvnkdavtdrlasvetdmpltlrqhrisat ssseessnkgqrqltvspefpgiwapptdvslgdelhldgedvamahadalddfdldmlgdgds pgpgftphdsapygaldmadfefeqmftdalgideygg SEQ ID No. 23 (Primer EH47)
GCTCTAGAATGCTTTTGCAAGCTTTCCTTTTCCTTTTGGCTGGTTTTGC AGCC

AAAATATCTGCAGCGCTAGCTGATGCAGAATTCCGACATGAC

SEQ ID No. 24 (Primer EH49)
CGGGATCCCTAGGCGCCGTTCTGCATCTGCTCAAAGAAC

SEQ ID No. 25 (Primer EH53)
ACTATATCTAGAATGCTTTTGC

SEQ ID No. 26 (Primer EH54)
TTCGATAGAAGACAGTAGCTTGCCAGATCTACCTTTCTTCTTCAGCATC ACCAA SEQ ID No. 27 Primer EH55)
TTGGTGATGCTGAAGAAGAAAGGTAGATCTGGCAAGCTACTGTCTTCT ATCGAA SEQ ID No. 28 (Primer EH56)
ATGATGAATGGATGTGTACTGGCCACTAGTACCCCCACCGTACTCGTC AATT SEQ ID No. 29 (Primer EH57)
AATTGACGAGTACGGTGGGGGTACTAGTGGCCAGTACACATCCATTC ATCAT SEQ ID No. 30 (Primer EH59)
CGATAAGCTTGATATCGAATTC SEQ ID No. 31 (Primer C55-3')
CCATCGATTTTCTAACCCCCACCGTA SEQ ID No. 32 (Plasmid SP3-C-GAL4/VP16-100)
gacggatcgggagatctcccgatcccctatggtcgactctcagtacaatctgctctgatgccgc atagttaagccagtatctgctccctgcttgtgtgttggaggtcgctgagtagtgcgcgagcaaa atttaagctacaacaaggcaaggcttgaccgacaattgcatgaagaatctgcttagggttaggc gttttgcgctgcttcgcgatgtacgggccagatatacgcgttgacattgattattgactagtta ttaatagtaatcaattacggggtcattagttcatagcccatatatggagttccgcgttacataa cttacggtaaatggcccgcctggctgaccgcccaacgacccccgcccattgacgtcaataatga cgtatgttcccatagtaacgccaatagggactttccattgacgtcaatgggtggactatttacg gtaaactgcccacttggcagtacatcaagtgtatcatatgccaagtacgccccctattgacgtc aatgacggtaaatggcccgcctggcattatgcccagtacatgaccttatgggactttcctactt ggcagtacatctacgtattagtcatcgctattaccatggtgatgcggttttggcagtacatcaa tgggcgtggatagcggtttgactcacggggatttccaagtctccaccccattgacgtcaatggg agtttgttttggcaccaaaatcaacgggactttccaaaatgtcgtaacaactccgccccattga cgcaaatgggcggtaggcgtgtacggtgggaggtctatataagcagagctctctggctaactag agaacccactgcttaactggcttatcgaaattaatacgactcactatagggagacccaagcttc tgcctgccgcctgcctgcctgccactgagggttcccagcaccatgagggcctggatcttctttc tcctttgcctggccgggagggctctggcagccccgctagctgatgcagaattccgacatgactc aggatatgaagttcatcatcaaaaattggtgttctttgcagaagatgtgggttcaaacaaaggt gcaatcattggactcatggtgggcggtgttgtcatagcgacagtgatcgtcatcaccttggtga tgctgaagaagaaaggtagatctggcaagctactgtcttctatcgaacaagcatgcgatatttg ccgacttaaaaagctcaagtgctccaaagaaaaaccgaagtgcgccaagtgtctgaagaacaac tgggagtgtcgctactctcccaaaaccaaaaggtctccgctgactagggcacatctgacagaag -continued tggaatcaaggctagaaagactggaacagctatttctactgatttttcctcgagaagaccttga catgattttgaaaatggattctttacaggatataaaagcattgttaacaggattatttgtacaa gataatgtgaataaagatgccgtcacagatagattggcttcagtggagactgatatgcctctaa cattgagacagcatagaataagtgcgacatcatcatcggaagagagtagtaacaaaggtcaaag acagttgactgtatcgccggaattcccggggatctgggcccccccgaccgatgtcagcctgggg gacgagctccacttagacggcgaggacgtggcgatggcgcatgccgacgcgctagacgatttcg atctggacatgttggggacggggattccccggggccgggatttaccccccacgactccgcccc ctacggcgctctggatatggccgacttcgagtttgagcagatgtttaccgatgcccttggaatt gacgagtacggtgggggtactagtggccagtacacatccattcatcatggtgtggtggaggttg acgccgctgtcaccccagaggagcgccacctgtccaagatgcagcagaacggctacgaaaatcc aacctacaagttctttgagcagatgcagaacggcgcctagggatcccccgggctgcaggaattc gatatcaagcttatcgataccgtcgaggccgctcgagcatgcatctagagggccctattctata gtgtcacctaaatgctagagctcgctgatcagcctcgactgtgccttctagttgccagccatct gttgtttgcccctcccccgtgccttccttgaccctggaaggtgccactcccactgtcctttcct aataaaatgaggaaattgcatcgcattgtctgagtaggtgtcattctattctggggggtggggt ggggcaggacagcaagggggaggattgggaagacaatagcaggcatgctggggatgcggtgggc tctatggaaccagctggggctcgagggggatccccacgcgccctgtagcggcgcattaagcgc ggcgggtgtggtggttacgcgcagcgtgaccgctacacttgccagcgccctagcgcccgctcct ttcgctttcttcccttcctttctcgccacgttcgccggctttccccgtcaagctctaaatcggg gcatccctttagggttccgatttagtgctttacggcacctcgaccccaaaaaacttgattaggg tgatggttcacgtagtgggccatcgccctgatagacggtttttcgccctttgacgttggagtcc acgttctttaatagtggactcttgttccaaactggaacaacactcaaccctatctcggtctatt cttttgatttataagggattttggggatttcggcctattggttaaaaaatgagctgatttaaca aaaatttaacgcgaattttaacaaaatattaacgtttacaatttaaatatttgcttatacaatc ttcctgtttttggggcttttctgattatcaaccggggtgggtaccgagctcgaattctgtggaa tgtgtgtcagttagggtgtggaaagtccccaggctccccaggcaggcagaagtatgcaaagcat gcatctcaattagtcagcaaccaggtgtggaaagtccccaggctccccagcaggcagaagtatg caaagcatgcatctcaattagtcagcaaccatagtcccgcccctaactccgcccatcccgcccc taactccgcccagttccgcccattctccgccccatggctgactaattttttttatttatgcaga ggccgaggccgcctcggcctctgagctattccagaagtagtgaggaggcttttttggaggccta ggcttttgcaaaaagctcccgggagcttggatatccattttcggatctgatcaagagacaggat gaggatcgtttcgcatgattgaacaagatggattgcacgcaggttctccggccgcttgggtgga gaggctattcggctatgactgggcacaacagacaatcggctgctctgatgccgccgtgttccgg ctgtcagcgcaggggcgcccggttctttttgtcaagaccgacctgtccggtgccctgaatgaac tgcaggacgaggcagcgcggctatcgtggctggccacgacgggcgttccttgcgcagctgtgct cgacgttgtcactgaagcgggaagggactggctgctattgggcgaagtgccggggcaggatctc ctgtcatctcaccttgctcctgccgagaaagtatccatcatggctgatgcaatgcggcggctgc atacgcttgatccggctacctgcccattcgaccaccaagcgaaacatcgcatcgagcgagcacg tactcggatggaagccggtcttgtcgatcaggatgatctggacgaagagcatcaggggctcgcg ccagccgaactgttcgccaggctcaaggcgcgcatgcccgacggcgaggatctcgtcgtgaccc -continued atggcgatgcctgcttgccgaatatcatggtggaaaatggccgcttttctggattcatcgactg tggccggctgggtgtggcggaccgctatcaggacatagcgttggctacccgtgatattgctgaa gagcttggcggcgaatgggctgaccgcttcctcgtgctttacggtatcgccgctcccgattcgc agcgcatcgccttctatcgccttcttgacgagttcttctgagcgggactctggggttcgaaatg accgaccaagcgacgcccaacctgccatcacgagatttcgattccaccgccgccttctatgaaa ggttgggcttcggaatcgttttccgggacgccggctggatgatcctccagcgcggggatctcat gctggagttcttcgcccaccccaacttgtttattgcagcttataatggttacaaataaagcaat agcatcacaaatttcacaaataaagcatttttttcactgcattctagttgtggtttgtccaaac tcatcaatgtatcttatcatgtctggatcccgtcgacctcgagagcttggcgtaatcatggtca tagctgtttcctgtgtgaaattgttatccgctcacaattccacacaacatacgagccggaagca taaagtgtaaagcctggggtgcctaatgagtgagctaactcacattaattgcgttgcgctcact gcccgctttccagtcgggaaacctgtcgtgccagctgcattaatgaatcggccaacgcgcgggg agaggcggtttgcgtattgggcgctcttccgcttcctcgctcactgactcgctgcgctcggtcg ttcggctgcggcgagcggtatcagctcactcaaaggcggtaatacggttatccacagaatcagg ggataacgcaggaaagaacatgtgagcaaaaggccagcaaaaggccaggaaccgtaaaaaggcc gcgttgctggcgtttttccataggctccgcccccctgacgagcatcacaaaaatcgacgctcaa gtcagaggtggcgaaacccgacaggactataaagataccaggcgtttccccctggaagctccct cgtgcgctctcctgttccgaccctgccgcttaccggatacctgtccgcctttctcccttcggga agcgtggcgctttctcaatgctcacgctgtaggtatctcagttcggtgtaggtcgttcgctcca agctgggctgtgtgcacgaaccccccgttcagcccgaccgctgcgccttatccggtaactatcg tcttgagtccaacccggtaagacacgacttatcgccactggcagcagccactggtaacaggatt agcagagcgaggtatgtaggcggtgctacagagttcttgaagtggtggcctaactacggctaca ctagaaggacagtatttggtatctgcgctctgctgaagccagttaccttcggaaaaagagttgg tagctcttgatccggcaaacaaaccaccgctggtagcggtggtttttttgtttgcaagcagcag attacgcgcagaaaaaaaggatctcaagaagatcctttgatcttttctacggggtctgacgctc agtggaacgaaaactcacgttaagggattttggtcatgagattatcaaaaaggatcttcaccta gatccttttaaattaaaaatgaagttttaaatcaatctaaagtatatatgagtaaacttggtct gacagttaccaatgcttaatcagtgaggcacctatctcagcgatctgtctatttcgttcatcca tagttgcctgactccccgtcgtgtagataactacgatacgggagggcttaccatctggccccag tgctgcaatgataccgcgagacccacgctcaccggctccagatttatcagcaataaaccagcca gccggaagggccgagcgcagaagtggtcctgcaactttatccgcctccatccagtctattaatt gttgccgggaagctagagtaagtagttcgccagttaatagtttgcgcaacgttgttgccattgc tacaggcatcgtggtgtcacgctcgtcgtttggtatggcttcattcagctccggttcccaacga tcaaggcgagttacatgatcccccatgttgtgcaaaaaagcggttagctccttcggtcctccga tcgttgtcagaagtaagttggccgcagtgttatcactcatggttatggcagcactgcataattc tcttactgtcatgccatccgtaagatgcttttctgtgactggtgagtactcaaccaagtcattc tgagaatagtgtatgcggcgaccgagttgctcttgcccggcgtcaatacgggataataccgcgc cacatagcagaactttaaaagtgctcatcattggaaaacgttcttcggggcgaaaactctcaag gatcttaccgctgttgagatccagttcgatgtaacccactcgtgcacccaactgatcttcagca tcttttactttcaccagcgtttctgggtgagcaaaaacaggaaggcaaaatgccgcaaaaaagg -continued

```
gaataagggcgacacggaaatgttgaatactcatactcttcctttttcaatattattgaagcat

ttatcagggttattgtctcatgagcggatacatatttgaatgtatttagaaaaataaacaaata

ggggttccgcgcacatttccccgaaaagtgccacctgacgtc
```

The invention claimed is:

1. A method for detecting the activity of γ-secretase, the method comprising:

A. providing a transgene encoding a fusion protein, said transgene comprising:
   - a) a first nucleotide sequence encoding the amino acid sequence LDA EFRHDSGYEV HHQKLVFFAE DVGSNKGAII GLMVGGVVIA TVIVITLVML KK (SEQ ID NO. 6);
   - b) a second nucleotide sequence, at the 5' end of the first nucleotide sequence, encoding a signal peptide; and
   - c) a promoter, and a nucleotide sequence at the 3' end of the first nucleotide sequence coding for a protein consisting of a DNA-binding domain and a transcription-activating domain to be expressed as a fusion protein with SEQ ID NO. 6;

B. expressing the fusion protein in an isolated cell or transgenic *C. elegans* that contains γ-secretase said isolated cell or *C. elegans* having a reporter system activatable by release of a polypeptide that comprises VIVITLVML (SEQ ID NO. 3) said released polypeptide that comprises SEQ ID NO. 3 not comprising SEQ ID NO. 6; and C. detecting said polypeptide that comprises VIVITLVML (SEQ ID NO. 3) by observing a report of said reporter system.

2. The method of claim 1, further comprising determining, from the amount of the polypeptide of SEQ ID NO. 3, the amount of γ-secretase activity.

3. The method of claim 1, wherein the fusion protein does not comprise, with the exception of SEQ ID NO. 6, one or more sequences consisting of a caspase cleavage site.

4. The method of claim 1, wherein the cell is a eukaryotic cell.

5. The method of claim 1, wherein the cell is cotransfected with a reporter plasmid comprising a reporter gene under the control of a regulatable promoter.

6. The method of claim 5, wherein the reporter plasmid comprises a reporter gene for EGFP (Enhanced Green Fluorescent Protein), Ura 3, His 3 or Lac Z and the regulatable promoter comprises a GAL4 binding site and a minimal promoter of HIV.

7. The method of claim 1, wherein the transgene is present in a vector.

8. The method of claim 7, wherein the vector is pcDNA 3.1+.

9. An assay for detecting inhibition of γ-secretase, said assay comprising:

a. providing an isolated transgenic cell or a transgenic *C. elegans*, said transgenic cell or a transgenic *C. elegans* comprising:
   - i. a first nucleotide sequence encoding amino acid sequence LDA EFRHDSGYEV HHQKLVFFAE DVGSNKGAII GLMVGGVVIA TVIVITLVML KK (SEQ ID NO. 6)
   - ii. a second nucleotide sequence, at the 5' end of the first nucleotide sequence, encoding a signal peptide; and
   - iii. a promoter, and a nucleotide sequence at the 3' end of the first nucleotide sequence coding for a protein consisting of a DNA-binding domain and a transcription-activating domain to be expressed as a fusion protein with SEQ ID NO. 6, said fusion protein to be used for determining as in c. below b. incubating the transgenic *C. elegans* or isolated transgenic cell with a substance; and c. determining whether a protein comprising the amino acid sequence of SEQ ID NO. 3, but not comprising SEQ ID NO: 6 is formed wherein said isolated transgenic cell or transgenic *C. elegans* is cotransfected with a reporter plasmid comprising a reporter gene under the control of a regulatable promoter comprising a binding site for the DNA-binding domain of said protein consisting of a DNA binding domain and a transcription-activating domain, and wherein c. comprises detecting the polypeptide comprising SEQ ID NO: 3 by observing a report of said reporter under the control of said regulatable promoter.

10. The method of claim 1 wherein the protein having the DNA-binding domain and the transcription-activating domain is the protein of SEQ ID NO: 7 having the GAL4-binding domain and the transcription-activating domain of VP16 or is a protein having a LexA-binding domain and the transcription-activating domain of VP16.

11. The assay of claim 9 wherein the protein having the DNA-binding domain and the transcription-activating domain is the protein of SEQ ID NO: 7 having the GAL4-binding domain and the transcription-activating domain of VP16 or is a protein having a LexA-binding domain and the transcription-activating domain of VP16.

* * * * *

UNITED STATES PATENT AND TRADEMARK OFFICE

CERTIFICATE OF CORRECTION

PATENT NO. : 7,892,778 B2
APPLICATION NO. : 10/849423
DATED : February 22, 2011
INVENTOR(S) : Edmund Hoppe et al.

It is certified that error appears in the above-identified patent and that said Letters Patent is hereby corrected as shown below:

On the title page, item (30), in column 1, under "Foreign Application Priority Data", line 1, delete "03011807" and insert -- 1 481 987 A1 --, therefor.

On page 2, in column 2, under "Other Publications", line 2, delete "(1996)," and insert -- (1986), --, therefor.

In column 2, line 5, after "1446)." delete "great".

In column 5, line 50, delete "VIckova" and insert -- Vlckova --, therefor.

In column 5, line 55-56, delete "metallothionine" and insert -- metallothionein --, therefor.

In column 12, line 41, delete "NheI" and insert -- Nhel --, therefor.

In column 14, line 2, delete "NheI" and insert -- Nhel --, therefor.

In column 16, line 16, delete "HpaI-ClaI" and insert -- Hpal-Clal --, therefor.

In column 16, line 19, delete "HpaI" and insert -- Hpal --, therefor.

In column 16, line 22, delete "ClaI" and insert -- Clal --, therefor.

In column 17, line 2, delete "stably $\gamma$-" and insert -- stably- --, therefor.

Signed and Sealed this
Twenty-sixth Day of July, 2011

David J. Kappos
*Director of the United States Patent and Trademark Office*

SEQUENCE LISTING

```
<160> NUMBER OF SEQ ID NOS: 33

<210> SEQ ID NO 1
<211> LENGTH: 24
<212> TYPE: PRT
<213> ORGANISM: Artificial
<220> FEATURE:
<223> OTHER INFORMATION: APP fragment containing gamma-secretase sites

<400> SEQUENCE: 1

Gly Ala Ile Ile Gly Leu Met Val Gly Gly Val Val Ile Ala Thr Val
1               5                   10                  15

Ile Val Ile Thr Leu Val Met Leu
            20


<210> SEQ ID NO 2
<211> LENGTH: 12
<212> TYPE: PRT
<213> ORGANISM: Artificial
<220> FEATURE:
<223> OTHER INFORMATION: APP fragment generated by gamma-secretase
      cleavage

<400> SEQUENCE: 2

Gly Ala Ile Ile Gly Leu Met Val Gly Gly Val Val
1               5                   10


<210> SEQ ID NO 3
<211> LENGTH: 9
<212> TYPE: PRT
<213> ORGANISM: Artificial
<220> FEATURE:
<223> OTHER INFORMATION: APP fragment generated by gamma-secreatse
      cleavage

<400> SEQUENCE: 3

Val Ile Val Ile Thr Leu Val Met Leu
1               5


<210> SEQ ID NO 4
<211> LENGTH: 100
<212> TYPE: PRT
<213> ORGANISM: Artificial
<220> FEATURE:
<223> OTHER INFORMATION: C100 fragment

<400> SEQUENCE: 4

Leu Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Tyr Thr Ser Ile His His Gly
    50                  55                  60
```

-continued

Val Val Glu Val Asp Ala Ala Val Thr Pro Glu Glu Arg His Leu Ser
65 70 75 80

Lys Met Gln Gln Asn Gly Tyr Glu Asn Pro Thr Tyr Lys Phe Phe Glu
85 90 95

Gln Met Gln Asn
100

<210> SEQ ID NO 5
<211> LENGTH: 17
<212> TYPE: PRT
<213> ORGANISM: Homo sapiens

<400> SEQUENCE: 5

Met Leu Pro Gly Leu Ala Leu Phe Leu Leu Ala Ala Trp Thr Ala Arg
1 5 10 15

Ala

<210> SEQ ID NO 6
<211> LENGTH: 55
<212> TYPE: PRT
<213> ORGANISM: Artificial
<220> FEATURE:
<223> OTHER INFORMATION: C55 fragment

<400> SEQUENCE: 6

Leu Asp Ala Glu Phe Arg His Asp Ser Gly Tyr Glu Val His His Gln
1 5 10 15

Lys Leu Val Phe Phe Ala Glu Asp Val Gly Ser Asn Lys Gly Ala Ile
20 25 30

Ile Gly Leu Met Val Gly Gly Val Val Ile Ala Thr Val Ile Val Ile
35 40 45

Thr Leu Val Met Leu Lys Lys
50 55

<210> SEQ ID NO 7
<211> LENGTH: 232
<212> TYPE: PRT
<213> ORGANISM: Artificial
<220> FEATURE:
<223> OTHER INFORMATION: GAL4-VP16

<400> SEQUENCE: 7

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

-continued

```
Ala Thr Ser Ser Ser Glu Glu Ser Ser Asn Lys Gly Gln Arg Gln Leu
    130                 135                 140

Thr Val Ser Pro Glu Phe Pro Gly Ile Trp Ala Pro Pro Thr Asp Val
145                 150                 155                 160

Ser Leu Gly Asp Glu Leu His Leu Asp Gly Glu Asp Val Ala Met Ala
                165                 170                 175

His Ala Asp Ala Leu Asp Asp Phe Asp Leu Asp Met Leu Gly Asp Gly
            180                 185                 190

Asp Ser Pro Gly Pro Gly Phe Thr Pro His Asp Ser Ala Pro Tyr Gly
        195                 200                 205

Ala Leu Asp Met Ala Asp Phe Glu Phe Glu Gln Met Phe Thr Asp Ala
    210                 215                 220

Leu Gly Ile Asp Glu Tyr Gly Gly
225                 230
```

<210> SEQ ID NO 8
<211> LENGTH: 1813
<212> TYPE: DNA
<213> ORGANISM: Artificial
<220> FEATURE:
<223> OTHER INFORMATION: Mutagen

<400> SEQUENCE: 8

```
ggcaaggctt gaccgacaat tgcatgaaga atctgcttag ggttaggcgt tttgcgctgc     60

ttcgcgatgt acgggccaga tatacgcgtt gacattgatt attgactagt tattaatagt    120

aatcaattac ggggtcatta gttcatagcc catatatgga gttccgcgtt acataactta    180

cggtaaatgg cccgcctggc tgaccgccca acgacccccg cccattgacg tcaataatga    240

cgtatgttcc catagtaacg ccaataggga ctttccattg acgtcaatgg gtggactatt    300

tacggtaaac tgcccacttg gcagtacatc aagtgtatca tatgccaagt acgcccccta    360

ttgacgtcaa tgacggtaaa tggcccgcct ggcattatgc ccagtacatg accttatggg    420

actttcctac ttggcagtac atctacgtat tagtcatcgc tattaccatg gtgatgcggt    480

tttggcagta catcaatggg cgtggatagc ggtttgactc acggggattt ccaagtctcc    540

accccattga cgtcaatggg agtttgtttt ggcaccgcgt gtacggtggg aggtctatat    600

aagcagagct ctctggctaa ctagagaacc cactgcttac tggcttatcg aaattaatac    660

gactcactat agggagaccc aagctggcta gcgtttaaac ttaagcttca cagctagcgc    720

actcggtgcc ccgcgcaggg tcgcgatgct gcccggtttg gcactgttcc tgctggccgc    780

ctggacggct cgggcgctgg atgcagaatt ccgacatgac tcaggatatg aagttcatca    840

tcaaaaattg gtgttctttg cagaagatgt gggttcaaac aaaggtgcaa tcattggact    900

catggtgggc ggtgttgtca tagcgacagt gatcgtcatc accttggtga tgctgaagaa    960

gaaacagtac acatccattc atcatggtgt ggtggaggtt gacgccgctg tcaccccaga   1020

ggagcgccac ctgtccaaga tgcagcagaa cggctacgaa aatccaacct acaagttctt   1080

tgagcagatg cagaacgcgc ggggtacccc ggcgatgaag ctactgtctt ctatcgaaca   1140

agcatgcgat atttgccgac ttaaaaagct caagtgctcc aaagaaaaac cgaagtgcgc   1200

caagtgtctg aagaacaact gggagtgtcg ctactctccc aaaaccaaaa ggtctccgct   1260

gactagggca catctgacag aagtggaatc aaggctagaa agactggaac agctatttct   1320

actgattttt cctcgagaag accttgacat gattttgaaa atggattctt tacaggatat   1380

aaaagcattg ttaacaggat tatttgtaca agataatgtg aataaagatg ccgtcacaga   1440
```

-continued

```
tagattggct tcagtggaga ctgatatgcc tctaacattg agacagcata gaataagtgc   1500

gacatcatca tcggaagaga gtagtaacaa aggtcaaaga cagttgactg tatcgccgga   1560

attcccgggg atctgggccc ccccgaccga tgtcagcctg ggggacgagc tccacttaga   1620

cggcgaggac gtggcgatgg cgcatgccga cgcgctagac gatttcgatc tggacatgtt   1680

gggggacggg gattccccgg ggccgggatt tacccccac gactccgccc cctacggcgc   1740

tctggatatg gccgacttcg agtttgagca gatgtttacc gatgcccttg gaattgacga   1800

gtacggtggg tag                                                       1813
```

<210> SEQ ID NO 9
<211> LENGTH: 3354
<212> TYPE: DNA
<213> ORGANISM: Homo sapiens

<400> SEQUENCE: 9

```
agtttcctcg gcagcggtag gcgagagcac gcggaggagc gtgcgcgggg gccccgggag     60

acggcggcgg tggcggcgcg ggcagagcaa ggacgcggcg gatcccactc gcacagcagc    120

gcactcggtg ccccgcgcag ggtcgcgatg ctgcccggtt tggcactgct cctgctggcc    180

gcctggacgg ctcgggcgct ggaggtaccc actgatggta atgctggcct gctggctgaa    240

ccccagattg ccatgttctg tggcagactg aacatgcaca tgaatgtcca gaatgggaag    300

tgggattcag atccatcagg gaccaaaacc tgcattgata ccaaggaagg catcctgcag    360

tattgccaag aagtctaccc tgaactgcag atcaccaatg tggtagaagc caaccaacca    420

gtgaccatcc agaactggtg caagcggggc cgcaagcagt gcaagaccca tccccacttt    480

gtgattccct accgctgctt agttggtgag tttgtaagtg atgcccttct cgttcctgac    540

aagtgcaaat tcttacacca ggagaggatg gatgtttgcg aaactcatct tcactggcac    600

accgtcgcca aagagacatg cagtgagaag agtaccaact tgcatgacta cggcatgttg    660

ctgccctgcg gaattgacaa gttccgaggg gtagagtttg tgtgttgccc actggctgaa    720

gaaagtgaca atgtggattc tgctgatgcg gaggaggatg actcggatgt ctggtggggc    780

ggagcagaca cagactatgc agatgggagt gaagacaaag tagtagaagt agcagaggag    840

gaagaagtgg ctgaggtgga agaagaagaa gccgatgatg acgaggacga tgaggatggt    900

gatgaggtag aggaagaggc tgaggaaccc tacgaagaag ccacagagag aaccaccagc    960

attgccacca ccaccaccac caccacagag tctgtggaag aggtggttcg agttcctaca   1020

acagcagcca gtacccctga tgccgttgac aagtatctcg agacacctgg ggatgagaat   1080

gaacatgccc atttccagaa agccaaagag aggcttgagg ccaagcaccg agagagaatg   1140

tcccaggtca tgagagaatg ggaagaggca gaacgtcaag caaagaactt gcctaaagct   1200

gataagaagg cagttatcca gcatttccag gagaaagtgg aatctttgga acaggaagca   1260

gccaacgaga gacagcagct ggtggagaca cacatggcca gagtggaagc catgctcaat   1320

gaccgccgcc gcctggccct ggagaactac atcaccgctc tgcaggctgt tcctcctcgg   1380

cctcgtcacg tgttcaatat gctaaagaag tatgtccgcg cagaacagaa ggacagacag   1440

cacaccctaa agcatttcga gcatgtgcgc atggtggatc ccaagaaagc cgctcagatc   1500

cggtcccagg ttatgacaca cctccgtgtg atttatgagc gcatgaatca gtctctctcc   1560

ctgctctaca acgtgcctgc agtggccgag gagattcagg atgaagttga tgagctgctt   1620

cagaaagagc aaaactattc agatgacgtc ttggccaaca tgattagtga accaaggatc   1680

agttacggaa acgatgctct catgccatct ttgaccgaaa cgaaaaccac cgtggagctc   1740
```

-continued

```
cttcccgtga atggagagtt cagcctggac gatctccagc cgtggcattc ttttggggct   1800
gactctgtgc cagccaacac agaaaacgaa gttgagcctg ttgatgcccg ccctgctgcc   1860
gaccgaggac tgaccactcg accaggttct gggttgacaa atatcaagac ggaggagatc   1920
tctgaagtga agatggatgc agaattccga catgactcag gatatgaagt tcatcatcaa   1980
aaattggtgt tctttgcaga agatgtgggt tcaaacaaag gtgcaatcat tggactcatg   2040
gtgggcggtg ttgtcatagc gacagtgatc gtcatcacct tggtgatgct gaagaagaaa   2100
cagtacacat ccattcatca tggtgtggtg gaggttgacg ccgctgtcac cccagaggag   2160
cgccacctgt ccaagatgca gcagaacggc tacgaaaatc caacctacaa gttctttgag   2220
cagatgcaga actagacccc cgccacagca gcctctgaag ttggacagca aaaccattgc   2280
ttcactaccc atcggtgtcc atttatagaa taatgtggga agaaacaaac ccgttttatg   2340
atttactcat tatcgccttt tgacagctgt gctgtaacac aagtagatgc ctgaacttga   2400
attaatccac acatcagtaa tgtattctat ctctctttac attttggtct ctatactaca   2460
ttattaatgg gttttgtgta ctgtaaagaa tttagctgta tcaaactagt gcatgaatag   2520
attctctcct gattatttat cacatagccc cttagccagt tgtatattat tcttgtggtt   2580
tgtgacccaa ttaagtccta ctttacatat gctttaagaa tcgatggggg atgcttcatg   2640
tgaacgtggg agttcagctg cttctcttgc ctaagtattc ctttcctgat cactatgcat   2700
tttaaagtta aacattttta agtatttcag atgctttaga gagatttttt ttccatgact   2760
gcattttact gtacagattg ctgcttctgc tatatttgtg atataggaat taagaggata   2820
cacacgtttg tttcttcgtg cctgttttat gtgcacacat taggcattga gacttcaagc   2880
ttttcttttt ttgtccacgt atctttgggt ctttgataaa gaaaagaatc cctgttcatt   2940
gtaagcactt ttacggggcg ggtggggagg ggtgctctgc tggtcttcaa ttaccaagaa   3000
ttctccaaaa caattttctg caggatgatt gtacagaatc attgcttatg acatgatcgc   3060
tttctacact gtattacata aataaattaa ataaaataac cccgggcaag acttttcttt   3120
gaaggatgac tacagacatt aaataatcga agtaattttg ggtggggaga agaggcagat   3180
tcaattttct ttaaccagtc tgaagtttca tttatgatac aaaagaagat gaaaatggaa   3240
gtggcaatat aaggggatga ggaaggcatg cctggacaaa cccttctttt aagatgtgtc   3300
ttcaatttgt ataaaatggt gttttcatgt aaataaatac attcttggag gagc         3354
```

<210> SEQ ID NO 10
<211> LENGTH: 8331
<212> TYPE: DNA
<213> ORGANISM: Artificial
<220> FEATURE:
<223> OTHER INFORMATION: recombinant plasmid

<400> SEQUENCE: 10

```
acgaaagggc ctcgtgatac gcctattttt ataggttaat gtcatgataa taatggtttc     60
ttaggacgga tcgcttgcct gtaacttaca cgcgcctcgt atcttttaat gatggaataa    120
tttgggaatt tactctgtgt ttatttattt ttatgttttg tatttggatt ttagaaagta    180
aataaagaag gtagaagagt tacggaatga agaaaaaaaa ataaacaaag gtttaaaaaa    240
tttcaacaaa aagcgtactt tacatatata tttattagac aagaaaagca gattaaatag    300
atatacattc gattaacgat aagtaaaatg taaaatcaca ggattttcgt gtgtggtctt    360
ctacacagac aagatgaaac aattcggcat taatacctga gagcaggaag agcaagataa    420
```

-continued

```
aaggtagtat ttgttggcga tccccctaga gtcttttaca tcttcggaaa acaaaaacta    480
tttttctttt aatttctttt tttactttct atttttaatt tatatattta tattaaaaaa    540
tttaaattat aattattttt atagcacgtg atgaaaagga cccaggtggc acttttcggg    600
gaaatgtgcg cggaacccct atttgtttat ttttctaaat acattcaaat atgtatccgc    660
tcatgagaca ataaccctga taaatgcttc aataatctgc agctctggcc cgtgtctcaa    720
aatctctgat gttacattgc acaagataaa aatatatcat catgaacaat aaaactgtct    780
gcttacataa acagtaatac aaggggtgtt atgagccata ttcaacggga aacgtcttgc    840
tggaggccgc gattaaattc caacatggat gctgatttat atgggtataa atgggctcgc    900
gataatgtcg ggcaatcagg tgcgacaatc tttcgattgt atgggaagcc cgatgcgcca    960
gagttgtttc tgaaacatgg caaaggtagc gttgccaatg atgttacaga tgagatggtc   1020
agactaaact ggctgacgga atttatgcct cttccgacca tcaagcattt tatccgtact   1080
cctgatgatg catggttact caccactgcg atccgcggga aaacagcatt ccaggtatta   1140
gaagaatatc ctgattcagg tgaaaatatt gttgatgcgc tggcagtgtt cctgcgccgg   1200
ttgcattcga ttcctgtttg taattgtcct tttaacagcg atcgcgtatt tcgtctcgct   1260
caggcgcaat cacgaatgaa taacggtttg gttgatgcga gtgattttga tgacgagcgt   1320
aatggctggc ctgttgaaca agtctggaaa gaaatgcata cgcttttgcc attctcaccg   1380
gattcagtcg tcactcatgg tgatttctca cttgataacc ttatttttga cgaggggaaa   1440
ttaataggtt gtattgatgt tggacgagtc ggaatcgcag accgatacca ggatcttgcc   1500
atcctatgga actgcctcgg tgagttttct ccttcattac agaaacggct ttttcaaaaa   1560
tatggtattg ataatcctga tatgaataaa ttgcagtttc atttgatgct cgatgagttt   1620
ttctaatcag aattggttaa ttggttgtaa cactggcaga gcattacgct gacttgacgg   1680
gacggcgcat gaccaaaatc ccttaacgtg agttttcgtt ccactgagcg tcagaccccg   1740
tagaaaagat caaaggatct tcttgagatc cttttttct gcgcgtaatc tgctgcttgc    1800
aaacaaaaaa accaccgcta ccagcggtgg tttgtttgcc ggatcaagag ctaccaactc   1860
tttttccgaa ggtaactggc ttcagcagag cgcagatacc aaatactgtc cttctagtgt   1920
agccgtagtt aggccaccac ttcaagaact ctgtagcacc gcctacatac ctcgctctgc   1980
taatcctgtt accagtggct gctgccagtg gcgataagtc gtgtcttacc gggttggact   2040
caagacgata gttaccggat aaggcgcagc ggtcgggctg aacggggggt tcgtgcacac   2100
agcccagctt ggagcgaacg acctacaccg aactgagata cctacagcgt gagcattgag   2160
aaagcgccac gcttcccgaa gggagaaagg cggacaggta tccggtaagc ggcagggtcg   2220
gaacaggaga gcgcacgagg gagcttccag ggggaaacgc ctggtatctt tatagtcctg   2280
tcgggtttcg ccacctctga cttgagcgtc gatttttgtg atgctcgtca ggggggccga   2340
gcctatggaa aaacgccagc aacgcggcct ttttacggtt cctggccttt tgctggcctt   2400
ttgctcacat gttctttcct gcgttatccc ctgattctgt ggataaccgt attaccgcct   2460
ttgagtgagc tgataccgct cgccgcagcc gaacgaccga gcgcagcgag tcagtgagcg   2520
aggaagcgga agagcgccca atacgcaaac cgcctctccc cgcgcgttgg ccgattcatt   2580
aatgcagctg gcacgacagg tttcccgact ggaaagcggg cagtgagcgc aacgcaatta   2640
atgtgagtta cctcactcat taggcacccc aggctttaca ctttatgctt ccggctccta   2700
tgttgtgtgg aattgtgagc ggataacaat ttcacacagg aaacagctat gaccatgatt   2760
acgccaagct cggaattaac cctcactaaa gggaacaaaa gctggtaccg atcccgagct   2820
```

-continued

```
ttgcaaatta aagccttcga gcgtcccaaa accttctcaa gcaaggtttt cagtataatg   2880
ttacatgcgt acacgcgtct gtacagaaaa aaaagaaaaa tttgaaatat aaataacgtt   2940
cttaatacta acataactat aaaaaaataa atagggacct agacttcagg ttgtctaact   3000
ccttcctttt cggttagagc ggatgtgggg ggagggcgtg aatgtaagcg tgacataact   3060
aattacatga tatcgacaaa ggaaaagggg cctgtttact cacaggcttt tttcaagtag   3120
gtaattaagt cgtttctgtc tttttccttc ttcaacccac caaaggccat cttggtactt   3180
tttttttttt tttttttttt tttttttttt tttttttttt tttttttttt tttttttttt   3240
tttttttttt tttttttttt tttttttttt ttcatagaaa taatacagaa gtagatgttg   3300
aattagatta aactgaagat atataattta ttggaaaata catagagctt tttgttgatg   3360
cgcttaagcg atcaattcaa caacaccacc agcagctctg atttttttctt cagccaactt   3420
ggagacgaat ctagctttga cgataactgg aacatttgga attctaccct tacccaagat   3480
cttaccgtaa ccggctgcca aagtgtcaat aactggagca gtttccttag aagcagattt   3540
caagtattgg tctctcttgt cttctgggat caatgtccac aatttgtcca agttcaagac   3600
tggcttccag aaatgagctt gttgcttgtg gaagtatctc ataccaacct taccgaaata   3660
acctggatgg tatttatcca tgttaattct gtggtgatgt tgaccaccgg ccatacctct   3720
accaccgggg tgctttctgt gcttaccgat acgaccttta ccggctgaga cgtgacctct   3780
gtgctttcta gtcttagtga atctggaagg cattcttgat tagttggatg attgttctgg   3840
gatttaatgc aaaaatcact taagaaggaa aatcaacgga gaaagcaaac gccatcttaa   3900
atatacggga tacagatgaa agggtttgaa cctatctgga aaatagcatt aaacaagcga   3960
aaaactgcga ggaaaattgt ttgcgtctct gcgggctatt cacgcgccag aggaaaatag   4020
gaaaaataac agggcattag aaaaataatt ttgattttgg taatgtgtgg gtcctggtgt   4080
acagatgtta cattggttac agtactcttg tttttgctgt gtttttcgat gaatctccaa   4140
aatggttgtt agcacatgga agagtcaccg atgctaagtt atctctatgt aagctacgtg   4200
gcgtgacttt tgatgaagcc gcacaagaga tacaggattg gcaactgcaa atagaatctg   4260
gggatccccc ctcgacggat gcaagggttc gaatccctta gctctcatta tttttttgctt   4320
tttctcttga ggtsgtcaca tgatcgcaaa atggcaaatg gcacgtgaag ctgtcgatat   4380
tggggaactg tggtggttgg caaatgacta attaagttag tcaaggcgcc atcctcatga   4440
aaactgtgta acataataac cgaagtgtcg aaaaggtggc accttgtcca attgaacacg   4500
ctcgatgaaa aaaataagat atatataagg ttaagtaaag cgtctgttag aaaggaagtt   4560
tttccttttt cttgctctct tgtcttttca tctactattt ccttcgtgta atacagggtc   4620
gtcagataca tagatacaat tctattaccc ccatccatac atctagaact agtggatccc   4680
ccgggctgca ggaattcgat atcaagcttc acagctagcg cactcggtgc cccgcgcagg   4740
gtcgcgatgc tgcccggttt ggcactgttc ctgctggccg cctggacggc tcgggcgctg   4800
gatgcagaat tccgacatga ctcaggatat gaagttcatc atcaaaaaatt ggtgttcttt   4860
gcagaagatg tgggttcaaa caaaggtgca atcattggac tcatggtggg cggtgttgtc   4920
atagcgacag tgatcgtcat caccttggtg atgctgaaga agaaacagta cacatccatt   4980
catcatggtg tggtggaggt tgacgccgct gtcaccccag aggagcgcca cctgtccaag   5040
atgcagcaga acggctacga aaatccaacc tacaagttct ttgagcagat gcagaacgcg   5100
cggggtaccc cggcgatgaa gctactgtct tctatcgaac aagcatgcga tatttgccga   5160
```

-continued

```
cttaaaaagc tcaagtgctc caaagaaaaa ccgaagtgcg ccaagtgtct gaagaacaac   5220
tgggagtgtc gctactctcc caaaaccaaa aggtctccgc tgactagggc acatctgaca   5280
gaagtggaat caaggctaga aagactggaa cagctatttc tactgatttt tcctcgagaa   5340
gaccttgaca tgattttgaa aatggattct ttacaggata taaaagcatt gttaacagga   5400
ttatttgtac aagataatgt gaataaagat gccgtcacag atagattggc ttcagtggag   5460
actgatatgc ctctaacatt gagacagcat agaataagtg cgacatcatc atcggaagag   5520
agtagtaaca aaggtcaaag acagttgact gtatcgccgg aattcccggg gatctgggcc   5580
cccccgaccg atgtcagcct gggggacgag ctccacttag acggcgagga cgtggcgatg   5640
gcgcatgccg acgcgctaga cgatttcgat ctggacatgt tgggggacgg ggattccccg   5700
gggccgggat ttacccccca cgactccgcc ccctacggcg ctctggatat ggccgacttc   5760
gagtttgagc agatgtttac cgatgccctt ggaattgacg agtacggtgg gtagggatcc   5820
actagtccag tgtggtggaa ttctgcagat atccagcaca gtggcggccg ctcgaccccg   5880
ggtgctagca aggccttgtg gccagccatg gcaactagtg cggccgctaa gtaagtaaga   5940
cgtcgagctc taagtaagta acggccgcca ccgcggtgga gctttggact tcttcgccag   6000
aggtttggtc aagtctccaa tcaaggttgt cggcttgtct accttgccag aaatttacga   6060
aaagatggaa aagggtcaaa tcgttggtag atacgttgtt gacacttcta aataagcgaa   6120
tttcttatga tttatgattt ttattattaa ataagttata aaaaaaataa gtgtatacaa   6180
attttaaagt gactcttagg ttttaaaacg aaaattcttg ttcttgagta actctttcct   6240
gtaggtcagg ttgctttctc aggtatagca tgaggtcgct cttattgacc acacctctac   6300
cggcatgccg agcaaatgcc tgcaaatcgc tccccatttc acccaattgt agatatgcta   6360
actccagcaa tgagttgatg aatctcggtg tgtattttat gtcctcagag gacaatacct   6420
gttgtaatcg ttcttccaca cggatcccaa ttcgccctat agtgagtcgt attacaattc   6480
actggccgtc gttttacaac gtcgtgactg ggaaaaccct ggcgttaccc aacttaatcg   6540
ccttgcagca catccccctt tcgccagctg gcgtaatagc gaagaggccc gcaccgatcg   6600
cccttcccaa cagttgcgca gcctgaatgg cgaatggacg cgccctgtag cggcgcatta   6660
agcgcggcgg gtgtggtggt tacgcgcagc gtgaccgcta cacttgccag cgccctagcg   6720
cccgctcctt tcgctttctt cccttccttt ctcgccacgt tcgccggctt tccccgtcaa   6780
gctctaaatc gggggctccc tttagggttc cgatttagtg ctttacggca cctcgacccc   6840
aaaaaacttg attagggtga tggttcacgt agtgggccat cgccctgata gacggttttt   6900
cgccctttga cgttggagtc cacgttcttt aatagtggac tcttgttcca aactggaaca   6960
acactcaacc ctatctcggt ctattctttt gatttataag ggattttgcc gatttcggcc   7020
tattggttaa aaaatgagct gatttaacaa aaatttaacg cgaattttaa caaaatatta   7080
acgtttacaa tttcctgatg cggtattttc tccttacgca tctgtgcggt atttcacacc   7140
gcaggcaagt gcacaaacaa tacttaaata aatactactc agtaataacc tatttcttag   7200
catttttgac gaaatttgct attttgttag agtcttttac accatttgtc tccacacctc   7260
cgcttacatc aacaccaata acgccattta atctaagcgc atcaccaaca ttttctggcg   7320
tcagtccacc agctaacata aaatgtaagc tttcggggct ctcttgcctt ccaacccagt   7380
cagaaatcga gttccaatcc aaaagttcac ctgtcccacc tgcttctgaa tcaaacaagg   7440
gaataaacga atgaggtttc tgtgaagctg cactgagtag tatgttgcag tcttttggaa   7500
atacgagtct tttaataact ggcaaaccga ggaactcttg gtattcttgc cacgactcat   7560
```

-continued

```
ctccatgcag ttggacgata tcaatgccgt aatcattgac cagagccaaa acatcctcct   7620

taggttgatt acgaaacacg ccaaccaagt atttcggagt gcctgaacta tttttatatg   7680

cttttacaag acttgaaatt ttccttgcaa taaccgggtc aattgttctc tttctattgg   7740

gcacacatat aatacccagc aagtcagcat cggaatctag agcacattct gcggcctctg   7800

tgctctgcaa gccgcaaact ttcaccaatg gaccagaact acctgtgaaa ttaataacag   7860

acatactcca agctgccttt gtgtgcttaa tcacgtatac tcacgtgctc aatagtcacc   7920

aatgccctcc ctcttggccc tctccttttc tttttcgac cgaattaatt cttaatcggc    7980

aaaaaaagaa aagctccgga tcaagattgt acgtaaggtg acaagctatt tttcaataaa   8040

gaatatcttc cactactgcc atctggcgtc ataactgcaa agtacacata tattacgatg   8100

ctgtctatta aatgcttcct atattatata tatagtaatg tcgtttatgg tgcactctca   8160

gtacaatctg ctctgatgcc gcatagttaa gccagccccg acacccgcca acacccgctg   8220

acgcgccctg acgggcttgt ctgctcccgg catccgctta cagacaagct gtgaccgtct   8280

ccgggagctg catgtgtcag aggttttcac cgtcatcacc gaaacgcgcg a            8331


<210> SEQ ID NO 11
<211> LENGTH: 355
<212> TYPE: PRT
<213> ORGANISM: Artificial
<220> FEATURE:
<223> OTHER INFORMATION: Mutein

<400> SEQUENCE: 11

Met Leu Pro Gly Leu Ala Leu Phe Leu Leu Ala Ala Trp Thr Ala Arg
1               5                   10                  15

Ala Leu Asp Ala Glu Phe Arg His Asp Ser Gly Tyr Glu Val His His
            20                  25                  30

Gln Lys Leu Val Phe Phe Ala Glu Asp Val Gly Ser Asn Lys Gly Ala
        35                  40                  45

Ile Ile Gly Leu Met Val Gly Gly Val Val Ile Ala Thr Val Ile Val
    50                  55                  60

Ile Thr Leu Val Met Leu Lys Lys Lys Gln Tyr Thr Ser Ile His His
65                  70                  75                  80

Gly Val Val Glu Val Asp Ala Ala Val Thr Pro Glu Glu Arg His Leu
                85                  90                  95

Ser Lys Met Gln Gln Asn Gly Tyr Glu Asn Pro Thr Tyr Lys Phe Phe
            100                 105                 110

Glu Gln Met Gln Asn Ala Arg Gly Thr Pro Ala Met Lys Leu Leu Ser
        115                 120                 125

Ser Ile Glu Gln Ala Cys Asp Ile Cys Arg Leu Lys Lys Leu Lys Cys
    130                 135                 140

Ser Lys Glu Lys Pro Lys Cys Ala Lys Cys Leu Lys Asn Asn Trp Glu
145                 150                 155                 160

Cys Arg Tyr Ser Pro Lys Thr Lys Arg Ser Pro Leu Thr Arg Ala His
                165                 170                 175

Leu Thr Glu Val Glu Ser Arg Leu Glu Arg Leu Glu Gln Leu Phe Leu
            180                 185                 190

Leu Ile Phe Pro Arg Glu Asp Leu Asp Met Ile Leu Lys Met Asp Ser
        195                 200                 205

Leu Gln Asp Ile Lys Ala Leu Leu Thr Gly Leu Phe Val Gln Asp Asn
    210                 215                 220
```

-continued

```
Val Asn Lys Asp Ala Val Thr Asp Arg Leu Ala Ser Val Glu Thr Asp
225                 230                 235                 240

Met Pro Leu Thr Leu Arg Gln His Arg Ile Ser Ala Thr Ser Ser Ser
                245                 250                 255

Glu Glu Ser Ser Asn Lys Gly Gln Arg Gln Leu Thr Val Ser Pro Glu
            260                 265                 270

Phe Pro Gly Ile Trp Ala Pro Pro Thr Asp Val Ser Leu Gly Asp Glu
        275                 280                 285

Leu His Leu Asp Gly Glu Asp Val Ala Met Ala His Ala Asp Ala Leu
    290                 295                 300

Asp Asp Phe Asp Leu Asp Met Leu Gly Asp Gly Asp Ser Pro Gly Pro
305                 310                 315                 320

Gly Phe Thr Pro His Asp Ser Ala Pro Tyr Gly Ala Leu Asp Met Ala
                325                 330                 335

Asp Phe Glu Phe Glu Gln Met Phe Thr Asp Ala Leu Gly Ile Asp Glu
            340                 345                 350

Tyr Gly Gly
        355


<210> SEQ ID NO 12
<211> LENGTH: 22
<212> TYPE: PRT
<213> ORGANISM: Saccharomyces cerevisiae

<400> SEQUENCE: 12

Met Leu Leu Arg Ala Phe Leu Phe Leu Leu Ala Gly Phe Ala Ala Lys
1               5                   10                  15

Ile Ser Ala Ala Leu Ala
            20


<210> SEQ ID NO 13
<211> LENGTH: 17
<212> TYPE: PRT
<213> ORGANISM: Artificial
<220> FEATURE:
<223> OTHER INFORMATION: signal peptide

<400> SEQUENCE: 13

Met Arg Ala Trp Ile Phe Phe Leu Leu Cys Leu Ala Gly Arg Ala Leu
1               5                   10                  15

Ala


<210> SEQ ID NO 14
<211> LENGTH: 308
<212> TYPE: PRT
<213> ORGANISM: Artificial
<220> FEATURE:
<223> OTHER INFORMATION: Mutein

<400> SEQUENCE: 14

Met Leu Pro Gly Leu Ala Leu Phe Leu Leu Ala Ala Trp Thr Ala Arg
1               5                   10                  15

Ala Leu Asp Ala Glu Phe Arg His Asp Ser Gly Tyr Glu Val His His
            20                  25                  30

Gln Lys Leu Val Phe Phe Ala Glu Asp Val Gly Ser Asn Lys Gly Ala
        35                  40                  45

Ile Ile Gly Leu Met Val Gly Gly Val Val Ile Ala Thr Val Ile Val
    50                  55                  60

Ile Thr Leu Val Met Leu Lys Lys Lys Gly Arg Ser Gly Lys Leu Leu
```

-continued

```
65                  70                  75                  80

Ser Ser Ile Glu Gln Ala Cys Asp Ile Cys Arg Leu Lys Lys Leu Lys
                85                  90                  95

Cys Ser Lys Glu Lys Pro Lys Cys Ala Lys Cys Leu Lys Asn Asn Trp
            100                 105                 110

Glu Cys Arg Tyr Ser Pro Lys Thr Lys Arg Ser Pro Leu Thr Arg Ala
        115                 120                 125

His Leu Thr Glu Val Glu Ser Arg Leu Glu Arg Leu Glu Gln Leu Phe
    130                 135                 140

Leu Leu Ile Phe Pro Arg Glu Asp Leu Asp Met Ile Leu Lys Met Asp
145                 150                 155                 160

Ser Leu Gln Asp Ile Lys Ala Leu Leu Thr Gly Leu Phe Val Gln Asp
                165                 170                 175

Asn Val Asn Lys Asp Ala Val Thr Asp Arg Leu Ala Ser Val Glu Thr
            180                 185                 190

Asp Met Pro Leu Thr Leu Arg Gln His Arg Ile Ser Ala Thr Ser Ser
        195                 200                 205

Ser Glu Glu Ser Ser Asn Lys Gly Gln Arg Gln Leu Thr Val Ser Pro
    210                 215                 220

Glu Phe Pro Gly Ile Trp Ala Pro Pro Thr Asp Val Ser Leu Gly Asp
225                 230                 235                 240

Glu Leu His Leu Asp Gly Glu Asp Val Ala Met Ala His Ala Asp Ala
                245                 250                 255

Leu Asp Asp Phe Asp Leu Asp Met Leu Gly Asp Gly Asp Ser Pro Gly
            260                 265                 270

Pro Gly Phe Thr Pro His Asp Ser Ala Pro Tyr Gly Ala Leu Asp Met
        275                 280                 285

Ala Asp Phe Glu Phe Glu Gln Met Phe Thr Asp Ala Leu Gly Ile Asp
    290                 295                 300

Glu Tyr Gly Gly
305
```

<210> SEQ ID NO 15
<211> LENGTH: 6454
<212> TYPE: DNA
<213> ORGANISM: Artificial
<220> FEATURE:
<223> OTHER INFORMATION: Mutagen

<400> SEQUENCE: 15

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660
```

-continued

```
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttaact ggcttatcga aattaatacg actcactata gggagaccca agcttctgcc    900
tgccgcctgc ctgcctgcca ctgagggttc ccagcaccat gagggcctgg atcttctttc    960
tcctttgcct ggccgggagg gctctggcag ccccgctagc tgatgcagaa ttccgacatg   1020
actcaggata tgaagttcat catcaaaaat tggtgttctt tgcagaagat gtgggttcaa   1080
acaaaggtgc aatcattgga ctcatggtgg gcggtgttgt catagcgaca gtgatcgtca   1140
tcaccttggt gatgctgaag aagaaaggta gatctggcaa gctactgtct tctatcgaac   1200
aagcatgcga tatttgccga cttaaaaagc tcaagtgctc caaagaaaaa ccgaagtgcg   1260
ccaagtgtct gaagaacaac tgggagtgtc gctactctcc caaaaccaaa aggtctccgc   1320
tgactagggc acatctgaca gaagtggaat caaggctaga aagactggaa cagctatttc   1380
tactgatttt tcctcgagaa gaccttgaca tgattttgaa aatggattct ttacaggata   1440
taaaagcatt gttaacagga ttatttgtac aagataatgt gaataaagat gccgtcacag   1500
atagattggc ttcagtggag actgatatgc ctctaacatt gagacagcat agaataagtg   1560
cgacatcatc atcggaagag agtagtaaca aaggtcaaag acagttgact gtatcgccgg   1620
aattcccggg gatctgggcc cccccgaccg atgtcagcct gggggacgag ctccacttag   1680
acggcgagga cgtggcgatg gcgcatgccg acgcgctaga cgatttcgat ctggacatgt   1740
tgggggacgg ggattccccg ggtccgggat ttacccccca cgactccgcc ccctacggcg   1800
ctctggatat ggccgacttc gagtttgagc agatgtttac cgatgccctt ggaattgacg   1860
agtacggtgg gggttagaaa atcgataccg tcgaggccgc tcgagcatgc atctagaggg   1920
ccctattcta tagtgtcacc taaatgctag agctcgctga tcagcctcga ctgtgccttc   1980
tagttgccag ccatctgttg tttgcccctc ccccgtgcct tccttgaccc tggaaggtgc   2040
cactcccact gtcctttcct aataaaatga ggaaattgca tcgcattgtc tgagtaggtg   2100
tcattctatt ctggggggtg gggtggggca ggacagcaag ggggaggatt gggaagacaa   2160
tagcaggcat gctggggatg cggtgggctc tatggaacca gctggggctc gagggggggat   2220
ccccacgcgc cctgtagcgg cgcattaagc gcggcgggtg tggtggttac gcgcagcgtg   2280
accgctacac ttgccagcgc cctagcgccc gctcctttcg ctttcttccc ttcctttctc   2340
gccacgttcg ccggctttcc ccgtcaagct ctaaatcggg gcatcccttt agggttccga   2400
tttagtgctt tacggcacct cgaccccaaa aaacttgatt agggtgatgg ttcacgtagt   2460
gggccatcgc cctgatagac ggtttttcgc cctttgacgt tggagtccac gttctttaat   2520
agtggactct tgttccaaac tggaacaaca ctcaacccta tctcggtcta ttcttttgat   2580
ttataaggga ttttggggat ttcggcctat tggttaaaaa atgagctgat ttaacaaaaa   2640
tttaacgcga attttaacaa aatattaacg tttacaattt aaatatttgc ttatacaatc   2700
ttcctgtttt tggggctttt ctgattatca accggggtgg gtaccgagct cgaattctgt   2760
ggaatgtgtg tcagttaggg tgtggaaagt ccccaggctc cccaggcagg cagaagtatg   2820
caaagcatgc atctcaatta gtcagcaacc aggtgtggaa agtccccagg ctccccagca   2880
ggcagaagta tgcaaagcat gcatctcaat tagtcagcaa ccatagtccc gcccctaact   2940
ccgcccatcc cgcccctaac tccgcccagt tccgcccatt ctccgcccca tggctgacta   3000
atttttttta tttatgcaga ggccgaggcc gcctcggcct ctgagctatt ccagaagtag   3060
```

-continued

```
tgaggaggct tttttggagg cctaggcttt tgcaaaaagc tcccgggagc ttggatatcc   3120
attttcggat ctgatcaaga gacaggatga ggatcgtttc gcatgattga acaagatgga   3180
ttgcacgcag gttctccggc cgcttgggtg gagaggctat tcggctatga ctgggcacaa   3240
cagacaatcg gctgctctga tgccgccgtg ttccggctgt cagcgcaggg gcgcccggtt   3300
ctttttgtca agaccgacct gtccggtgcc ctgaatgaac tgcaggacga ggcagcgcgg   3360
ctatcgtggc tggccacgac gggcgttcct tgcgcagctg tgctcgacgt tgtcactgaa   3420
gcgggaaggg actggctgct attgggcgaa gtgccggggc aggatctcct gtcatctcac   3480
cttgctcctg ccgagaaagt atccatcatg gctgatgcaa tgcggcggct gcatacgctt   3540
gatccggcta cctgcccatt cgaccaccaa gcgaaacatc gcatcgagcg agcacgtact   3600
cggatggaag ccggtcttgt cgatcaggat gatctggacg aagagcatca ggggctcgcg   3660
ccagccgaac tgttcgccag gctcaaggcg cgcatgcccg acggcgagga tctcgtcgtg   3720
acccatggcg atgcctgctt gccgaatatc atggtggaaa atggccgctt ttctggattc   3780
atcgactgtg gccggctggg tgtggcggac cgctatcagg acatagcgtt ggctacccgt   3840
gatattgctg aagagcttgg cggcgaatgg gctgaccgct tcctcgtgct ttacggtatc   3900
gccgctcccg attcgcagcg catcgccttc tatcgccttc ttgacgagtt cttctgagcg   3960
ggactctggg gttcgaaatg accgaccaag cgacgcccaa cctgccatca cgagatttcg   4020
attccaccgc cgccttctat gaaaggttgg gcttcggaat cgttttccgg gacgccggct   4080
ggatgatcct ccagcgcggg gatctcatgc tggagttctt cgcccacccc aacttgttta   4140
ttgcagctta taatggttac aaataaagca atagcatcac aaatttcaca aataaagcat   4200
tttttcact gcattctagt tgtggtttgt ccaaactcat caatgtatct tatcatgtct   4260
ggatcccgtc gacctcgaga gcttggcgta atcatggtca tagctgtttc ctgtgtgaaa   4320
ttgttatccg ctcacaattc cacacaacat acgagccgga agcataaagt gtaaagcctg   4380
gggtgcctaa tgagtgagct aactcacatt aattgcgttg cgctcactgc ccgctttcca   4440
gtcgggaaac ctgtcgtgcc agctgcatta atgaatcggc caacgcgcgg ggagaggcgg   4500
tttgcgtatt gggcgctctt ccgcttcctc gctcactgac tcgctgcgct cggtcgttcg   4560
gctgcggcga gcggtatcag ctcactcaaa ggcggtaata cggttatcca cagaatcagg   4620
ggataacgca ggaaagaaca tgtgagcaaa aggccagcaa aaggccagga accgtaaaaa   4680
ggccgcgttg ctggcgtttt tccataggct ccgcccccct gacgagcatc acaaaaatcg   4740
acgctcaagt cagaggtggc gaaacccgac aggactataa agataccagg cgtttccccc   4800
tggaagctcc ctcgtgcgct ctcctgttcc gaccctgccg cttaccggat acctgtccgc   4860
ctttctccct tcgggaagcg tggcgctttc tcaatgctca cgctgtaggt atctcagttc   4920
ggtgtaggtc gttcgctcca agctgggctg tgtgcacgaa ccccccgttc agcccgaccg   4980
ctgcgcctta tccggtaact atcgtcttga gtccaacccg gtaagacacg acttatcgcc   5040
actggcagca gccactggta acaggattag cagagcgagg tatgtaggcg gtgctacaga   5100
gttcttgaag tggtggccta actacggcta cactagaagg acagtatttg gtatctgcgc   5160
tctgctgaag ccagttacct tcggaaaaag agttggtagc tcttgatccg gcaaacaaac   5220
caccgctggt agcggtggtt tttttgtttg caagcagcag attacgcgca gaaaaaaagg   5280
atctcaagaa gatcctttga tcttttctac ggggtctgac gctcagtgga acgaaaactc   5340
acgttaaggg attttggtca tgagattatc aaaaaggatc ttcacctaga tcctttttaaa   5400
```

-continued ttaaaaatga agttttaaat caatctaaag tatatatgag taaacttggt ctgacagtta 5460
ccaatgctta atcagtgagg cacctatctc agcgatctgt ctatttcgtt catccatagt 5520
tgcctgactc cccgtcgtgt agataactac gatacgggag ggcttaccat ctggccccag 5580
tgctgcaatg ataccgcgag acccacgctc accggctcca gatttatcag caataaacca 5640
gccagccgga agggccgagc gcagaagtgg tcctgcaact ttatccgcct ccatccagtc 5700
tattaattgt tgccgggaag ctagagtaag tagttcgcca gttaatagtt tgcgcaacgt 5760
tgttgccatt gctacaggca tcgtggtgtc acgctcgtcg tttggtatgg cttcattcag 5820
ctccggttcc caacgatcaa ggcgagttac atgatccccc atgttgtgca aaaaagcggt 5880
tagctccttc ggtcctccga tcgttgtcag aagtaagttg gccgcagtgt tatcactcat 5940
ggttatggca gcactgcata attctcttac tgtcatgcca tccgtaagat gcttttctgt 6000
gactggtgag tactcaacca agtcattctg agaatagtgt atgcggcgac cgagttgctc 6060
ttgcccggcg tcaatacggg ataataccgc gccacatagc agaactttaa aagtgctcat 6120
cattggaaaa cgttcttcgg ggcgaaaact ctcaaggatc ttaccgctgt tgagatccag 6180
ttcgatgtaa cccactcgtg cacccaactg atcttcagca tcttttactt tcaccagcgt 6240
ttctgggtga gcaaaaacag gaaggcaaaa tgccgcaaaa aagggaataa gggcgacacg 6300
gaaatgttga atactcatac tcttcctttt tcaatattat tgaagcattt atcagggtta 6360
ttgtctcatg agcggataca tatttgaatg tatttagaaa aataaacaaa taggggttcc 6420
gcgcacattt ccccgaaaag tgccacctga cgtc 6454

<210> SEQ ID NO 16
<211> LENGTH: 8259
<212> TYPE: DNA
<213> ORGANISM: Artificial
<220> FEATURE:
<223> OTHER INFORMATION: Recombinant plasmid

<400> SEQUENCE: 16
gacgaaaggg cctcgtgata cgcctatttt tataggttaa tgtcatgata ataatggttt 60
cttaggacgg atcgcttgcc tgtaacttac acgcgcctcg tatcttttaa tgatggaata 120
atttgggaat ttactctgtg tttatttatt tttatgtttt gtatttggat tttagaaagt 180
aaataaagaa ggtagaagag ttacggaatg aagaaaaaaa aataaacaaa ggtttaaaaa 240
atttcaacaa aaagcgtact ttacatatat atttattaga caagaaaagc agattaaata 300
gatatacatt cgattaacga taagtaaaat gtaaaatcac aggattttcg tgtgtggtct 360
tctacacaga caagatgaaa caattcggca ttaatacctg agagcaggaa gagcaagata 420
aaaggtagta tttgttggcg atccccctag agtcttttac atcttcggaa aacaaaaact 480
atttttcttt taatttcttt ttttactttc tatttttaat ttatatattt atattaaaaa 540
atttaaatta taattatttt tatagcacgt gatgaaaagg acccaggtgg cacttttcgg 600
ggaaatgtgc gcggaacccc tatttgttta tttttctaaa tacattcaaa tatgtatccg 660
ctcatgagac aataaccctg ataaatgctt caataatctg cagctctggc ccgtgtctca 720
aaatctctga tgttacattg cacaagataa aaatatatca tcatgaacaa taaaactgtc 780
tgcttacata aacagtaata caaggggtgt tatgagccat attcaacggg aaacgtcttg 840
ctggaggccg cgattaaatt ccaacatgga tgctgattta tatgggtata aatgggctcg 900
cgataatgtc gggcaatcag gtgcgacaat ctttcgattg tatgggaagc ccgatgcgcc 960
agagttgttt ctgaaacatg gcaaaggtag cgttgccaat gatgttacag atgagatggt 1020

-continued

```
cagactaaac tggctgacgg aatttatgcc tcttccgacc atcaagcatt ttatccgtac   1080
tcctgatgat gcatggttac tcaccactgc gatccgcggg aaaacagcat tccaggtatt   1140
agaagaatat cctgattcag gtgaaaatat tgttgatgcg ctggcagtgt tcctgcgccg   1200
gttgcattcg attcctgttt gtaattgtcc ttttaacagc gatcgcgtat ttcgtctcgc   1260
tcaggcgcaa tcacgaatga ataacggttt ggttgatgcg agtgattttg atgacgagcg   1320
taatggctgg cctgttgaac aagtctggaa agaaatgcat acgcttttgc cattctcacc   1380
ggattcagtc gtcactcatg gtgatttctc acttgataac cttatttttg acgaggggaa   1440
attaataggt tgtattgatg ttggacgagt cggaatcgca gaccgatacc aggatcttgc   1500
catcctatgg aactgcctcg gtgagttttc tccttcatta cagaaacggc tttttcaaaa   1560
atatggtatt gataatcctg atatgaataa attgcagttt catttgatgc tcgatgagtt   1620
tttctaatca gaattggtta attggttgta acactggcag agcattacgc tgacttgacg   1680
ggacggcgca tgaccaaaat cccttaacgt gagttttcgt tccactgagc gtcagacccc   1740
gtagaaaaga tcaaaggatc ttcttgagat cctttttttc tgcgcgtaat ctgctgcttg   1800
caaacaaaaa aaccaccgct accagcggtg gtttgtttgc cggatcaaga gctaccaact   1860
ctttttccga aggtaactgg cttcagcaga gcgcagatac caaatactgt ccttctagtg   1920
tagccgtagt taggccacca cttcaagaac tctgtagcac cgcctacata cctcgctctg   1980
ctaatcctgt taccagtggc tgctgccagt ggcgataagt cgtgtcttac cgggttggac   2040
tcaagacgat agttaccgga taaggcgcag cggtcgggct gaacgggggg ttcgtgcaca   2100
cagcccagct tggagcgaac gacctacacc gaactgagat acctacagcg tgagcattga   2160
gaaagcgcca cgcttcccga agggagaaag gcggacaggt atccggtaag cggcagggtc   2220
ggaacaggag agcgcacgag ggagcttcca gggggaaacg cctggtatct ttatagtcct   2280
gtcgggtttc gccacctctg acttgagcgt cgatttttgt gatgctcgtc aggggggccg   2340
agcctatgga aaaacgccag caacgcggcc tttttacggt tcctggcctt ttgctggcct   2400
tttgctcaca tgttctttcc tgcgttatcc cctgattctg tggataaccg tattaccgcc   2460
tttgagtgag ctgataccgc tcgccgcagc cgaacgaccg agcgcagcga gtcagtgagc   2520
gaggaagcgg aagagcgccc aatacgcaaa ccgcctctcc ccgcgcgttg gccgattcat   2580
taatgcagct ggcacgacag gtttcccgac tggaaagcgg gcagtgagcg caacgcaatt   2640
aatgtgagtt acctcactca ttaggcaccc caggctttac actttatgct tccggctcct   2700
atgttgtgtg gaattgtgag cggataacaa tttcacacag gaaacagcta tgaccatgat   2760
tacgccaagc tcggaattaa ccctcactaa agggaacaaa agctggtacc gatcccgagc   2820
tttgcaaatt aaagccttcg agcgtcccaa aaccttctca agcaaggttt tcagtataat   2880
gttacatgcg tacacgcgtc tgtacagaaa aaaaagaaaa atttgaaata taaataacgt   2940
tcttaatact aacataacta taaaaaaata aatagggacc tagacttcag gttgtctaac   3000
tccttccttt tcggttagag cggatgtggg gggagggcgt gaatgtaagc gtgacataac   3060
taattacatg atatcgacaa aggaaaaggg gcctgtttac tcacaggctt ttttcaagta   3120
ggtaattaag tcgtttctgt ctttttcctt cttcaaccca ccaaaggcca tcttggtact   3180
ttttttttt ttttttttt ttttttttt ttttttttt ttttttttt ttttttttt   3240
ttttttttt ttttttttt ttttttttt tttcatagaa ataatacaga agtagatgtt   3300
gaattagatt aaactgaaga tatataattt attggaaaat acatagagct ttttgttgat   3360
```

-continued

```
gcgcttaagc gatcaattca acaacaccac cagcagctct gatttttttct tcagccaact   3420
tggagacgaa tctagctttg acgataactg gaacatttgg aattctaccc ttacccaaga   3480
tcttaccgta accggctgcc aaagtgtcaa taactggagc agtttcctta gaagcagatt   3540
tcaagtattg gtctctcttg tcttctggga tcaatgtcca caatttgtcc aagttcaaga   3600
ctggcttcca gaaatgagct tgttgcttgt ggaagtatct cataccaacc ttaccgaaat   3660
aacctggatg gtatttatcc atgttaattc tgtggtgatg ttgaccaccg gccatacctc   3720
taccaccggg gtgctttctg tgcttaccga tacgaccttt accggctgag acgtgacctc   3780
tgtgctttct agtcttagtg aatctggaag gcattcttga ttagttggat gattgttctg   3840
ggatttaatg caaaaatcac ttaagaagga aaatcaacgg agaaagcaaa cgccatctta   3900
aatatacggg atacagatga aagggtttga acctatctgg aaaatagcat taaacaagcg   3960
aaaaactgcg aggaaaattg tttgcgtctc tgcgggctat tcacgcgcca gaggaaaata   4020
ggaaaaataa cagggcatta gaaaaataat tttgattttg gtaatgtgtg ggtcctggtg   4080
tacagatgtt acattggtta cagtactctt gtttttgctg tgtttttcga tgaatctcca   4140
aaatggttgt tagcacatgg aagagtcacc gatgctaagt tatctctatg taagctacgt   4200
ggcgtgactt ttgatgaagc cgcacaagag atacaggatt ggcaactgca aatagaatct   4260
ggggatcccc cctcgacgga tgcaagggtt cgaatccctt agctctcatt attttttgct   4320
ttttctcttg aggtcacatg atcgcaaaat ggcaaatggc acgtgaagct gtcgatattg   4380
gggaactgtg gtggttggca aatgactaat taagttagtc aaggcgccat cctcatgaaa   4440
actgtgtaac ataataaccg aagtgtcgaa aaggtggcac cttgtccaat tgaacacgct   4500
cgatgaaaaa aataagatat atataaggtt aagtaaagcg tctgttagaa aggaagtttt   4560
tcctttttct tgctctcttg tcttttcatc tactatttcc ttcgtgtaat acagggtcgt   4620
cagatacata gatacaattc tattaccccc atccatactc tagaatgctt ttgcgagctt   4680
tccttttcct cttggctggt tttgcagcca aaatatctgc agcgctagct gatgcagaat   4740
tccgacatga ctcaggatat gaagttcatc atcaaaaatt ggtgttcttt gcagaagatg   4800
tgggttcaaa caaaggtgca atcattggac tcatggtggg cggtgttgtc atagcgacag   4860
tgatcgtcat caccttggtg atgctgaaga agaaaggtag atctggcaag ctactgtctt   4920
ctatcgaaca agcatgcgat atttgccgac ttaaaaagct caagtgctcc aaagaaaaac   4980
cgaagtgcgc caagtgtctg aagaacaact gggagtgtcg ctactctccc aaaaccaaaa   5040
ggtctccgct gactagggca catctgacag aagtggaatc aaggctagaa agactggaac   5100
agctatttct actgattttt cctcgagaag accttgacat gattttgaaa atggattctt   5160
tacaggatat aaaagcattg ttaacaggat tatttgtaca agataatgtg aataaagatg   5220
ccgtcacaga tagattggct tcagtggaga ctgatatgcc tctaacattg agacagcata   5280
gaataagtgc gacatcatca tcggaagaga gtagtaacaa aggtcaaaga cagttgactg   5340
tatcgccgga attcccgggg atctgggccc ccccgaccga tgtcagcctg ggggacgagc   5400
tccacttaga cggcgaggac gtggcgatgg cgcatgccga cgcgctagac gatttcgatc   5460
tggacatgtt gggggacggg gattccccgg gtccgggatt taccccccac gactccgccc   5520
cctacggcgc tctggatatg gccgacttcg agtttgagca gatgtttacc gatgcccttg   5580
gaattgacga gtacggtggg ggtactagtg gccagtacac atccattcat catggtgtgg   5640
tggaggttga cgccgctgtc accccagagg agcgccacct gtccaagatg cagcagaacg   5700
gctacgaaaa tccaacctac aagttctttg agcagatgca gaacggcgcc tagggatccc   5760
```

-continued

```
ccgggctgca ggaattcgat atcaagctta tcgataccgt cgaccccggg tgctagcaag   5820
gccttgtggc cagccatggc aactagtgcg gccgctaagt aagtaagacg tcgagctcta   5880
agtaagtaac ggccgccacc gcggtggagc tttggacttc ttcgccagag gtttggtcaa   5940
gtctccaatc aaggttgtcg gcttgtctac cttgccagaa atttacgaaa agatggaaaa   6000
gggtcaaatc gttggtagat acgttgttga cacttctaaa taagcgaatt tcttatgatt   6060
tatgattttt attattaaat aagttataaa aaaaataagt gtatacaaat tttaaagtga   6120
ctcttaggtt ttaaaacgaa aattcttgtt cttgagtaac tctttcctgt aggtcaggtt   6180
gctttctcag gtatagcatg aggtcgctct tattgaccac acctctaccg gcatgccgag   6240
caaatgcctg caaatcgctc cccatttcac ccaattgtag atatgctaac tccagcaatg   6300
agttgatgaa tctcggtgtg tattttatgt cctcagagga caatacctgt tgtaatcgtt   6360
cttccacacg gatcccaatt cgccctatag tgagtcgtat tacaattcac tggccgtcgt   6420
tttacaacgt cgtgactggg aaaaccctgg cgttacccaa cttaatcgcc ttgcagcaca   6480
tccccctttc gccagctggc gtaatagcga agaggcccgc accgatcgcc cttcccaaca   6540
gttgcgcagc ctgaatggcg aatggacgcg ccctgtagcg gcgcattaag cgcggcgggt   6600
gtggtggtta cgcgcagcgt gaccgctaca cttgccagcg ccctagcgcc cgctcctttc   6660
gctttcttcc cttcctttct cgccacgttc gccggctttc cccgtcaagc tctaaatcgg   6720
gggctccctt tagggttccg atttagtgct ttacggcacc tcgaccccaa aaaacttgat   6780
tagggtgatg gttcacgtag tgggccatcg ccctgataga cggtttttcg ccctttgacg   6840
ttggagtcca cgttctttaa tagtggactc ttgttccaaa ctggaacaac actcaaccct   6900
atctcggtct attcttttga tttataaggg attttgccga tttcggccta ttggttaaaa   6960
aatgagctga tttaacaaaa atttaacgcg aattttaaca aaatattaac gtttacaatt   7020
tcctgatgcg gtattttctc cttacgcatc tgtgcggtat ttcacaccgc aggcaagtgc   7080
acaaacaata cttaaataaa tactactcag taataaccta tttcttagca tttttgacga   7140
aatttgctat tttgttagag tcttttacac catttgtctc cacacctccg cttacatcaa   7200
caccaataac gccatttaat ctaagcgcat caccaacatt ttctggcgtc agtccaccag   7260
ctaacataaa atgtaagctt tcggggctct cttgccttcc aacccagtca gaaatcgagt   7320
tccaatccaa aagttcacct gtcccacctg cttctgaatc aaacaaggga ataaacgaat   7380
gaggtttctg tgaagctgca ctgagtagta tgttgcagtc ttttggaaat acgagtcttt   7440
taataactgg caaaccgagg aactcttggt attcttgcca cgactcatct ccatgcagtt   7500
ggacgatatc aatgccgtaa tcattgacca gagccaaaac atcctcctta ggttgattac   7560
gaaacacgcc aaccaagtat ttcggagtgc ctgaactatt tttatatgct tttacaagac   7620
ttgaaatttt ccttgcaata accgggtcaa ttgttctctt tctattgggc acacatataa   7680
tacccagcaa gtcagcatcg gaatctagag cacattctgc ggcctctgtg ctctgcaagc   7740
cgcaaacttt caccaatgga ccagaactac ctgtgaaatt aataacagac atactccaag   7800
ctgcctttgt gtgcttaatc acgtatactc acgtgctcaa tagtcaccaa tgccctccct   7860
cttggccctc tccttttctt ttttcgaccg aattaattct taatcggcaa aaaaagaaaa   7920
gctccggatc aagattgtac gtaaggtgac aagctatttt tcaataaaga atatcttcca   7980
ctactgccat ctggcgtcat aactgcaaag tacacatata ttacgatgct gtctattaaa   8040
tgcttcctat attatatata tagtaatgtc gtttatggtg cactctcagt acaatctgct   8100
```

-continued

```
ctgatgccgc atagttaagc cagccccgac acccgccaac acccgctgac gcgccctgac   8160

gggcttgtct gctcccggca tccgcttaca gacaagctgt gaccgtctcc gggagctgca   8220

tgtgtcagag gttttcaccg tcatcaccga aacgcgcga                          8259


<210> SEQ ID NO 17
<211> LENGTH: 1089
<212> TYPE: DNA
<213> ORGANISM: Artificial
<220> FEATURE:
<223> OTHER INFORMATION: Mutagen

<400> SEQUENCE: 17

atgcttttgc gagctttcct tttcctcttg gctggttttg cagccaaaat atctgcagcg     60

ctagctgatg cagaattccg acatgactca ggatatgaag ttcatcatca aaaattggtg    120

ttctttgcag aagatgtggg ttcaaacaaa ggtgcaatca ttggactcat ggtgggcggt    180

gttgtcatag cgacagtgat cgtcatcacc ttggtgatgc tgaagaagaa aggtagatct    240

ggcaagctac tgtcttctat cgaacaagca tgcgatattt gccgacttaa aaagctcaag    300

tgctccaaag aaaaaccgaa gtgcgccaag tgtctgaaga acaactggga gtgtcgctac    360

tctcccaaaa ccaaaaggtc tccgctgact agggcacatc tgacagaagt ggaatcaagg    420

ctagaaagac tggaacagct atttctactg atttttcctc gagaagacct tgacatgatt    480

ttgaaaatgg attctttaca ggatataaaa gcattgttaa caggattatt tgtacaagat    540

aatgtgaata aagatgccgt cacagataga ttggcttcag tggagactga tatgcctcta    600

acattgagac agcatagaat aagtgcgaca tcatcatcgg aagagagtag taacaaaggt    660

caaagacagt tgactgtatc gccggaattc ccggggatct gggccccccc gaccgatgtc    720

agcctggggg acgagctcca cttagacggc gaggacgtgg cgatggcgca tgccgacgcg    780

ctagacgatt tcgatctgga catgttgggg gacggggatt ccccggggcc gggatttacc    840

ccccacgact ccgcccccta cggcgctctg gatatggccg acttcgagtt tgagcagatg    900

tttaccgatg cccttggaat tgacgagtac ggtgggggta ctagtggcca gtacacatcc    960

attcatcatg gtgtggtgga ggttgacgcc gctgtcaccc cagaggagcg ccacctgtcc   1020

aagatgcagc agaacggcta cgaaaatcca acctacaagt tctttgagca gatgcagaac   1080

ggcgcctag                                                           1089


<210> SEQ ID NO 18
<211> LENGTH: 362
<212> TYPE: PRT
<213> ORGANISM: Artificial
<220> FEATURE:
<223> OTHER INFORMATION: Mutein

<400> SEQUENCE: 18

Met Leu Leu Arg Ala Phe Leu Phe Leu Leu Ala Gly Phe Ala Ala Lys
1               5                   10                  15

Ile Ser Ala Ala Leu Ala Asp Ala Glu Phe Arg His Asp Ser Gly Tyr
            20                  25                  30

Glu Val His His Gln Lys Leu Val Phe Phe Ala Glu Asp Val Gly Ser
        35                  40                  45

Asn Lys Gly Ala Ile Ile Gly Leu Met Val Gly Gly Val Val Ile Ala
    50                  55                  60

Thr Val Ile Val Ile Thr Leu Val Met Leu Lys Lys Lys Gly Arg Ser
65                  70                  75                  80
```

-continued

```
Gly Lys Leu Leu Ser Ser Ile Glu Gln Ala Cys Asp Ile Cys Arg Leu
                85                  90                  95

Lys Lys Leu Lys Cys Ser Lys Glu Lys Pro Lys Cys Ala Lys Cys Leu
            100                 105                 110

Lys Asn Asn Trp Glu Cys Arg Tyr Ser Pro Lys Thr Lys Arg Ser Pro
        115                 120                 125

Leu Thr Arg Ala His Leu Thr Glu Val Glu Ser Arg Leu Glu Arg Leu
    130                 135                 140

Glu Gln Leu Phe Leu Leu Ile Phe Pro Arg Glu Asp Leu Asp Met Ile
145                 150                 155                 160

Leu Lys Met Asp Ser Leu Gln Asp Ile Lys Ala Leu Leu Thr Gly Leu
                165                 170                 175

Phe Val Gln Asp Asn Val Asn Lys Asp Ala Val Thr Asp Arg Leu Ala
            180                 185                 190

Ser Val Glu Thr Asp Met Pro Leu Thr Leu Arg Gln His Arg Ile Ser
        195                 200                 205

Ala Thr Ser Ser Ser Glu Glu Ser Ser Asn Lys Gly Gln Arg Gln Leu
    210                 215                 220

Thr Val Ser Pro Glu Phe Pro Gly Ile Trp Ala Pro Pro Thr Asp Val
225                 230                 235                 240

Ser Leu Gly Asp Glu Leu His Leu Asp Gly Glu Asp Val Ala Met Ala
                245                 250                 255

His Ala Asp Ala Leu Asp Asp Phe Asp Leu Asp Met Leu Gly Asp Gly
            260                 265                 270

Asp Ser Pro Gly Pro Gly Phe Thr Pro His Asp Ser Ala Pro Tyr Gly
        275                 280                 285

Ala Leu Asp Met Ala Asp Phe Glu Phe Glu Gln Met Phe Thr Asp Ala
    290                 295                 300

Leu Gly Ile Asp Glu Tyr Gly Gly Gly Thr Ser Gly Gln Tyr Thr Ser
305                 310                 315                 320

Ile His His Gly Val Val Glu Val Asp Ala Ala Val Thr Pro Glu Glu
                325                 330                 335

Arg His Leu Ser Lys Met Gln Gln Asn Gly Tyr Glu Asn Pro Thr Tyr
            340                 345                 350

Lys Phe Phe Glu Gln Met Gln Asn Gly Ala
        355                 360
```

<210> SEQ ID NO 19
<211> LENGTH: 1080
<212> TYPE: DNA
<213> ORGANISM: Artificial
<220> FEATURE:
<223> OTHER INFORMATION: Mutagen

<400> SEQUENCE: 19

```
atgcttttgc gagctttcct tttcctcttg gctggttttg cagccaaaat atctgcagcg     60

ctagctgatg cagaattccg acatgactca ggatatgaag ttcatcatca aaaattggtg    120

ttctttgcag aagatgtggg ttcaaacaaa ggtgcaatca ttggactcat ggtgggcggt    180

gttgtcatag cgacagtgat cgtcatcacc ttggtgatgc tgaagaagaa acagtacaca    240

tccattcatc atggtgtggt ggaggttgac gccgctgtca ccccagagga gcgccacctg    300

tccaagatgc agcagaacgg ctacgaaaat ccaacctaca agttctttga gcagatgcag    360

aacgcgcggg gtaccccggc gatgaagcta ctgtcttcta tcgaacaagc atgcgatatt    420

tgccgactta aaaagctcaa gtgctccaaa gaaaaaccga agtgcgccaa gtgtctgaag    480
```

-continued

```
aacaactggg agtgtcgcta ctctcccaaa accaaaaggt ctccgctgac tagggcacat    540

ctgacagaag tggaatcaag gctagaaaga ctggaacagc tatttctact gatttttcct    600

cgagaagacc ttgacatgat tttgaaaatg gattctttac aggatataaa agcattgtta    660

acaggattat ttgtacaaga taatgtgaat aaagatgccg tcacagatag attggcttca    720

gtggagactg atatgcctct aacattgaga cagcatagaa taagtgcgac atcatcatcg    780

gaagagagta gtaacaaagg tcaaagacag ttgactgtat cgccggaatt cccggggatc    840

tgggcccccc cgaccgatgt cagcctgggg gacgagctcc acttagacgg cgaggacgtg    900

gcgatggcgc atgccgacgc gctagacgat ttcgatctgg acatgttggg ggacggggat    960

tccccgggtc cgggatttac cccccacgac tccgccccct acggcgctct ggatatggcc   1020

gacttcgagt ttgagcagat gtttaccgat gcccttggaa ttgacgagta cggtgggtag   1080


<210> SEQ ID NO 20
<211> LENGTH: 359
<212> TYPE: PRT
<213> ORGANISM: Artificial
<220> FEATURE:
<223> OTHER INFORMATION: Mutein

<400> SEQUENCE: 20

Met Leu Leu Arg Ala Phe Leu Phe Leu Leu Ala Gly Phe Ala Ala Lys
1               5                   10                  15

Ile Ser Ala Ala Leu Ala Asp Ala Glu Phe Arg His Asp Ser Gly Tyr
            20                  25                  30

Glu Val His His Gln Lys Leu Val Phe Phe Ala Glu Asp Val Gly Ser
        35                  40                  45

Asn Lys Gly Ala Ile Ile Gly Leu Met Val Gly Gly Val Val Ile Ala
    50                  55                  60

Thr Val Ile Val Ile Thr Leu Val Met Leu Lys Lys Lys Gln Tyr Thr
65                  70                  75                  80

Ser Ile His His Gly Val Val Glu Val Asp Ala Ala Val Thr Pro Glu
                85                  90                  95

Glu Arg His Leu Ser Lys Met Gln Gln Asn Gly Tyr Glu Asn Pro Thr
            100                 105                 110

Tyr Lys Phe Phe Glu Gln Met Gln Asn Ala Arg Gly Thr Pro Ala Met
        115                 120                 125

Lys Leu Leu Ser Ser Ile Glu Gln Ala Cys Asp Ile Cys Arg Leu Lys
    130                 135                 140

Lys Leu Lys Cys Ser Lys Glu Lys Pro Lys Cys Ala Lys Cys Leu Lys
145                 150                 155                 160

Asn Asn Trp Glu Cys Arg Tyr Ser Pro Lys Thr Lys Arg Ser Pro Leu
                165                 170                 175

Thr Arg Ala His Leu Thr Glu Val Glu Ser Arg Leu Glu Arg Leu Glu
            180                 185                 190

Gln Leu Phe Leu Leu Ile Phe Pro Arg Glu Asp Leu Asp Met Ile Leu
        195                 200                 205

Lys Met Asp Ser Leu Gln Asp Ile Lys Ala Leu Leu Thr Gly Leu Phe
    210                 215                 220

Val Gln Asp Asn Val Asn Lys Asp Ala Val Thr Asp Arg Leu Ala Ser
225                 230                 235                 240

Val Glu Thr Asp Met Pro Leu Thr Leu Arg Gln His Arg Ile Ser Ala
                245                 250                 255
```

-continued

```
Thr Ser Ser Ser Glu Glu Ser Ser Asn Lys Gly Gln Arg Gln Leu Thr
            260                 265                 270

Val Ser Pro Glu Phe Pro Gly Ile Trp Ala Pro Pro Thr Asp Val Ser
        275                 280                 285

Leu Gly Asp Glu Leu His Leu Asp Gly Glu Asp Val Ala Met Ala His
    290                 295                 300

Ala Asp Ala Leu Asp Asp Phe Asp Leu Asp Met Leu Gly Asp Gly Asp
305                 310                 315                 320

Ser Pro Gly Pro Gly Phe Thr Pro His Asp Ser Ala Pro Tyr Gly Ala
                325                 330                 335

Leu Asp Met Ala Asp Phe Glu Phe Glu Gln Met Phe Thr Asp Ala Leu
            340                 345                 350

Gly Ile Asp Glu Tyr Gly Gly
        355


<210> SEQ ID NO 21
<211> LENGTH: 1074
<212> TYPE: DNA
<213> ORGANISM: Artificial
<220> FEATURE:
<223> OTHER INFORMATION: Mutagen

<400> SEQUENCE: 21

atgagggcct ggatcttctt tctcctttgc ctggccggga gggctctggc agccccgcta     60

gctgatgcag aattccgaca tgactcagga tatgaagttc atcatcaaaa attggtgttc    120

tttgcagaag atgtgggttc aaacaaaggt gcaatcattg gactcatggt gggcggtgtt    180

gtcatagcga cagtgatcgt catcaccttg gtgatgctga agaagaaaca gtacacatcc    240

attcatcatg gtgtggtgga ggttgacgcc gctgtcaccc cagaggagcg ccacctgtcc    300

aagatgcagc agaacggcta cgaaaatcca acctacaagt tctttgagca gatgcagaac    360

gcgcggggta ccccggcgat gaagctactg tcttctatcg aacaagcatg cgatatttgc    420

cgacttaaaa agctcaagtg ctccaaagaa aaaccgaagt gcgccaagtg tctgaagaac    480

aactgggagt gtcgctactc tcccaaaacc aaaaggtctc cgctgactag ggcacatctg    540

acagaagtgg aatcaaggct agaaagactg gaacagctat ttctactgat tttcctcga     600

gaagaccttg acatgatttt gaaaatggat tctttacagg atataaaagc attgttaaca    660

ggattatttg tacaagataa tgtgaataaa gatgccgtca cagatagatt ggcttcagtg    720

gagactgata tgcctctaac attgagacag catagaataa gtgcgacatc atcatcggaa    780

gagagtagta acaaaggtca aagacagttg actgtatcgc cggaattccc ggggatctgg    840

gcccccccga ccgatgtcag cctgggggac gagctccact tagacggcga ggacgtggcg    900

atggcgcatg ccgacgcgct agacgatttc gatctggaca tgttggggga cggggattcc    960

ccgggtccgg gatttacccc ccacgactcc gccccctacg gcgctctgga tatggccgac   1020

ttcgagtttg agcagatgtt taccgatgcc cttggaattg acgagtacgg tggg         1074


<210> SEQ ID NO 22
<211> LENGTH: 358
<212> TYPE: PRT
<213> ORGANISM: Artificial
<220> FEATURE:
<223> OTHER INFORMATION: Mutein

<400> SEQUENCE: 22

Met Arg Ala Trp Ile Phe Phe Leu Leu Cys Leu Ala Gly Arg Ala Leu
1               5                   10                  15
```

-continued

```
Ala Ala Pro Leu Ala Asp Ala Glu Phe Arg His Asp Ser Gly Tyr Glu
            20                  25                  30

Val His His Gln Lys Leu Val Phe Phe Ala Glu Asp Val Gly Ser Asn
        35                  40                  45

Lys Gly Ala Ile Ile Gly Leu Met Val Gly Gly Val Val Ile Ala Thr
    50                  55                  60

Val Ile Val Ile Thr Leu Val Met Leu Lys Lys Lys Gln Tyr Thr Ser
65                  70                  75                  80

Ile His His Gly Val Val Glu Val Asp Ala Ala Val Thr Pro Glu Glu
                85                  90                  95

Arg His Leu Ser Lys Met Gln Gln Asn Gly Tyr Glu Asn Pro Thr Tyr
            100                 105                 110

Lys Phe Phe Glu Gln Met Gln Asn Ala Arg Gly Thr Pro Ala Met Lys
        115                 120                 125

Leu Leu Ser Ser Ile Glu Gln Ala Cys Asp Ile Cys Arg Leu Lys Lys
    130                 135                 140

Leu Lys Cys Ser Lys Glu Lys Pro Lys Cys Ala Lys Cys Leu Lys Asn
145                 150                 155                 160

Asn Trp Glu Cys Arg Tyr Ser Pro Lys Thr Lys Arg Ser Pro Leu Thr
                165                 170                 175

Arg Ala His Leu Thr Glu Val Glu Ser Arg Leu Glu Arg Leu Glu Gln
            180                 185                 190

Leu Phe Leu Leu Ile Phe Pro Arg Glu Asp Leu Asp Met Ile Leu Lys
        195                 200                 205

Met Asp Ser Leu Gln Asp Ile Lys Ala Leu Leu Thr Gly Leu Phe Val
    210                 215                 220

Gln Asp Asn Val Asn Lys Asp Ala Val Thr Asp Arg Leu Ala Ser Val
225                 230                 235                 240

Glu Thr Asp Met Pro Leu Thr Leu Arg Gln His Arg Ile Ser Ala Thr
                245                 250                 255

Ser Ser Ser Glu Glu Ser Ser Asn Lys Gly Gln Arg Gln Leu Thr Val
            260                 265                 270

Ser Pro Glu Phe Pro Gly Ile Trp Ala Pro Pro Thr Asp Val Ser Leu
        275                 280                 285

Gly Asp Glu Leu His Leu Asp Gly Glu Asp Val Ala Met Ala His Ala
    290                 295                 300

Asp Ala Leu Asp Asp Phe Asp Leu Asp Met Leu Gly Asp Gly Asp Ser
305                 310                 315                 320

Pro Gly Pro Gly Phe Thr Pro His Asp Ser Ala Pro Tyr Gly Ala Leu
                325                 330                 335

Asp Met Ala Asp Phe Glu Phe Glu Gln Met Phe Thr Asp Ala Leu Gly
            340                 345                 350

Ile Asp Glu Tyr Gly Gly
        355
```

<210> SEQ ID NO 23
<211> LENGTH: 95
<212> TYPE: DNA
<213> ORGANISM: Artificial
<220> FEATURE:
<223> OTHER INFORMATION: primer

<400> SEQUENCE: 23
gctctagaat gcttttgcaa gctttccttt tccttttggc tggttttgca gccaaaatat     60

-continued ctgcagcgct agctgatgca gaattccgac atgac 95

<210> SEQ ID NO 24
<211> LENGTH: 39
<212> TYPE: DNA
<213> ORGANISM: Artificial
<220> FEATURE:
<223> OTHER INFORMATION: primer

<400> SEQUENCE: 24
cgggatccct aggcgccgtt ctgcatctgc tcaaagaac 39

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
actatatcta gaatgctttt gc 22

<210> SEQ ID NO 26
<211> LENGTH: 54
<212> TYPE: DNA
<213> ORGANISM: Artificial
<220> FEATURE:
<223> OTHER INFORMATION: primer

<400> SEQUENCE: 26
ttcgatagaa gacagtagct tgccagatct acctttcttc ttcagcatca ccaa 54

<210> SEQ ID NO 27
<211> LENGTH: 54
<212> TYPE: DNA
<213> ORGANISM: Artificial
<220> FEATURE:
<223> OTHER INFORMATION: primer

<400> SEQUENCE: 27
ttggtgatgc tgaagaagaa aggtagatct ggcaagctac tgtcttctat cgaa 54

<210> SEQ ID NO 28
<211> LENGTH: 52
<212> TYPE: DNA
<213> ORGANISM: Artificial
<220> FEATURE:
<223> OTHER INFORMATION: primer

<400> SEQUENCE: 28
atgatgaatg gatgtgtact ggccactagt acccccaccg tactcgtcaa tt 52

<210> SEQ ID NO 29
<211> LENGTH: 52
<212> TYPE: DNA
<213> ORGANISM: Artificial
<220> FEATURE:
<223> OTHER INFORMATION: primer

<400> SEQUENCE: 29
aattgacgag tacggtgggg gtactagtgg ccagtacaca tccattcatc at 52

<210> SEQ ID NO 30
<211> LENGTH: 22
<212> TYPE: DNA
<213> ORGANISM: Artificial

-continued

<220> FEATURE:
<223> OTHER INFORMATION: primer

<400> SEQUENCE: 30
cgataagctt gatatcgaat tc 22

<210> SEQ ID NO 31
<211> LENGTH: 26
<212> TYPE: DNA
<213> ORGANISM: Artificial
<220> FEATURE:
<223> OTHER INFORMATION: primer

<400> SEQUENCE: 31
ccatcgattt tctaaccccc accgta 26

<210> SEQ ID NO 32
<211> LENGTH: 6634
<212> TYPE: DNA
<213> ORGANISM: Artificial
<220> FEATURE:
<223> OTHER INFORMATION: recombinant plasmid

<400> SEQUENCE: 32
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttaact ggcttatcga aattaatacg actcactata gggagaccca agcttctgcc 900
tgccgcctgc ctgcctgcca ctgagggttc ccagcaccat gagggcctgg atcttctttc 960
tcctttgcct ggccgggagg gctctggcag ccccgctagc tgatgcagaa ttccgacatg 1020
actcaggata tgaagttcat catcaaaaat tggtgttctt tgcagaagat gtgggttcaa 1080
acaaaggtgc aatcattgga ctcatggtgg gcggtgttgt catagcgaca gtgatcgtca 1140
tcaccttggt gatgctgaag aagaaaggta gatctggcaa gctactgtct tctatcgaac 1200
aagcatgcga tatttgccga cttaaaaagc tcaagtgctc caaagaaaaa ccgaagtgcg 1260
ccaagtgtct gaagaacaac tgggagtgtc gctactctcc caaaaccaaa aggtctccgc 1320
tgactagggc acatctgaca gaagtggaat caaggctaga aagactggaa cagctatttc 1380
tactgatttt tcctcgagaa gaccttgaca tgattttgaa aatggattct ttacaggata 1440
taaaagcatt gttaacagga ttatttgtac aagataatgt gaataaagat gccgtcacag 1500

-continued atagattggc ttcagtggag actgatatgc ctctaacatt gagacagcat agaataagtg 1560
cgacatcatc atcggaagag agtagtaaca aaggtcaaag acagttgact gtatcgccgg 1620
aattcccggg gatctgggcc cccccgaccg atgtcagcct gggggacgag ctccacttag 1680
acggcgagga cgtggcgatg gcgcatgccg acgcgctaga cgatttcgat ctggacatgt 1740
tgggggacgg ggattccccg gggccgggat ttacccccca cgactccgcc ccctacggcg 1800
ctctggatat ggccgacttc gagtttgagc agatgtttac cgatgccctt ggaattgacg 1860
agtacggtgg gggtactagt ggccagtaca catccattca tcatggtgtg gtggaggttg 1920
acgccgctgt caccccagag gagcgccacc tgtccaagat gcagcagaac ggctacgaaa 1980
atccaaccta caagttcttt gagcagatgc agaacggcgc ctagggatcc cccgggctgc 2040
aggaattcga tatcaagctt atcgataccg tcgaggccgc tcgagcatgc atctagaggg 2100
ccctattcta tagtgtcacc taaatgctag agctcgctga tcagcctcga ctgtgccttc 2160
tagttgccag ccatctgttg tttgcccctc ccccgtgcct tccttgaccc tggaaggtgc 2220
cactcccact gtcctttcct aataaaatga ggaaattgca tcgcattgtc tgagtaggtg 2280
tcattctatt ctggggggtg gggtggggca ggacagcaag ggggaggatt gggaagacaa 2340
tagcaggcat gctggggatg cggtgggctc tatggaacca gctggggctc gagggggggat 2400 ccccacgcgc cctgtagcgg cgcattaagc gcggcgggtg tggtggttac gcgcagcgtg 2460
accgctacac ttgccagcgc cctagcgccc gctcctttcg ctttcttccc ttcctttctc 2520
gccacgttcg ccggctttcc ccgtcaagct ctaaatcggg gcatcccttt agggttccga 2580
tttagtgctt tacggcacct cgaccccaaa aaacttgatt agggtgatgg ttcacgtagt 2640
gggccatcgc cctgatagac ggtttttcgc cctttgacgt tggagtccac gttctttaat 2700
agtggactct tgttccaaac tggaacaaca ctcaacccta tctcggtcta ttcttttgat 2760
ttataaggga ttttggggat ttcggcctat tggttaaaaa atgagctgat ttaacaaaaa 2820
tttaacgcga attttaacaa aatattaacg tttacaattt aaatatttgc ttatacaatc 2880
ttcctgtttt tggggctttt ctgattatca accggggtgg gtaccgagct cgaattctgt 2940
ggaatgtgtg tcagttaggg tgtggaaagt ccccaggctc cccaggcagg cagaagtatg 3000
caaagcatgc atctcaatta gtcagcaacc aggtgtggaa agtccccagg ctccccagca 3060
ggcagaagta tgcaaagcat gcatctcaat tagtcagcaa ccatagtccc gcccctaact 3120
ccgcccatcc cgcccctaac tccgcccagt tccgcccatt ctccgcccca tggctgacta 3180
atttttttta tttatgcaga ggccgaggcc gcctcggcct ctgagctatt ccagaagtag 3240
tgaggaggct tttttggagg cctaggcttt tgcaaaaagc tcccgggagc ttggatatcc 3300
attttcggat ctgatcaaga gacaggatga ggatcgtttc gcatgattga acaagatgga 3360
ttgcacgcag gttctccggc cgcttgggtg gagaggctat tcggctatga ctgggcacaa 3420
cagacaatcg gctgctctga tgccgccgtg ttccggctgt cagcgcaggg gcgcccggtt 3480
ctttttgtca agaccgacct gtccggtgcc ctgaatgaac tgcaggacga ggcagcgcgg 3540
ctatcgtggc tggccacgac gggcgttcct tgcgcagctg tgctcgacgt tgtcactgaa 3600
gcgggaaggg actggctgct attgggcgaa gtgccggggc aggatctcct gtcatctcac 3660
cttgctcctg ccgagaaagt atccatcatg gctgatgcaa tgcggcggct gcatacgctt 3720
gatccggcta cctgcccatt cgaccaccaa gcgaaacatc gcatcgagcg agcacgtact 3780
cggatggaag ccggtcttgt cgatcaggat gatctggacg aagagcatca ggggctcgcg 3840
ccagccgaac tgttcgccag gctcaaggcg cgcatgcccg acggcgagga tctcgtcgtg 3900

-continued

```
acccatggcg atgcctgctt gccgaatatc atggtggaaa atggccgctt ttctggattc   3960

atcgactgtg gccggctggg tgtggcggac cgctatcagg acatagcgtt ggctacccgt   4020

gatattgctg aagagcttgg cggcgaatgg gctgaccgct tcctcgtgct ttacggtatc   4080

gccgctcccg attcgcagcg catcgccttc tatcgccttc ttgacgagtt cttctgagcg   4140

ggactctggg gttcgaaatg accgaccaag cgacgcccaa cctgccatca cgagatttcg   4200

attccaccgc cgccttctat gaaaggttgg gcttcggaat cgttttccgg gacgccggct   4260

ggatgatcct ccagcgcggg gatctcatgc tggagttctt cgcccacccc aacttgttta   4320

ttgcagctta taatggttac aaataaagca atagcatcac aaatttcaca aataaagcat   4380

tttttcact gcattctagt tgtggtttgt ccaaactcat caatgtatct tatcatgtct   4440

ggatcccgtc gacctcgaga gcttggcgta atcatggtca tagctgtttc ctgtgtgaaa   4500

ttgttatccg ctcacaattc cacacaacat acgagccgga agcataaagt gtaaagcctg   4560

gggtgcctaa tgagtgagct aactcacatt aattgcgttg cgctcactgc ccgctttcca   4620

gtcgggaaac ctgtcgtgcc agctgcatta atgaatcggc caacgcgcgg ggagaggcgg   4680

tttgcgtatt gggcgctctt ccgcttcctc gctcactgac tcgctgcgct cggtcgttcg   4740

gctgcggcga gcggtatcag ctcactcaaa ggcggtaata cggttatcca cagaatcagg   4800

ggataacgca ggaaagaaca tgtgagcaaa aggccagcaa aaggccagga accgtaaaaa   4860

ggccgcgttg ctggcgtttt tccataggct ccgcccccct gacgagcatc acaaaaatcg   4920

acgctcaagt cagaggtggc gaaacccgac aggactataa agataccagg cgtttccccc   4980

tggaagctcc ctcgtgcgct ctcctgttcc gaccctgccg cttaccggat acctgtccgc   5040

ctttctccct tcgggaagcg tggcgctttc tcaatgctca cgctgtaggt atctcagttc   5100

ggtgtaggtc gttcgctcca agctgggctg tgtgcacgaa ccccccgttc agcccgaccg   5160

ctgcgcctta tccggtaact atcgtcttga gtccaacccg gtaagacacg acttatcgcc   5220

actggcagca gccactggta acaggattag cagagcgagg tatgtaggcg gtgctacaga   5280

gttcttgaag tggtggccta actacggcta cactagaagg acagtatttg gtatctgcgc   5340

tctgctgaag ccagttacct tcggaaaaag agttggtagc tcttgatccg gcaaacaaac   5400

caccgctggt agcggtggtt tttttgtttg caagcagcag attacgcgca gaaaaaaagg   5460

atctcaagaa gatcctttga tcttttctac ggggtctgac gctcagtgga acgaaaactc   5520

acgttaaggg attttggtca tgagattatc aaaaaggatc ttcacctaga tccttttaaa   5580

ttaaaaatga agttttaaat caatctaaag tatatatgag taaacttggt ctgacagtta   5640

ccaatgctta atcagtgagg cacctatctc agcgatctgt ctatttcgtt catccatagt   5700

tgcctgactc cccgtcgtgt agataactac gatacgggag ggcttaccat ctggccccag   5760

tgctgcaatg ataccgcgag acccacgctc accggctcca gatttatcag caataaacca   5820

gccagccgga agggccgagc gcagaagtgg tcctgcaact ttatccgcct ccatccagtc   5880

tattaattgt tgccgggaag ctagagtaag tagttcgcca gttaatagtt tgcgcaacgt   5940

tgttgccatt gctacaggca tcgtggtgtc acgctcgtcg tttggtatgg cttcattcag   6000

ctccggttcc caacgatcaa ggcgagttac atgatccccc atgttgtgca aaaaagcggt   6060

tagctccttc ggtcctccga tcgttgtcag aagtaagttg gccgcagtgt tatcactcat   6120

ggttatggca gcactgcata attctcttac tgtcatgcca tccgtaagat gcttttctgt   6180

gactggtgag tactcaacca agtcattctg agaatagtgt atgcggcgac cgagttgctc   6240
```

-continued

```
ttgcccggcg tcaatacggg ataataccgc gccacatagc agaactttaa aagtgctcat   6300

cattggaaaa cgttcttcgg ggcgaaaact ctcaaggatc ttaccgctgt tgagatccag   6360

ttcgatgtaa cccactcgtg cacccaactg atcttcagca tcttttactt tcaccagcgt   6420

ttctgggtga gcaaaaacag gaaggcaaaa tgccgcaaaa aagggaataa gggcgacacg   6480

gaaatgttga atactcatac tcttcctttt tcaatattat tgaagcattt atcagggtta   6540

ttgtctcatg agcggataca tatttgaatg tatttagaaa aataaacaaa taggggttcc   6600

gcgcacattt ccccgaaaag tgccacctga cgtc                                6634


<210> SEQ ID NO 33
<211> LENGTH: 24
<212> TYPE: PRT
<213> ORGANISM: Artificial
<220> FEATURE:
<223> OTHER INFORMATION: APP transmembrane domain
<220> FEATURE:
<221> NAME/KEY: MISC_FEATURE
<222> LOCATION: (12)..(12)
<223> OTHER INFORMATION: gamma-secretase cleavage site
<220> FEATURE:
<221> NAME/KEY: MISC_FEATURE
<222> LOCATION: (14)..(14)
<223> OTHER INFORMATION: gamma-secretase cleavage site

<400> SEQUENCE: 33

Gly Ala Ile Ile Gly Leu Met Val Gly Gly Val Val Ile Ala Thr Val
1               5                   10                  15

Ile Val Ile Thr Leu Val Met Leu
            20
```